United States Patent
Ooshima et al.

(10) Patent No.: US 8,014,958 B2
(45) Date of Patent: Sep. 6, 2011

(54) METHOD FOR CONFIRMING POSITIONS ON WHICH PROBES ARE IMMOBILIZED IN NUCLEIC ACID ARRAY

(75) Inventors: Hiroyuki Ooshima, Yokohama (JP); Yuichiro Nagata, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 685 days.

(21) Appl. No.: 12/091,522

(22) PCT Filed: Oct. 30, 2006

(86) PCT No.: PCT/JP2006/322063
§ 371 (c)(1),
(2), (4) Date: Apr. 25, 2008

(87) PCT Pub. No.: WO2007/049827
PCT Pub. Date: May 3, 2007

(65) Prior Publication Data
US 2009/0247419 A1    Oct. 1, 2009

(30) Foreign Application Priority Data
Oct. 28, 2005  (JP) .................................. 2005-315190

(51) Int. Cl.
*G01N 33/53* (2006.01)
*C12M 1/00* (2006.01)
*C12N 15/09* (2006.01)
(52) U.S. Cl. ........................................... 702/19; 702/20
(58) Field of Classification Search ........................ None
See application file for complete search history.

(56) References Cited

U.S. PATENT DOCUMENTS
2003/0170672 A1   9/2003   Cho et al.
2003/0211496 A1   11/2003  Getts et al.

FOREIGN PATENT DOCUMENTS
WO        2004/003233 A1    1/2004

*Primary Examiner* — Michael Borin
(74) *Attorney, Agent, or Firm* — McDermott Will & Emery LLP

(57) ABSTRACT

The present invention provides a method for accurately and easily confirming that nucleic acid probes immobilized on a nucleic acid array are correctly arrayed on predetermined positions.

5 Claims, 3 Drawing Sheets

Figure 2

| column \ row | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| 1 | B | B | B | B | B | B | B | B | B | B | B | B | B | B | B | B | B | B | B |
| 2 | B | 96 | 97 | 98 | 99 | 100 | 101 | 102 | B | B | B | 103 | 104 | 105 | 106 | 107 | 108 | 109 | B |
| 3 | B | 110 | 111 | 112 | 113 | 114 | 115 | 116 | 117 | 118 | 119 | 120 | 121 | 122 | 123 | 124 | 125 | 126 | B |
| 4 | B | 127 | 128 | 129 | 130 | 131 | 132 | 133 | 134 | 135 | 136 | 137 | 138 | 139 | 140 | 141 | 142 | 143 | B |
| 5 | B | 144 | 70 | 71 | 72 | 73 | 74 | 75 | 76 | 77 | 78 | 79 | 80 | 81 | 82 | 83 | 84 | 85 | B |
| 6 | B | 86 | 87 | 88 | 89 | 90 | 91 | 92 | B | B | B | 93 | 94 | 95 | 1 | 2 | 3 | 4 | B |
| 7 | B | 5 | 6 | 7 | 8 | 9 | 10 | 11 | 12 | 13 | 14 | 15 | 16 | 17 | 18 | 19 | 20 | 21 | B |
| 8 | B | 22 | 23 | 24 | 25 | 26 | 27 | 28 | 29 | 30 | 31 | 32 | 33 | 34 | 35 | 36 | 37 | 38 | B |
| 9 | B | 39 | 40 | 41 | 42 | 43 | 44 | 45 | B | B | B | 46 | 47 | 48 | 49 | 50 | 51 | 52 | B |
| 10 | B | 53 | 54 | 55 | 56 | 57 | 58 | 59 | 60 | 61 | 62 | 63 | 64 | 65 | 66 | 67 | 68 | 69 | B |
| 11 | B | 145 | 146 | 147 | 148 | 149 | 150 | 151 | 152 | 153 | 154 | 155 | 156 | 157 | 158 | 159 | 160 | 161 | B |
| 12 | B | 162 | 163 | 164 | 165 | 166 | 167 | 168 | 169 | 170 | 171 | 172 | 173 | 174 | 175 | 176 | 177 | 178 | B |
| 13 | B | 179 | 180 | 181 | 182 | 183 | 184 | 185 | B | B | B | 186 | 187 | 188 | 189 | 190 | 191 | 192 | B |

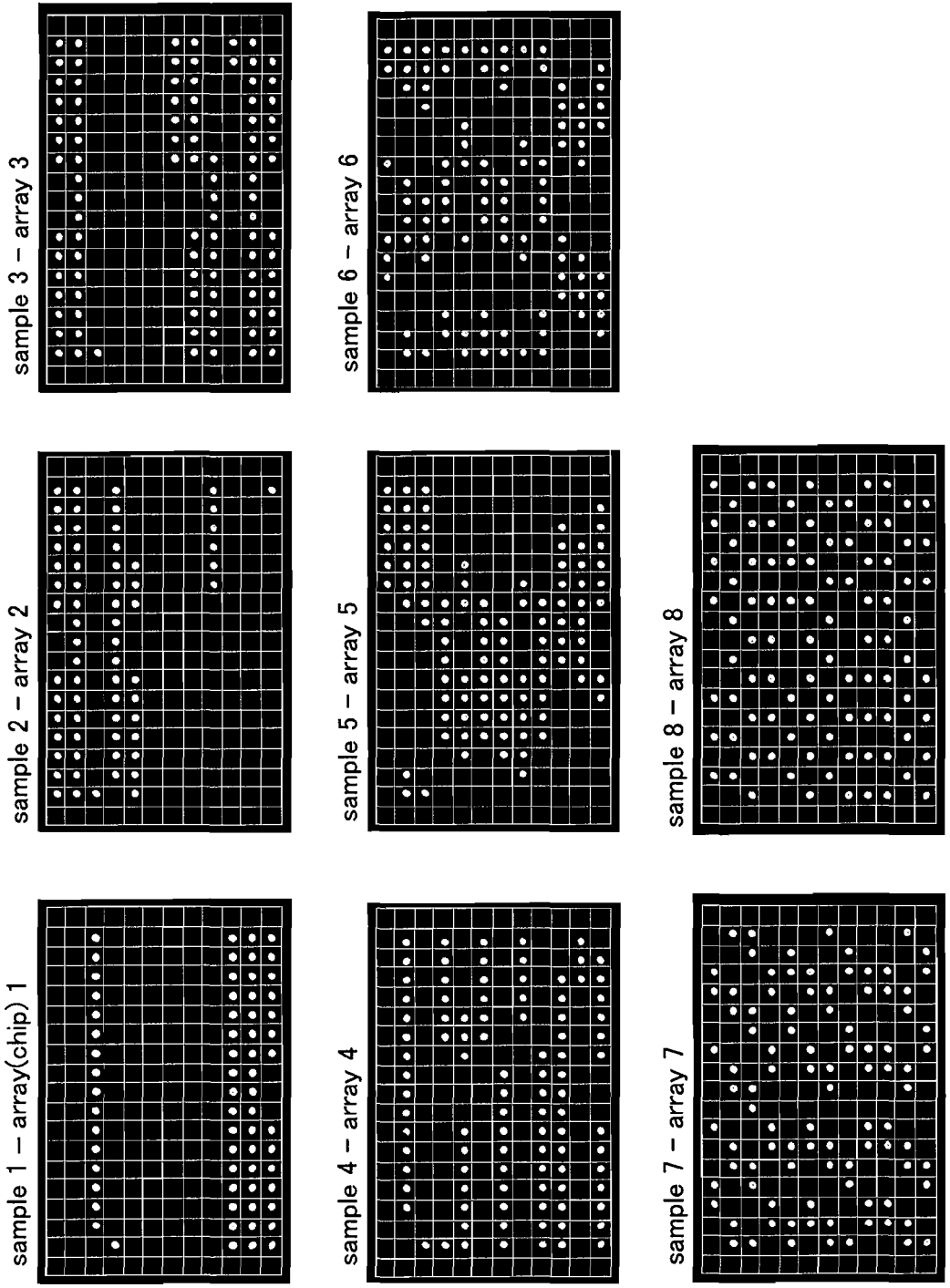

```
                         SEQUENCE LISTING

<160> NUMBER OF SEQ ID NOS: 385

<210> SEQ ID NO 1
<211> LENGTH: 65
<212> TYPE: DNA
<213> ORGANISM: Artificial
<220> FEATURE:
<223> OTHER INFORMATION: synthetic DNA

<400> SEQUENCE: 1
actgttgaca ccataaaaga ttctgacgaa gagctggaca acaatcagat agaagtactg    60
gacca                                                                65

<210> SEQ ID NO 2
<211> LENGTH: 65
<212> TYPE: DNA
<213> ORGANISM: Artificial
<220> FEATURE:
<223> OTHER INFORMATION: synthetic DNA

<400> SEQUENCE: 2
gatcgtcagc caatggatcg tgggcaatgg acacgcaact gatctctggc agaactgtag    60
cacct                                                                65

<210> SEQ ID NO 3
<211> LENGTH: 65
<212> TYPE: DNA
<213> ORGANISM: Artificial
<220> FEATURE:
<223> OTHER INFORMATION: synthetic DNA

<400> SEQUENCE: 3
tcatggcccc tctgacctgc actggggagc ccgtctcagt gttgagcctt ttccctcttt    60
ggctc                                                                65

<210> SEQ ID NO 4
<211> LENGTH: 65
<212> TYPE: DNA
<213> ORGANISM: Artificial
<220> FEATURE:
<223> OTHER INFORMATION: synthetic DNA

<400> SEQUENCE: 4
cgccatctcc actgcatccg atctcattat ttcggtggtt gcttgggggt gaacaatttt    60
gtggc                                                                65

<210> SEQ ID NO 5
<211> LENGTH: 65
```

```
<212> TYPE: DNA
<213> ORGANISM: Artificial
<220> FEATURE:
<223> OTHER INFORMATION: synthetic DNA

<400> SEQUENCE: 5
tatgaagtca tgcgtttaat cacattcgag tgtttcagtg cttcgcagat gtccttgatg     60
ctcat                                                                 65

<210> SEQ ID NO 6
<211> LENGTH: 65
<212> TYPE: DNA
<213> ORGANISM: Artificial
<220> FEATURE:
<223> OTHER INFORMATION: synthetic DNA

<400> SEQUENCE: 6
gatattgtgg acacggccat gcctatcacc atttgtatag cttattttaa caattgcctg     60
aatcc                                                                 65

<210> SEQ ID NO 7
<211> LENGTH: 65
<212> TYPE: DNA
<213> ORGANISM: Artificial
<220> FEATURE:
<223> OTHER INFORMATION: synthetic DNA

<400> SEQUENCE: 7
gctaaagtcc aagagaggat ccgagaacgc tctaagcctg tccacgagct caatagggaa     60
gcctg                                                                 65

<210> SEQ ID NO 8
<211> LENGTH: 65
<212> TYPE: DNA
<213> ORGANISM: Artificial
<220> FEATURE:
<223> OTHER INFORMATION: synthetic DNA

<400> SEQUENCE: 8
agcctatggt cccggatgac atctgtttaa aaacaagcac aacctgcaac atactttgat     60
tacct                                                                 65

<210> SEQ ID NO 9
<211> LENGTH: 65
<212> TYPE: DNA
<213> ORGANISM: Artificial
<220> FEATURE:
<223> OTHER INFORMATION: synthetic DNA

<400> SEQUENCE: 9
tatttggttt cacaatggag gagcgctcat gggggcccta tatcacctgt attcagggcc     60
tatgt                                                                 65

<210> SEQ ID NO 10
<211> LENGTH: 65
<212> TYPE: DNA
<213> ORGANISM: Artificial
<220> FEATURE:
<223> OTHER INFORMATION: synthetic DNA

<400> SEQUENCE: 10
taatggtgcc catgatgagt ttgcatcacc tgactatacc ttacttccgg gacgaggagc     60
tgtcc                                                                 65
```

<210> SEQ ID NO 11
<211> LENGTH: 65
<212> TYPE: DNA
<213> ORGANISM: Artificial
<220> FEATURE:
<223> OTHER INFORMATION: synthetic DNA

<400> SEQUENCE: 11
cacaagacac agaatagttt acacactgtg tggggacgg cttctcacgc tttgtttact    60
ctctt                                                              65

<210> SEQ ID NO 12
<211> LENGTH: 65
<212> TYPE: DNA
<213> ORGANISM: Artificial
<220> FEATURE:
<223> OTHER INFORMATION: synthetic DNA

<400> SEQUENCE: 12
caaggctaag tttgccggca ggaacttcag aaacccttg gccaagtaag ctgtgggcag    60
gcaag                                                              65

<210> SEQ ID NO 13
<211> LENGTH: 65
<212> TYPE: DNA
<213> ORGANISM: Artificial
<220> FEATURE:
<223> OTHER INFORMATION: synthetic DNA

<400> SEQUENCE: 13
taatacagtg cttcatatca gctctcttct tgcatggaca ctactgctga ccatatgccc    60
aatca                                                              65

<210> SEQ ID NO 14
<211> LENGTH: 65
<212> TYPE: DNA
<213> ORGANISM: Artificial
<220> FEATURE:
<223> OTHER INFORMATION: synthetic DNA

<400> SEQUENCE: 14
ctctagtttt cagccttggg aggttttatt ctgacttcct ctgattttgg catgtggaga    60
cactc                                                              65

<210> SEQ ID NO 15
<211> LENGTH: 65
<212> TYPE: DNA
<213> ORGANISM: Artificial
<220> FEATURE:
<223> OTHER INFORMATION: synthetic DNA

<400> SEQUENCE: 15
ttcccctgtg agtgaaatgc cttctagtag tgaaccgtcc tcgggagccg actatgacta    60
ctcag                                                              65

<210> SEQ ID NO 16
<211> LENGTH: 65
<212> TYPE: DNA
<213> ORGANISM: Artificial
<220> FEATURE:
<223> OTHER INFORMATION: synthetic DNA

<400> SEQUENCE: 16

```
ggagaatgca aatatataga gcacctggaa gcagtaacat gcaaatgtca gcaagaatat      60
ttcgg                                                                  65

<210> SEQ ID NO 17
<211> LENGTH: 65
<212> TYPE: DNA
<213> ORGANISM: Artificial
<220> FEATURE:
<223> OTHER INFORMATION: synthetic DNA

<400> SEQUENCE: 17
gatatacatg ctcaaccttc atcggcccac gtgtattgtc cgggctcaga atgggaggac      60
tccag                                                                  65

<210> SEQ ID NO 18
<211> LENGTH: 65
<212> TYPE: DNA
<213> ORGANISM: Artificial
<220> FEATURE:
<223> OTHER INFORMATION: synthetic DNA

<400> SEQUENCE: 18
gctcaatatg ccccaggcta tgacaaagtc aaggacatct cagaggtggt caccccctcgg     60 ttcct                                                                  65

<210> SEQ ID NO 19
<211> LENGTH: 65
<212> TYPE: DNA
<213> ORGANISM: Artificial
<220> FEATURE:
<223> OTHER INFORMATION: synthetic DNA

<400> SEQUENCE: 19
caaacagttc gacactgacc gatcagggac catttgcagt agtgaactcc caggtgcctt      60
tgagg                                                                  65

<210> SEQ ID NO 20
<211> LENGTH: 65
<212> TYPE: DNA
<213> ORGANISM: Artificial
<220> FEATURE:
<223> OTHER INFORMATION: synthetic DNA

<400> SEQUENCE: 20
caactggact atgttgacct ctatcttctt catttcccaa tggctctcaa gccaggtgag      60
acgcc                                                                  65

<210> SEQ ID NO 21
<211> LENGTH: 65
<212> TYPE: DNA
<213> ORGANISM: Artificial
<220> FEATURE:
<223> OTHER INFORMATION: synthetic DNA

<400> SEQUENCE: 21
aggagagctt ctccaaaggc tgagggacat ttccacagtc aagagcctct ttgccaagcg      60
acaac                                                                  65

<210> SEQ ID NO 22
<211> LENGTH: 65
<212> TYPE: DNA
<213> ORGANISM: Artificial
```

```
<220> FEATURE:
<223> OTHER INFORMATION: synthetic DNA

<400> SEQUENCE: 22
gaaagggcct tgacatcagt tcctttgtgt gtactcactg aagcctgcgt tggtccagag    60
cggag                                                                65

<210> SEQ ID NO 23
<211> LENGTH: 65
<212> TYPE: DNA
<213> ORGANISM: Artificial
<220> FEATURE:
<223> OTHER INFORMATION: synthetic DNA

<400> SEQUENCE: 23
ggtggtgatc ggcatggatg tggcagcatc tgagttctat cgcaatggga agtacgatct    60
tgact                                                                65

<210> SEQ ID NO 24
<211> LENGTH: 65
<212> TYPE: DNA
<213> ORGANISM: Artificial
<220> FEATURE:
<223> OTHER INFORMATION: synthetic DNA

<400> SEQUENCE: 24
agcccgttcc gcagggacta gaggctttcg gcttttttggg acagcaacta ccttgctttt    60
ggaaa                                                                65

<210> SEQ ID NO 25
<211> LENGTH: 65
<212> TYPE: DNA
<213> ORGANISM: Artificial
<220> FEATURE:
<223> OTHER INFORMATION: synthetic DNA

<400> SEQUENCE: 25
tcttacttct acaggttcct tgagcaccaa agatgattca taactctgta taggtgacag    60
ctgct                                                                65

<210> SEQ ID NO 26
<211> LENGTH: 65
<212> TYPE: DNA
<213> ORGANISM: Artificial
<220> FEATURE:
<223> OTHER INFORMATION: synthetic DNA

<400> SEQUENCE: 26
tacgttaaaa gctgtgctgg atattgcgtg atcacctata tacttggagt tggagacagg    60
cacct                                                                65

<210> SEQ ID NO 27
<211> LENGTH: 65
<212> TYPE: DNA
<213> ORGANISM: Artificial
<220> FEATURE:
<223> OTHER INFORMATION: synthetic DNA

<400> SEQUENCE: 27
tggcttgctt ggtgggacct gacgagttgg tggcatggga aggatgtggg tctctagtgc    60
cttgc                                                                65
```

```
<210> SEQ ID NO 28
<211> LENGTH: 65
<212> TYPE: DNA
<213> ORGANISM: Artificial
<220> FEATURE:
<223> OTHER INFORMATION: synthetic DNA

<400> SEQUENCE: 28
agatcttgat ccttgtcctc gtccaaaaag acgtcagcct tacaacgcaa tattttctcc      60
aaaag                                                                  65

<210> SEQ ID NO 29
<211> LENGTH: 65
<212> TYPE: DNA
<213> ORGANISM: Artificial
<220> FEATURE:
<223> OTHER INFORMATION: synthetic DNA

<400> SEQUENCE: 29
catctccttg tctgaaaaca tttcccctgc tgttctcttt ctaacatgtt gtggtaaatc      60
tgttc                                                                  65

<210> SEQ ID NO 30
<211> LENGTH: 65
<212> TYPE: DNA
<213> ORGANISM: Artificial
<220> FEATURE:
<223> OTHER INFORMATION: synthetic DNA

<400> SEQUENCE: 30
cctttaattc cttactttgg ctatgggtgg agggtgagtt tgaagaggtt ctgattttct      60
tgtaa                                                                  65

<210> SEQ ID NO 31
<211> LENGTH: 65
<212> TYPE: DNA
<213> ORGANISM: Artificial
<220> FEATURE:
<223> OTHER INFORMATION: synthetic DNA

<400> SEQUENCE: 31
ggttgagaca actgtcacaa gcctcaagac gaaagtaggc ggtacgaacc ctaatggagg      60
cagtt                                                                  65

<210> SEQ ID NO 32
<211> LENGTH: 65
<212> TYPE: DNA
<213> ORGANISM: Artificial
<220> FEATURE:
<223> OTHER INFORMATION: synthetic DNA

<400> SEQUENCE: 32
cttgtgggct tcaggtgttt tcaagcacaa cccaccacaa caagcaagtg cattttcagt      60
cgttg                                                                  65

<210> SEQ ID NO 33
<211> LENGTH: 65
<212> TYPE: DNA
<213> ORGANISM: Artificial
<220> FEATURE:
<223> OTHER INFORMATION: synthetic DNA

<400> SEQUENCE: 33
aggagtgaat gtaaaaataa atatcgctta gaatgcagga gaagggtgga gaggaggcag      60
```

```
gggcc                                                              65

<210> SEQ ID NO 34
<211> LENGTH: 65
<212> TYPE: DNA
<213> ORGANISM: Artificial
<220> FEATURE:
<223> OTHER INFORMATION: synthetic DNA

<400> SEQUENCE: 34
gtgaaattgt gccttgcctg agtgagcttc ataaagcgta ccttgatata ccccatcgac    60
ctcag                                                              65

<210> SEQ ID NO 35
<211> LENGTH: 65
<212> TYPE: DNA
<213> ORGANISM: Artificial
<220> FEATURE:
<223> OTHER INFORMATION: synthetic DNA

<400> SEQUENCE: 35
acctgaggca gtatgacatc tctgacccac agagaccccg cctcacagga cagctcttcc    60
tcgga                                                              65

<210> SEQ ID NO 36
<211> LENGTH: 65
<212> TYPE: DNA
<213> ORGANISM: Artificial
<220> FEATURE:
<223> OTHER INFORMATION: synthetic DNA

<400> SEQUENCE: 36
ttctcccagc gttaacacaa aatccatggg cagcatgatg gcaggtcctc tgttgcaaac    60
tcagt                                                              65

<210> SEQ ID NO 37
<211> LENGTH: 65
<212> TYPE: DNA
<213> ORGANISM: Artificial
<220> FEATURE:
<223> OTHER INFORMATION: synthetic DNA

<400> SEQUENCE: 37
cccagaccaa aatgagtgcc agcgacccaa actcctccat cttcctcacc gacacggcca    60
agcag                                                              65

<210> SEQ ID NO 38
<211> LENGTH: 65
<212> TYPE: DNA
<213> ORGANISM: Artificial
<220> FEATURE:
<223> OTHER INFORMATION: synthetic DNA

<400> SEQUENCE: 38
ccaaattgcc aaaactcaag tcacctcagt accatccagg aggctgggta ttgtcctgcc    60
tctgc                                                              65

<210> SEQ ID NO 39
<211> LENGTH: 65
<212> TYPE: DNA
<213> ORGANISM: Artificial
<220> FEATURE:
<223> OTHER INFORMATION: synthetic DNA
```

<400> SEQUENCE: 39
gcttgcagca tggtcttgac tgaatgtact gttcctgtta gcgttacttc tcctgtggtc    60
agtaa    65

<210> SEQ ID NO 40
<211> LENGTH: 65
<212> TYPE: DNA
<213> ORGANISM: Artificial
<220> FEATURE:
<223> OTHER INFORMATION: synthetic DNA

<400> SEQUENCE: 40
gctgggaact gacataggct tcaattggtg gaattcctct ttaacaaggg ctgcaatgcc    60
ctcat    65

<210> SEQ ID NO 41
<211> LENGTH: 65
<212> TYPE: DNA
<213> ORGANISM: Artificial
<220> FEATURE:
<223> OTHER INFORMATION: synthetic DNA

<400> SEQUENCE: 41
aggaaggagc cttggatctc agcggcctca gagctataga caccactcag ctgttctccc    60
tcccc    65

<210> SEQ ID NO 42
<211> LENGTH: 65
<212> TYPE: DNA
<213> ORGANISM: Artificial
<220> FEATURE:
<223> OTHER INFORMATION: synthetic DNA

<400> SEQUENCE: 42
aagggtgcca tggcagctac atattctgct ttgaaccgta atcagtcacc agttttggaa    60
ccagt    65

<210> SEQ ID NO 43
<211> LENGTH: 65
<212> TYPE: DNA
<213> ORGANISM: Artificial
<220> FEATURE:
<223> OTHER INFORMATION: synthetic DNA

<400> SEQUENCE: 43
gctttatgta aatattctgc agttgttact taggaagcct ggggagggca ggggtgcccc    60
atggc    65

<210> SEQ ID NO 44
<211> LENGTH: 65
<212> TYPE: DNA
<213> ORGANISM: Artificial
<220> FEATURE:
<223> OTHER INFORMATION: synthetic DNA

<400> SEQUENCE: 44
gttgatgcaa tcggtttaaa catggctgaa cgcgtgtgta cacgggactg acgcaaccca    60
cgtgt    65

<210> SEQ ID NO 45
<211> LENGTH: 65

```
<212> TYPE: DNA
<213> ORGANISM: Artificial
<220> FEATURE:
<223> OTHER INFORMATION: synthetic DNA

<400> SEQUENCE: 45
cttcagagag ctggtagtta gtagcatgtt gagccaggcc tgggtctgtg tctctttct      60 ctttc                                                                 65

<210> SEQ ID NO 46
<211> LENGTH: 65
<212> TYPE: DNA
<213> ORGANISM: Artificial
<220> FEATURE:
<223> OTHER INFORMATION: synthetic DNA

<400> SEQUENCE: 46
gcttaaggac tcagaaacaa gtcagcgtct ggccaacctc aggcaacggg tggagcagtt      60
tgcca                                                                 65

<210> SEQ ID NO 47
<211> LENGTH: 65
<212> TYPE: DNA
<213> ORGANISM: Artificial
<220> FEATURE:
<223> OTHER INFORMATION: synthetic DNA

<400> SEQUENCE: 47
acttcaagat caccctctac gggagaacca aggagctgac ttcggaacta aaggagaact      60
tcatc                                                                 65

<210> SEQ ID NO 48
<211> LENGTH: 65
<212> TYPE: DNA
<213> ORGANISM: Artificial
<220> FEATURE:
<223> OTHER INFORMATION: synthetic DNA

<400> SEQUENCE: 48
cactggtttc aagaatatgg aggctggaag gaaataaaca ttacggtaca gacatggaga      60
tgtaa                                                                 65

<210> SEQ ID NO 49
<211> LENGTH: 65
<212> TYPE: DNA
<213> ORGANISM: Artificial
<220> FEATURE:
<223> OTHER INFORMATION: synthetic DNA

<400> SEQUENCE: 49
tgccgtggat aaattgctca aggacctgga cgccaatgga gatgcccagg tggacttcag      60
tgagt                                                                 65

<210> SEQ ID NO 50
<211> LENGTH: 65
<212> TYPE: DNA
<213> ORGANISM: Artificial
<220> FEATURE:
<223> OTHER INFORMATION: synthetic DNA

<400> SEQUENCE: 50
tgctcctatt ccggactcag acctctgacc ctgcaatgct gcctaccatg attggcctcc      60
tggca                                                                 65
```

<210> SEQ ID NO 51
<211> LENGTH: 65
<212> TYPE: DNA
<213> ORGANISM: Artificial
<220> FEATURE:
<223> OTHER INFORMATION: synthetic DNA

<400> SEQUENCE: 51
aaaacaaact tggcttgata atcatttggg cagcttgggt aagtacgcaa cttactttc      60 cacca                                                                 65

<210> SEQ ID NO 52
<211> LENGTH: 65
<212> TYPE: DNA
<213> ORGANISM: Artificial
<220> FEATURE:
<223> OTHER INFORMATION: synthetic DNA

<400> SEQUENCE: 52
cccaaaatgc tctgtcttga gtcatgagaa ccatcagttc ttgatattgt ctagacttgc      60
atcta                                                                 65

<210> SEQ ID NO 53
<211> LENGTH: 65
<212> TYPE: DNA
<213> ORGANISM: Artificial
<220> FEATURE:
<223> OTHER INFORMATION: synthetic DNA

<400> SEQUENCE: 53
gaatactttg gcttgaagcc ggcacaccca gggttactga ggacttatgc tgcctgacct      60
ggtta                                                                 65

<210> SEQ ID NO 54
<211> LENGTH: 65
<212> TYPE: DNA
<213> ORGANISM: Artificial
<220> FEATURE:
<223> OTHER INFORMATION: synthetic DNA

<400> SEQUENCE: 54
cccagatctt caatgaggag cagtactgtg gggattttga ctctttcttc tctgcaaaag      60
aagag                                                                 65

<210> SEQ ID NO 55
<211> LENGTH: 65
<212> TYPE: DNA
<213> ORGANISM: Artificial
<220> FEATURE:
<223> OTHER INFORMATION: synthetic DNA

<400> SEQUENCE: 55 gacccctaa gttagtcaga ttactagaca gatataaaca gatcccctgc tgaacagata       60
tacag                                                                 65

<210> SEQ ID NO 56
<211> LENGTH: 65
<212> TYPE: DNA
<213> ORGANISM: Artificial
<220> FEATURE:
<223> OTHER INFORMATION: synthetic DNA

<400> SEQUENCE: 56

```
ccaaggagaa aggcatgaat cttccctgtc aggctcttac agccacaggc actgtgtcta    60
ctgtc                                                                65

<210> SEQ ID NO 57
<211> LENGTH: 65
<212> TYPE: DNA
<213> ORGANISM: Artificial
<220> FEATURE:
<223> OTHER INFORMATION: synthetic DNA

<400> SEQUENCE: 57
ggaggcagcc atcataacca ttgaatagca tgcaagggta agaatgagtt tttaactgct    60
ttgta                                                                65

<210> SEQ ID NO 58
<211> LENGTH: 65
<212> TYPE: DNA
<213> ORGANISM: Artificial
<220> FEATURE:
<223> OTHER INFORMATION: synthetic DNA

<400> SEQUENCE: 58
gcacaccttg gaattcgctt tctaaaggaa atcaaatgaa tggaggaact ttccaaacac    60
cactt                                                                65

<210> SEQ ID NO 59
<211> LENGTH: 65
<212> TYPE: DNA
<213> ORGANISM: Artificial
<220> FEATURE:
<223> OTHER INFORMATION: synthetic DNA

<400> SEQUENCE: 59
gccactgcag ctaccgtaga atggcatttt atatgtacct tgtcacccac ttctgtttac    60
ttttt                                                                65

<210> SEQ ID NO 60
<211> LENGTH: 65
<212> TYPE: DNA
<213> ORGANISM: Artificial
<220> FEATURE:
<223> OTHER INFORMATION: synthetic DNA

<400> SEQUENCE: 60
ggcctcctca atttgcagat cccccaagta caggcgctaa ttgttgtgat aatttgtaat    60
tgtga                                                                65

<210> SEQ ID NO 61
<211> LENGTH: 65
<212> TYPE: DNA
<213> ORGANISM: Artificial
<220> FEATURE:
<223> OTHER INFORMATION: synthetic DNA

<400> SEQUENCE: 61
tcagcggctg ttgattcaag gtcaacattg accattggag gagtggttta agagtgccag    60
gcgaa                                                                65

<210> SEQ ID NO 62
<211> LENGTH: 65
<212> TYPE: DNA
<213> ORGANISM: Artificial
```

```
-continued

<220> FEATURE:
<223> OTHER INFORMATION: synthetic DNA

<400> SEQUENCE: 62
gaaggatatt actaccgtca agtctttgaa cgccattacc caggccgggc tgactggctg    60
agcca                                                                65

<210> SEQ ID NO 63
<211> LENGTH: 65
<212> TYPE: DNA
<213> ORGANISM: Artificial
<220> FEATURE:
<223> OTHER INFORMATION: synthetic DNA

<400> SEQUENCE: 63
ctacattata actcacagca ttgttccatt gcaggttttg caatgtttgg gggtaaagac    60
agtag                                                                65

<210> SEQ ID NO 64
<211> LENGTH: 65
<212> TYPE: DNA
<213> ORGANISM: Artificial
<220> FEATURE:
<223> OTHER INFORMATION: synthetic DNA

<400> SEQUENCE: 64
cttttattta agttgtgatt acctgctgca tgaaaagtgg catgggggac cctgtgcatc    60
tgtgc                                                                65

<210> SEQ ID NO 65
<211> LENGTH: 65
<212> TYPE: DNA
<213> ORGANISM: Artificial
<220> FEATURE:
<223> OTHER INFORMATION: synthetic DNA

<400> SEQUENCE: 65
gatatcgaag agcagggggt tgtgaatttc caggtacttg acttttttgt agaaggagag    60
agaag                                                                65

<210> SEQ ID NO 66
<211> LENGTH: 65
<212> TYPE: DNA
<213> ORGANISM: Artificial
<220> FEATURE:
<223> OTHER INFORMATION: synthetic DNA

<400> SEQUENCE: 66
ccagaatcgc tagactaaga attaggtggc tacagatggt agaactaaac aataagcaag    60
agaca                                                                65

<210> SEQ ID NO 67
<211> LENGTH: 65
<212> TYPE: DNA
<213> ORGANISM: Artificial
<220> FEATURE:
<223> OTHER INFORMATION: synthetic DNA

<400> SEQUENCE: 67
gaaatggctt ctatgatcag aactgggaaa acagtgaatc ttatggtgga agaggttctc    60
agcaa                                                                65
```

```
<210> SEQ ID NO 68
<211> LENGTH: 65
<212> TYPE: DNA
<213> ORGANISM: Artificial
<220> FEATURE:
<223> OTHER INFORMATION: synthetic DNA

<400> SEQUENCE: 68
gcaatcacaa tgccagatgg tgtttatggg ctatttgtgt aagtaagtgg taagatgcta    60
tgaag                                                                65

<210> SEQ ID NO 69
<211> LENGTH: 65
<212> TYPE: DNA
<213> ORGANISM: Artificial
<220> FEATURE:
<223> OTHER INFORMATION: synthetic DNA

<400> SEQUENCE: 69
ggaagattcc cggagggaaa ctgtgaatgc ttctgattta gcaatgctgt gaataaaaag    60
aaaga                                                                65

<210> SEQ ID NO 70
<211> LENGTH: 65
<212> TYPE: DNA
<213> ORGANISM: Artificial
<220> FEATURE:
<223> OTHER INFORMATION: synthetic DNA

<400> SEQUENCE: 70
acctacggca acagatacaa gaacgtgaag ctccctgacg cctacgagcg cctcatcctg    60
gacgt                                                                65

<210> SEQ ID NO 71
<211> LENGTH: 65
<212> TYPE: DNA
<213> ORGANISM: Artificial
<220> FEATURE:
<223> OTHER INFORMATION: synthetic DNA

<400> SEQUENCE: 71
gcttctaggc ggactatgac ttagttgcgt tacacccttt cttgacaaaa cctaacttgc    60
gcaga                                                                65

<210> SEQ ID NO 72
<211> LENGTH: 65
<212> TYPE: DNA
<213> ORGANISM: Artificial
<220> FEATURE:
<223> OTHER INFORMATION: synthetic DNA

<400> SEQUENCE: 72
acggaggagc atgcccgaca gcagcacaat gagaggctac gcaagcagtt tggagcccag    60
gccaa                                                                65

<210> SEQ ID NO 73
<211> LENGTH: 65
<212> TYPE: DNA
<213> ORGANISM: Artificial
<220> FEATURE:
<223> OTHER INFORMATION: synthetic DNA

<400> SEQUENCE: 73
agagtgcctt ttcgagactg gcagggacga ggacaaatat ggatgaggtg gagagtggga    60
``` agcag 65

<210> SEQ ID NO 74
<211> LENGTH: 65
<212> TYPE: DNA
<213> ORGANISM: Artificial
<220> FEATURE:
<223> OTHER INFORMATION: synthetic DNA

<400> SEQUENCE: 74
acactgttgc cctggctgta ttcataagat tccagctcct tcaggtgttt gattccagca    60
tgtag                                                                65

<210> SEQ ID NO 75
<211> LENGTH: 65
<212> TYPE: DNA
<213> ORGANISM: Artificial
<220> FEATURE:
<223> OTHER INFORMATION: synthetic DNA

<400> SEQUENCE: 75
attgaggctc ttggaaggag tcaggcaagg attgtgcttc ccccattata caggtgacaa    60
aactg                                                                65

<210> SEQ ID NO 76
<211> LENGTH: 65
<212> TYPE: DNA
<213> ORGANISM: Artificial
<220> FEATURE:
<223> OTHER INFORMATION: synthetic DNA

<400> SEQUENCE: 76
attcaagcgc acgagtgggt gccgctgtgg ctactgcggt attcggtcat tgtgaaaagt    60
agagg                                                                65

<210> SEQ ID NO 77
<211> LENGTH: 65
<212> TYPE: DNA
<213> ORGANISM: Artificial
<220> FEATURE:
<223> OTHER INFORMATION: synthetic DNA

<400> SEQUENCE: 77
tgtgactttc aagctactca ccctgtaatg gatcttaaag cattccccaa agataacatg    60
cttttg                                                               65

<210> SEQ ID NO 78
<211> LENGTH: 65
<212> TYPE: DNA
<213> ORGANISM: Artificial
<220> FEATURE:
<223> OTHER INFORMATION: synthetic DNA

<400> SEQUENCE: 78
attcatcaat tatgtgaaga attgcttccg gatgactgac caagaggcta ttcaagatct    60
ctggc                                                                65

<210> SEQ ID NO 79
<211> LENGTH: 65
<212> TYPE: DNA
<213> ORGANISM: Artificial
<220> FEATURE:
<223> OTHER INFORMATION: synthetic DNA

```
<400> SEQUENCE: 79
tatccaagtt gtccttgaat tgtctaacca tggacataaa cagttgtctc ccttctactg    60
tgtag                                                                65

<210> SEQ ID NO 80
<211> LENGTH: 65
<212> TYPE: DNA
<213> ORGANISM: Artificial
<220> FEATURE:
<223> OTHER INFORMATION: synthetic DNA

<400> SEQUENCE: 80
ggaaaacagc cagaagccac cttgacactt ttgaacattt ccagttctgt agagtttatt    60
gtcaa                                                                65

<210> SEQ ID NO 81
<211> LENGTH: 65
<212> TYPE: DNA
<213> ORGANISM: Artificial
<220> FEATURE:
<223> OTHER INFORMATION: synthetic DNA

<400> SEQUENCE: 81
ggtgggaggt gggatttagc caggaaaggg gtgagagtga ttgtgttgtg ggcgaggagg    60
cgttt                                                                65

<210> SEQ ID NO 82
<211> LENGTH: 65
<212> TYPE: DNA
<213> ORGANISM: Artificial
<220> FEATURE:
<223> OTHER INFORMATION: synthetic DNA

<400> SEQUENCE: 82
attgtggggg tcgatcatga atgtccgaag agtggccttt tcccgtagcc ctgcgccccc    60
tttct                                                                65

<210> SEQ ID NO 83
<211> LENGTH: 65
<212> TYPE: DNA
<213> ORGANISM: Artificial
<220> FEATURE:
<223> OTHER INFORMATION: synthetic DNA

<400> SEQUENCE: 83
ttgtgcagca atggccaaga tcaaggctcg agatcttcgc gggaagaaga aggaggagct    60
gctga                                                                65

<210> SEQ ID NO 84
<211> LENGTH: 65
<212> TYPE: DNA
<213> ORGANISM: Artificial
<220> FEATURE:
<223> OTHER INFORMATION: synthetic DNA

<400> SEQUENCE: 84
aagcaaagag aagactttgt acacactgtc accagggtta tttgcatcca agggagctgg    60
aattg                                                                65

<210> SEQ ID NO 85
<211> LENGTH: 65
```

<212> TYPE: DNA
<213> ORGANISM: Artificial
<220> FEATURE:
<223> OTHER INFORMATION: synthetic DNA

<400> SEQUENCE: 85
cgtgcccgaa atcaggtggt gataagagca gagccccaac tctgtgcctt gtgtgcggat    60
ctctg    65

<210> SEQ ID NO 86
<211> LENGTH: 65
<212> TYPE: DNA
<213> ORGANISM: Artificial
<220> FEATURE:
<223> OTHER INFORMATION: synthetic DNA

<400> SEQUENCE: 86
tctagaactg acctaccaca agcatccacc aaaggagttt gggattgagt tttgctgctg    60
tgcag    65

<210> SEQ ID NO 87
<211> LENGTH: 65
<212> TYPE: DNA
<213> ORGANISM: Artificial
<220> FEATURE:
<223> OTHER INFORMATION: synthetic DNA

<400> SEQUENCE: 87
ggtctcttcc agattgctct tctgccgaat tatttgtatc tattccgagc tgattatgta    60
atagg    65

<210> SEQ ID NO 88
<211> LENGTH: 65
<212> TYPE: DNA
<213> ORGANISM: Artificial
<220> FEATURE:
<223> OTHER INFORMATION: synthetic DNA

<400> SEQUENCE: 88
gctcttgatg agaggctcgc tttaaagaag cccaaagcgt gtgcttatcc aaggggttca    60
gctat    65

<210> SEQ ID NO 89
<211> LENGTH: 65
<212> TYPE: DNA
<213> ORGANISM: Artificial
<220> FEATURE:
<223> OTHER INFORMATION: synthetic DNA

<400> SEQUENCE: 89
ctgcttcata ggtgttctgc atttgaggtg tagtgaaatc tttgctgttc accagatgta    60
atgtt    65

<210> SEQ ID NO 90
<211> LENGTH: 65
<212> TYPE: DNA
<213> ORGANISM: Artificial
<220> FEATURE:
<223> OTHER INFORMATION: synthetic DNA

<400> SEQUENCE: 90
tgaagtagta gccacagtac aacactgact gctcagacac atttaggttc agggtggacc    60
tttat    65

```
<210> SEQ ID NO 91
<211> LENGTH: 65
<212> TYPE: DNA
<213> ORGANISM: Artificial
<220> FEATURE:
<223> OTHER INFORMATION: synthetic DNA

<400> SEQUENCE: 91
ttgtggtgag acgtcatagt cttcatgaga acgtgggggt gaatttcatg aaggggaact    60
atagt                                                                65

<210> SEQ ID NO 92
<211> LENGTH: 65
<212> TYPE: DNA
<213> ORGANISM: Artificial
<220> FEATURE:
<223> OTHER INFORMATION: synthetic DNA

<400> SEQUENCE: 92
gactctatcg tggtttatct cttaattaca ttcgctgtat tccctctcaa gcagtggctt    60
ttaca                                                                65

<210> SEQ ID NO 93
<211> LENGTH: 65
<212> TYPE: DNA
<213> ORGANISM: Artificial
<220> FEATURE:
<223> OTHER INFORMATION: synthetic DNA

<400> SEQUENCE: 93
gaagtcgaga tgactttgat cattggtaac ttgggcctgg gccagacaaa gtataaaact    60
tacaa                                                                65

<210> SEQ ID NO 94
<211> LENGTH: 65
<212> TYPE: DNA
<213> ORGANISM: Artificial
<220> FEATURE:
<223> OTHER INFORMATION: synthetic DNA

<400> SEQUENCE: 94
tctgtctata cctgccccat ctgagcaccc attgctcacc atcagatcaa cctttgattt    60
tacat                                                                65

<210> SEQ ID NO 95
<211> LENGTH: 65
<212> TYPE: DNA
<213> ORGANISM: Artificial
<220> FEATURE:
<223> OTHER INFORMATION: synthetic DNA

<400> SEQUENCE: 95
ccagtttctg tatagaatcg cacaagtggt ttatggagtg tttggattgt aattataaat    60
ggttc                                                                65

<210> SEQ ID NO 96
<211> LENGTH: 65
<212> TYPE: DNA
<213> ORGANISM: Artificial
<220> FEATURE:
<223> OTHER INFORMATION: synthetic DNA

<400> SEQUENCE: 96
```

```
ctagcctgca ttgagcttgc atgcttgcat aagagcttaa gaaccattga tttaatgtaa      60
taggg                                                                  65

<210> SEQ ID NO 97
<211> LENGTH: 65
<212> TYPE: DNA
<213> ORGANISM: Artificial
<220> FEATURE:
<223> OTHER INFORMATION: synthetic DNA

<400> SEQUENCE: 97
gcctgcatcc ggagaattgc ctctacctgg accttttgtc tcacacagca gtaccctgac      60
ctgct                                                                  65

<210> SEQ ID NO 98
<211> LENGTH: 65
<212> TYPE: DNA
<213> ORGANISM: Artificial
<220> FEATURE:
<223> OTHER INFORMATION: synthetic DNA

<400> SEQUENCE: 98
cctcacaccc accccatgc actcaaagat tggattttac agctacttgc aattcaaaat       60
tcaga                                                                  65

<210> SEQ ID NO 99
<211> LENGTH: 65
<212> TYPE: DNA
<213> ORGANISM: Artificial
<220> FEATURE:
<223> OTHER INFORMATION: synthetic DNA

<400> SEQUENCE: 99
gggccatctc ttggagtgac aaagctggga tcaaggatag ggagttgtaa cagagcagtg      60
ccaga                                                                  65

<210> SEQ ID NO 100
<211> LENGTH: 65
<212> TYPE: DNA
<213> ORGANISM: Artificial
<220> FEATURE:
<223> OTHER INFORMATION: synthetic DNA

<400> SEQUENCE: 100
gcctgaacta gccaatcaga tcaactctgt cttgggcgtt tgaactcagg gagggaggcc      60
cttgg                                                                  65

<210> SEQ ID NO 101
<211> LENGTH: 65
<212> TYPE: DNA
<213> ORGANISM: Artificial
<220> FEATURE:
<223> OTHER INFORMATION: synthetic DNA

<400> SEQUENCE: 101
ctgacaagtc ttaatcaact aggcgagagg caacttcttt cagtagtcaa gtggtctaaa      60
tcatt                                                                  65

<210> SEQ ID NO 102
<211> LENGTH: 65
<212> TYPE: DNA
<213> ORGANISM: Artificial
```

```
<220> FEATURE:
<223> OTHER INFORMATION: synthetic DNA

<400> SEQUENCE: 102
caagttcagc tccacgtgtg ccatcagtgg atccgatccg tccagccatg gcttcctatt    60
ccaag                                                                65

<210> SEQ ID NO 103
<211> LENGTH: 65
<212> TYPE: DNA
<213> ORGANISM: Artificial
<220> FEATURE:
<223> OTHER INFORMATION: synthetic DNA

<400> SEQUENCE: 103
gcaagtgtac agatctgtgt agaggaatgt gtgtatattt acctcttcgt ttgctcaaac    60
atgag                                                                65

<210> SEQ ID NO 104
<211> LENGTH: 65
<212> TYPE: DNA
<213> ORGANISM: Artificial
<220> FEATURE:
<223> OTHER INFORMATION: synthetic DNA

<400> SEQUENCE: 104
ctgaccctga agttttccta ccccaaggag agttactcga cagtccataa gtcaactgtt    60
gtgtg                                                                65

<210> SEQ ID NO 105
<211> LENGTH: 65
<212> TYPE: DNA
<213> ORGANISM: Artificial
<220> FEATURE:
<223> OTHER INFORMATION: synthetic DNA

<400> SEQUENCE: 105
tcacttgctg aacgccgtga ccgatgcttt ggtttgggtg attgccaaga gcggcatctc    60
ctccc                                                                65

<210> SEQ ID NO 106
<211> LENGTH: 65
<212> TYPE: DNA
<213> ORGANISM: Artificial
<220> FEATURE:
<223> OTHER INFORMATION: synthetic DNA

<400> SEQUENCE: 106
ctgttgtcct cccctgggc ggctgagagc cccagctgac atggaaatac agttgttggc    60
ctccg                                                                65

<210> SEQ ID NO 107
<211> LENGTH: 65
<212> TYPE: DNA
<213> ORGANISM: Artificial
<220> FEATURE:
<223> OTHER INFORMATION: synthetic DNA

<400> SEQUENCE: 107
caaaaatgac ccccatttgt gtgacttcat tgagacacat tacctgaatg agcaggtgaa    60
agcca                                                                65
```

```
<210> SEQ ID NO 108
<211> LENGTH: 65
<212> TYPE: DNA
<213> ORGANISM: Artificial
<220> FEATURE:
<223> OTHER INFORMATION: synthetic DNA

<400> SEQUENCE: 108
ggcctgggta ggatcatgta tacggtattt gaacatacat tccatgtacg agaaggagat    60
gaaca                                                                65

<210> SEQ ID NO 109
<211> LENGTH: 65
<212> TYPE: DNA
<213> ORGANISM: Artificial
<220> FEATURE:
<223> OTHER INFORMATION: synthetic DNA

<400> SEQUENCE: 109
gctattattt tctttaaaga atgctgggtg ttgcatttct ggaccctcca cttcaatctg    60
agaag                                                                65

<210> SEQ ID NO 110
<211> LENGTH: 65
<212> TYPE: DNA
<213> ORGANISM: Artificial
<220> FEATURE:
<223> OTHER INFORMATION: synthetic DNA

<400> SEQUENCE: 110
ctctttctgc atggttgtgt ccctagtcct aagctttggt tctttagggt gactgtggta    60
agaag                                                                65

<210> SEQ ID NO 111
<211> LENGTH: 65
<212> TYPE: DNA
<213> ORGANISM: Artificial
<220> FEATURE:
<223> OTHER INFORMATION: synthetic DNA

<400> SEQUENCE: 111
attgcgaaga acctgctctc cgcgcctctc ggtgctccaa atggacatca cgaagccagt    60
gcaga                                                                65

<210> SEQ ID NO 112
<211> LENGTH: 65
<212> TYPE: DNA
<213> ORGANISM: Artificial
<220> FEATURE:
<223> OTHER INFORMATION: synthetic DNA

<400> SEQUENCE: 112
tcatgctaac gcagcagttg caaacatttt gaagagagac cgtcggggc tgaggggcaa     60 cgaag                                                                65

<210> SEQ ID NO 113
<211> LENGTH: 65
<212> TYPE: DNA
<213> ORGANISM: Artificial
<220> FEATURE:
<223> OTHER INFORMATION: synthetic DNA

<400> SEQUENCE: 113
gacacgtgat gggaagctgg tgtctgagtc ctctgacgtc ctgcccaagt gaacagctgc    60
```

```
<210> SEQ ID NO 114
<211> LENGTH: 65
<212> TYPE: DNA
<213> ORGANISM: Artificial
<220> FEATURE:
<223> OTHER INFORMATION: synthetic DNA

<400> SEQUENCE: 114
tctgtatgac aacccgggat cgtttgcaag taactgaatc cattgcgaca ttgtgaaggc    60
ttaaa                                                               65

<210> SEQ ID NO 115
<211> LENGTH: 65
<212> TYPE: DNA
<213> ORGANISM: Artificial
<220> FEATURE:
<223> OTHER INFORMATION: synthetic DNA

<400> SEQUENCE: 115
tgctgtgttt actctcccgt gtgccttcgc gtccgggttg ggagcttgct gtgtctaacc    60
tccaa                                                               65

<210> SEQ ID NO 116
<211> LENGTH: 65
<212> TYPE: DNA
<213> ORGANISM: Artificial
<220> FEATURE:
<223> OTHER INFORMATION: synthetic DNA

<400> SEQUENCE: 116
ttgtatcacg gattacaatg aacgcagtgc agagccccaa agctcaggct attgttaaat    60
caata                                                               65

<210> SEQ ID NO 117
<211> LENGTH: 65
<212> TYPE: DNA
<213> ORGANISM: Artificial
<220> FEATURE:
<223> OTHER INFORMATION: synthetic DNA

<400> SEQUENCE: 117
gcctacatga cacagttgga tttattctgc caaacctgtg taggcatttt ataagctaca    60
tgttc                                                               65

<210> SEQ ID NO 118
<211> LENGTH: 65
<212> TYPE: DNA
<213> ORGANISM: Artificial
<220> FEATURE:
<223> OTHER INFORMATION: synthetic DNA

<400> SEQUENCE: 118
tagtggggac tagtgaatga cttgacctgt gacctcaata caataaatgt gatcccccac    60
ccaaa                                                               65

<210> SEQ ID NO 119
<211> LENGTH: 65
<212> TYPE: DNA
<213> ORGANISM: Artificial
<220> FEATURE:
<223> OTHER INFORMATION: synthetic DNA
```

<400> SEQUENCE: 119
cagcacaagg aggatgtgat atgtggggga gtgagcactg ggttgggagc cgggtcctgg    60
tttcc    65

<210> SEQ ID NO 120
<211> LENGTH: 65
<212> TYPE: DNA
<213> ORGANISM: Artificial
<220> FEATURE:
<223> OTHER INFORMATION: synthetic DNA

<400> SEQUENCE: 120
cactgttaga tagttggaaa ggggaaattc tgtttaagcg aaagtggtat catcctaggt    60
aagct    65

<210> SEQ ID NO 121
<211> LENGTH: 65
<212> TYPE: DNA
<213> ORGANISM: Artificial
<220> FEATURE:
<223> OTHER INFORMATION: synthetic DNA

<400> SEQUENCE: 121
cttccaagct ctgcttcctc agtttccaaa atggaaccac ctcacctccg cagcacccga    60
cttac    65

<210> SEQ ID NO 122
<211> LENGTH: 65
<212> TYPE: DNA
<213> ORGANISM: Artificial
<220> FEATURE:
<223> OTHER INFORMATION: synthetic DNA

<400> SEQUENCE: 122
cccctttgcc attgatcaag ccatattcag gtcctaggtt gccacctgat agatactgct    60
taaca    65

<210> SEQ ID NO 123
<211> LENGTH: 65
<212> TYPE: DNA
<213> ORGANISM: Artificial
<220> FEATURE:
<223> OTHER INFORMATION: synthetic DNA

<400> SEQUENCE: 123
cgacgacacc gttcgtgggg tccctggtg cttctatcct aataccatcg acgtccctcc    60
agaag    65

<210> SEQ ID NO 124
<211> LENGTH: 65
<212> TYPE: DNA
<213> ORGANISM: Artificial
<220> FEATURE:
<223> OTHER INFORMATION: synthetic DNA

<400> SEQUENCE: 124
tttgggagag acttgttttg gatgccccct aatccccttc tccctgcac tgtaaaatgt    60 gggat    65

<210> SEQ ID NO 125
<211> LENGTH: 65

```
<212> TYPE: DNA
<213> ORGANISM: Artificial
<220> FEATURE:
<223> OTHER INFORMATION: synthetic DNA

<400> SEQUENCE: 125
gcctcccttg gtctgcccag ccctcggtta gccctgcctg aatcagtaga tacttgaacg    60
agtcc                                                                65

<210> SEQ ID NO 126
<211> LENGTH: 65
<212> TYPE: DNA
<213> ORGANISM: Artificial
<220> FEATURE:
<223> OTHER INFORMATION: synthetic DNA

<400> SEQUENCE: 126
ctgcgcccct agctgggatc tggtacctgg actaggctaa ttacagcttc tccccaacag    60
gaaac                                                                65

<210> SEQ ID NO 127
<211> LENGTH: 65
<212> TYPE: DNA
<213> ORGANISM: Artificial
<220> FEATURE:
<223> OTHER INFORMATION: synthetic DNA

<400> SEQUENCE: 127
aactcctgta cttgaagctg agacctcata tgacgtggcc ttcgtgttgt cagagagtgt    60
ctgga                                                                65

<210> SEQ ID NO 128
<211> LENGTH: 65
<212> TYPE: DNA
<213> ORGANISM: Artificial
<220> FEATURE:
<223> OTHER INFORMATION: synthetic DNA

<400> SEQUENCE: 128
ctgagagggg aagcggccct aagggagtgt ctaagaacaa aagcgaccca ttcagagact    60
gtccc                                                                65

<210> SEQ ID NO 129
<211> LENGTH: 65
<212> TYPE: DNA
<213> ORGANISM: Artificial
<220> FEATURE:
<223> OTHER INFORMATION: synthetic DNA

<400> SEQUENCE: 129
tgcatgaatg aagaccctgc aaagcgaccc aaatttgaca tgattgtgcc tatccttgag    60
aagat                                                                65

<210> SEQ ID NO 130
<211> LENGTH: 65
<212> TYPE: DNA
<213> ORGANISM: Artificial
<220> FEATURE:
<223> OTHER INFORMATION: synthetic DNA

<400> SEQUENCE: 130
acagctgtag caactttgtg tctgaagatg actcggaaac ccagtccgtg tccagcttta    60
gttca                                                                65
```

<210> SEQ ID NO 131
<211> LENGTH: 65
<212> TYPE: DNA
<213> ORGANISM: Artificial
<220> FEATURE:
<223> OTHER INFORMATION: synthetic DNA

<400> SEQUENCE: 131
tgccctgtgg aatgggctca aggttcctga gacacccgat tcctgcccaa acagctgtat    60
ttata                                                                65

<210> SEQ ID NO 132
<211> LENGTH: 65
<212> TYPE: DNA
<213> ORGANISM: Artificial
<220> FEATURE:
<223> OTHER INFORMATION: synthetic DNA

<400> SEQUENCE: 132
gcagaagcag acctagaccc tagcgttccc ccttatgact ctcttcagac ttatgcctat    60
gaggg                                                                65

<210> SEQ ID NO 133
<211> LENGTH: 65
<212> TYPE: DNA
<213> ORGANISM: Artificial
<220> FEATURE:
<223> OTHER INFORMATION: synthetic DNA

<400> SEQUENCE: 133
ccagacaaaa tttgagaata cataaacaac gcattgccac ggaaacatac agaggatgcc    60
ttttc                                                                65

<210> SEQ ID NO 134
<211> LENGTH: 65
<212> TYPE: DNA
<213> ORGANISM: Artificial
<220> FEATURE:
<223> OTHER INFORMATION: synthetic DNA

<400> SEQUENCE: 134
cagctctaga ggtcacagta tcctcgtttg aaagataatt aagatccccc gtggagaaag    60
cagtg                                                                65

<210> SEQ ID NO 135
<211> LENGTH: 65
<212> TYPE: DNA
<213> ORGANISM: Artificial
<220> FEATURE:
<223> OTHER INFORMATION: synthetic DNA

<400> SEQUENCE: 135
tccaaggctc accgcagaag cagtagcagc ggggaccaat catcagactc cttgaactcc    60
cccac                                                                65

<210> SEQ ID NO 136
<211> LENGTH: 65
<212> TYPE: DNA
<213> ORGANISM: Artificial
<220> FEATURE:
<223> OTHER INFORMATION: synthetic DNA

<400> SEQUENCE: 136

```
ccacatgtta accctctagc tgataatgca aacactaact gggggatttt atttataagg    60
gctct                                                                65

<210> SEQ ID NO 137
<211> LENGTH: 65
<212> TYPE: DNA
<213> ORGANISM: Artificial
<220> FEATURE:
<223> OTHER INFORMATION: synthetic DNA

<400> SEQUENCE: 137
gggcctttcc aagattgctg tttttgtttt ggagcttcaa gactttgcat ttcctagtat    60
ttctg                                                                65

<210> SEQ ID NO 138
<211> LENGTH: 65
<212> TYPE: DNA
<213> ORGANISM: Artificial
<220> FEATURE:
<223> OTHER INFORMATION: synthetic DNA

<400> SEQUENCE: 138
aaactgctat agcctaagcg gctgtttact gcttttcatt agcagttgct cacatgtctt    60
tgggt                                                                65

<210> SEQ ID NO 139
<211> LENGTH: 65
<212> TYPE: DNA
<213> ORGANISM: Artificial
<220> FEATURE:
<223> OTHER INFORMATION: synthetic DNA

<400> SEQUENCE: 139
tgaatgagat gcgtgaccag tacgagcaga tggcagagaa aaaccgcaga gacgctgaga    60
cctgg                                                                65

<210> SEQ ID NO 140
<211> LENGTH: 65
<212> TYPE: DNA
<213> ORGANISM: Artificial
<220> FEATURE:
<223> OTHER INFORMATION: synthetic DNA

<400> SEQUENCE: 140
tgatgctctg cgaagggctc ttcgtggcag acgtcaccga tttcgagggc tggaaggctg    60
cgatt                                                                65

<210> SEQ ID NO 141
<211> LENGTH: 65
<212> TYPE: DNA
<213> ORGANISM: Artificial
<220> FEATURE:
<223> OTHER INFORMATION: synthetic DNA

<400> SEQUENCE: 141
gggggtgctc tttggacact ggattatgag gaatggataa atggatgagc tagggctctg    60
ggggt                                                                65

<210> SEQ ID NO 142
<211> LENGTH: 65
<212> TYPE: DNA
<213> ORGANISM: Artificial
```

```
<220> FEATURE:
<223> OTHER INFORMATION: synthetic DNA

<400> SEQUENCE: 142
tgctgtggct tcaccaacta tacggatttt gaggactcac cctacttcaa agagaacagt    60
gcctt                                                                65

<210> SEQ ID NO 143
<211> LENGTH: 65
<212> TYPE: DNA
<213> ORGANISM: Artificial
<220> FEATURE:
<223> OTHER INFORMATION: synthetic DNA

<400> SEQUENCE: 143
gaggataaca ttggcgggag gggagttaac tggcaggcat ggcaaggttg catatgtaat    60
aaagt                                                                65

<210> SEQ ID NO 144
<211> LENGTH: 65
<212> TYPE: DNA
<213> ORGANISM: Artificial
<220> FEATURE:
<223> OTHER INFORMATION: synthetic DNA

<400> SEQUENCE: 144
tgatgatgag gaagaagaag aagaaggggg ctcatggggc cgtgggaacc caaggttcca    60
tagtc                                                                65

<210> SEQ ID NO 145
<211> LENGTH: 65
<212> TYPE: DNA
<213> ORGANISM: Artificial
<220> FEATURE:
<223> OTHER INFORMATION: synthetic DNA

<400> SEQUENCE: 145
ccaggacaaa ggccgctttg aactctaccg tgccacgttt tatgccgctg agataatgtg    60
tggac                                                                65

<210> SEQ ID NO 146
<211> LENGTH: 65
<212> TYPE: DNA
<213> ORGANISM: Artificial
<220> FEATURE:
<223> OTHER INFORMATION: synthetic DNA

<400> SEQUENCE: 146
tccatttctc tgagggacct ttagttggct ctgtgggact gttccggatg ggcctctggg    60
tcact                                                                65

<210> SEQ ID NO 147
<211> LENGTH: 65
<212> TYPE: DNA
<213> ORGANISM: Artificial
<220> FEATURE:
<223> OTHER INFORMATION: synthetic DNA

<400> SEQUENCE: 147
agcagctgcc taggggtgt ccaaggagca gagaaaacta ctagatgtga acttgaagaa    60
ggttg                                                                65
```

```
<210> SEQ ID NO 148
<211> LENGTH: 65
<212> TYPE: DNA
<213> ORGANISM: Artificial
<220> FEATURE:
<223> OTHER INFORMATION: synthetic DNA

<400> SEQUENCE: 148
gtggttggtg tcctgctcat catcctgatt gtgctgctgg tcgtctttct ccctcagagc    60
agtga                                                                65

<210> SEQ ID NO 149
<211> LENGTH: 65
<212> TYPE: DNA
<213> ORGANISM: Artificial
<220> FEATURE:
<223> OTHER INFORMATION: synthetic DNA

<400> SEQUENCE: 149
aatctgcatt ctgtcaggca cccgtagaaa gacctcagta catgctttgc actctccttt    60
gctcc                                                                65

<210> SEQ ID NO 150
<211> LENGTH: 65
<212> TYPE: DNA
<213> ORGANISM: Artificial
<220> FEATURE:
<223> OTHER INFORMATION: synthetic DNA

<400> SEQUENCE: 150
tacatccagt accaaggctt ccgggtccag ctggaatcca tgaagaagct gagtgacctg    60
gaggc                                                                65

<210> SEQ ID NO 151
<211> LENGTH: 65
<212> TYPE: DNA
<213> ORGANISM: Artificial
<220> FEATURE:
<223> OTHER INFORMATION: synthetic DNA

<400> SEQUENCE: 151
ccaaattcaa gatacaggta tccccgtttt tacaacagat gttcatgccc ctgcttcatg    60
caatt                                                                65

<210> SEQ ID NO 152
<211> LENGTH: 65
<212> TYPE: DNA
<213> ORGANISM: Artificial
<220> FEATURE:
<223> OTHER INFORMATION: synthetic DNA

<400> SEQUENCE: 152
gaattggatt tgaagaactc gactttatgt gatcatggta ttggtataca tgtggggtgg    60
agaac                                                                65

<210> SEQ ID NO 153
<211> LENGTH: 65
<212> TYPE: DNA
<213> ORGANISM: Artificial
<220> FEATURE:
<223> OTHER INFORMATION: synthetic DNA

<400> SEQUENCE: 153
acgattttct tctgtagaat gtttgacttc gtattgaccc ttatctgtaa aacacctatt    60
```

```
tggga                                                              65

<210> SEQ ID NO 154
<211> LENGTH: 65
<212> TYPE: DNA
<213> ORGANISM: Artificial
<220> FEATURE:
<223> OTHER INFORMATION: synthetic DNA

<400> SEQUENCE: 154
gcacgcattt ttgttgcctt ggttttacct gtagactgtg aactattttt accttaagac    60
ctgaa                                                              65

<210> SEQ ID NO 155
<211> LENGTH: 65
<212> TYPE: DNA
<213> ORGANISM: Artificial
<220> FEATURE:
<223> OTHER INFORMATION: synthetic DNA

<400> SEQUENCE: 155
gtggaaggac tgattgagaa tgttccaatc caaatgaatg catcacaact tacaatgctg    60
ctcat                                                              65

<210> SEQ ID NO 156
<211> LENGTH: 65
<212> TYPE: DNA
<213> ORGANISM: Artificial
<220> FEATURE:
<223> OTHER INFORMATION: synthetic DNA

<400> SEQUENCE: 156
gctgctctca ttggaattgc aggatctggc tactgtgtca ttgtggcagc ccttggctta    60
gcaga                                                              65

<210> SEQ ID NO 157
<211> LENGTH: 65
<212> TYPE: DNA
<213> ORGANISM: Artificial
<220> FEATURE:
<223> OTHER INFORMATION: synthetic DNA

<400> SEQUENCE: 157
caaatttaat aaggaaccat gtaatggtag cagtacctcc ctaaagcatt ttgaggtagg    60
ggagg                                                              65

<210> SEQ ID NO 158
<211> LENGTH: 65
<212> TYPE: DNA
<213> ORGANISM: Artificial
<220> FEATURE:
<223> OTHER INFORMATION: synthetic DNA

<400> SEQUENCE: 158
aacaaaaatc tgggaatggt ctgccgaaaa ccgaccgacc cggttgattg gccaccgctt    60
gtcct                                                              65

<210> SEQ ID NO 159
<211> LENGTH: 65
<212> TYPE: DNA
<213> ORGANISM: Artificial
<220> FEATURE:
<223> OTHER INFORMATION: synthetic DNA
```

```
<400> SEQUENCE: 159
tcctaacctg ccggggtcat tccccaccaa acaccccata ctaaggagcc atgagccacc    60
tggac                                                                65

<210> SEQ ID NO 160
<211> LENGTH: 65
<212> TYPE: DNA
<213> ORGANISM: Artificial
<220> FEATURE:
<223> OTHER INFORMATION: synthetic DNA

<400> SEQUENCE: 160
cggagggaac tgcagggaga ccaacttatt tagagcgaat tggacatgga taaaaacccc    60
agtgg                                                                65

<210> SEQ ID NO 161
<211> LENGTH: 65
<212> TYPE: DNA
<213> ORGANISM: Artificial
<220> FEATURE:
<223> OTHER INFORMATION: synthetic DNA

<400> SEQUENCE: 161
tgctgggtac caggactcac ctctgacaag caggagaagg taagggcccg gtcagctcca    60
aggag                                                                65

<210> SEQ ID NO 162
<211> LENGTH: 65
<212> TYPE: DNA
<213> ORGANISM: Artificial
<220> FEATURE:
<223> OTHER INFORMATION: synthetic DNA

<400> SEQUENCE: 162
gccaaaggaa gtctaaggaa ttagtagtgt tcccatcact tgtttggagt gtgctattct    60
aaaag                                                                65

<210> SEQ ID NO 163
<211> LENGTH: 65
<212> TYPE: DNA
<213> ORGANISM: Artificial
<220> FEATURE:
<223> OTHER INFORMATION: synthetic DNA

<400> SEQUENCE: 163
cataaagttg ctggccagct tttacctctt gcatataatc tgttgaagag gaatctgttt    60
gcaga                                                                65

<210> SEQ ID NO 164
<211> LENGTH: 65
<212> TYPE: DNA
<213> ORGANISM: Artificial
<220> FEATURE:
<223> OTHER INFORMATION: synthetic DNA

<400> SEQUENCE: 164
gcaaactcat ggatggctct tataccagga gaagataagg tatgccagag tgtatttgag    60
agaaa                                                                65

<210> SEQ ID NO 165
<211> LENGTH: 65
```

```
<212> TYPE: DNA
<213> ORGANISM: Artificial
<220> FEATURE:
<223> OTHER INFORMATION: synthetic DNA

<400> SEQUENCE: 165
ctgttcagat gatctttcat tcaatgtgtt cctgttgggc gttactagaa actatggaaa    60
actgg                                                                65

<210> SEQ ID NO 166
<211> LENGTH: 65
<212> TYPE: DNA
<213> ORGANISM: Artificial
<220> FEATURE:
<223> OTHER INFORMATION: synthetic DNA

<400> SEQUENCE: 166
tgggtacact ttgtaccagt gtcggcctcc actgatgctg gtgctcaggc acctctgtcc    60
aagga                                                                65

<210> SEQ ID NO 167
<211> LENGTH: 65
<212> TYPE: DNA
<213> ORGANISM: Artificial
<220> FEATURE:
<223> OTHER INFORMATION: synthetic DNA

<400> SEQUENCE: 167
accagggtac cctgtcttgg tggttagggg ccacttttcc tttgaggctc tagtggaggt    60
ggatg                                                                65

<210> SEQ ID NO 168
<211> LENGTH: 65
<212> TYPE: DNA
<213> ORGANISM: Artificial
<220> FEATURE:
<223> OTHER INFORMATION: synthetic DNA

<400> SEQUENCE: 168
ggttgagaag agcttttcgg acctgttact accccaagct gtgtaatata cttgtataac    60
agaaa                                                                65

<210> SEQ ID NO 169
<211> LENGTH: 65
<212> TYPE: DNA
<213> ORGANISM: Artificial
<220> FEATURE:
<223> OTHER INFORMATION: synthetic DNA

<400> SEQUENCE: 169
ctaaggccat tgacgtggcc tgcgatctca gtgacaatga tctgcttctg gatctcactg    60
ttgcc                                                                65

<210> SEQ ID NO 170
<211> LENGTH: 65
<212> TYPE: DNA
<213> ORGANISM: Artificial
<220> FEATURE:
<223> OTHER INFORMATION: synthetic DNA

<400> SEQUENCE: 170
tgacagccac cgggtcatca ccttcgcaaa ccaggacgac tacatatcat tccggcacca    60
tgtgt                                                                65
```

<210> SEQ ID NO 171
<211> LENGTH: 65
<212> TYPE: DNA
<213> ORGANISM: Artificial
<220> FEATURE:
<223> OTHER INFORMATION: synthetic DNA

<400> SEQUENCE: 171
ctccagcatc tcaactccgt ctgtctactg tgtgagactt cggcggacca ttaggaatga    60
gatcc    65

<210> SEQ ID NO 172
<211> LENGTH: 65
<212> TYPE: DNA
<213> ORGANISM: Artificial
<220> FEATURE:
<223> OTHER INFORMATION: synthetic DNA

<400> SEQUENCE: 172
cgattacagg gacaacagca gttgatacac caaaatcggc aagctatctt aaaccagttt    60
gcagc    65

<210> SEQ ID NO 173
<211> LENGTH: 65
<212> TYPE: DNA
<213> ORGANISM: Artificial
<220> FEATURE:
<223> OTHER INFORMATION: synthetic DNA

<400> SEQUENCE: 173
agaaggagca atggtacgct ggcatcaacc cctcggacgg tatcaactca gaggtcctgg    60
aagcc    65

<210> SEQ ID NO 174
<211> LENGTH: 65
<212> TYPE: DNA
<213> ORGANISM: Artificial
<220> FEATURE:
<223> OTHER INFORMATION: synthetic DNA

<400> SEQUENCE: 174
ccccaaagga tggtcacaca ccagcacttt atacattct ggctcacagg aaagtgtctg    60
cagta    65

<210> SEQ ID NO 175
<211> LENGTH: 65
<212> TYPE: DNA
<213> ORGANISM: Artificial
<220> FEATURE:
<223> OTHER INFORMATION: synthetic DNA

<400> SEQUENCE: 175
atgccttgta cccccaccgt gcaggttgtg gccggttttc tccgcaggtt gaacatggaa    60
ataaa    65

<210> SEQ ID NO 176
<211> LENGTH: 65
<212> TYPE: DNA
<213> ORGANISM: Artificial
<220> FEATURE:
<223> OTHER INFORMATION: synthetic DNA

<400> SEQUENCE: 176

```
ttggtgcaag tcttgggagc gtgatctaga ttacactgca ccattcccaa gttaatcccc    60
tgaaa                                                               65
```

<210> SEQ ID NO 177
<211> LENGTH: 65
<212> TYPE: DNA
<213> ORGANISM: Artificial
<220> FEATURE:
<223> OTHER INFORMATION: synthetic DNA

<400> SEQUENCE: 177

```
ttccatccac tgcccatgac cctgttccct gtctataaat ccccagtttt ccatggtata    60
ttcag                                                               65
```

<210> SEQ ID NO 178
<211> LENGTH: 65
<212> TYPE: DNA
<213> ORGANISM: Artificial
<220> FEATURE:
<223> OTHER INFORMATION: synthetic DNA

<400> SEQUENCE: 178

```
gtatattaaa gcaccaaatt catgtacagc atgcatcacg gatcaataga ctgtacttat    60
tttcc                                                               65
```

<210> SEQ ID NO 179
<211> LENGTH: 65
<212> TYPE: DNA
<213> ORGANISM: Artificial
<220> FEATURE:
<223> OTHER INFORMATION: synthetic DNA

<400> SEQUENCE: 179

```
ggcttcggac aaaatatctc tgagttctgt gtattttcag tcaaaacttt aaacctgtag    60
aatca                                                               65
```

<210> SEQ ID NO 180
<211> LENGTH: 65
<212> TYPE: DNA
<213> ORGANISM: Artificial
<220> FEATURE:
<223> OTHER INFORMATION: synthetic DNA

<400> SEQUENCE: 180

```
agtggagctg tttgacttgg agaataaccc agagtacgtg tccagcggag ggggctttgg    60
accgg                                                               65
```

<210> SEQ ID NO 181
<211> LENGTH: 65
<212> TYPE: DNA
<213> ORGANISM: Artificial
<220> FEATURE:
<223> OTHER INFORMATION: synthetic DNA

<400> SEQUENCE: 181

```
tgagaactcg tggtacttca gtgtccctcc ccctgtattg tgacaaggta attctgtggt    60
atcag                                                               65
```

<210> SEQ ID NO 182
<211> LENGTH: 65
<212> TYPE: DNA
<213> ORGANISM: Artificial

-continued

```
<220> FEATURE:
<223> OTHER INFORMATION: synthetic DNA

<400> SEQUENCE: 182
ctaatacgat gcatatactg aagggcaagg actttgacca tgtcaatttt cagccgagaa      60
tggtc                                                                  65

<210> SEQ ID NO 183
<211> LENGTH: 65
<212> TYPE: DNA
<213> ORGANISM: Artificial
<220> FEATURE:
<223> OTHER INFORMATION: synthetic DNA

<400> SEQUENCE: 183
accaccatgg ttacagcgga tgccccgaga ctctgcttgg taaacgtggc agagcagaat      60
gggag                                                                  65

<210> SEQ ID NO 184
<211> LENGTH: 65
<212> TYPE: DNA
<213> ORGANISM: Artificial
<220> FEATURE:
<223> OTHER INFORMATION: synthetic DNA

<400> SEQUENCE: 184
aaggcagaga gtcagaccct tcaatggaag gagagtgctt gggatcgatt atgtgactta      60
aagtc                                                                  65

<210> SEQ ID NO 185
<211> LENGTH: 65
<212> TYPE: DNA
<213> ORGANISM: Artificial
<220> FEATURE:
<223> OTHER INFORMATION: synthetic DNA

<400> SEQUENCE: 185
gtctgagctt ctttagctag gctaaaacac cttggcttgt tattgcctct actttgattc      60
tgata                                                                  65

<210> SEQ ID NO 186
<211> LENGTH: 65
<212> TYPE: DNA
<213> ORGANISM: Artificial
<220> FEATURE:
<223> OTHER INFORMATION: synthetic DNA

<400> SEQUENCE: 186
gcatttaatt caaagagagg ggagcatcca ttattggtac atgtgggctt ttaaaaactc      60
catcc                                                                  65

<210> SEQ ID NO 187
<211> LENGTH: 65
<212> TYPE: DNA
<213> ORGANISM: Artificial
<220> FEATURE:
<223> OTHER INFORMATION: synthetic DNA

<400> SEQUENCE: 187
gcaccaacat gtaaccggca tgtttccagc agaagacaaa aagacaaaca tgaaagtcta      60
gaaat                                                                  65
```

```
<210> SEQ ID NO 188
<211> LENGTH: 65
<212> TYPE: DNA
<213> ORGANISM: Artificial
<220> FEATURE:
<223> OTHER INFORMATION: synthetic DNA

<400> SEQUENCE: 188
atgcctgccc agttcccttt ttatttgcag aagctgtgag ttttgttcac aattaggttc      60
ctagg                                                                  65

<210> SEQ ID NO 189
<211> LENGTH: 65
<212> TYPE: DNA
<213> ORGANISM: Artificial
<220> FEATURE:
<223> OTHER INFORMATION: synthetic DNA

<400> SEQUENCE: 189
gtgccactag ttaaatgccg aattctcatc tggatgttac catcaaacat cagtacactt      60
gtcat                                                                  65

<210> SEQ ID NO 190
<211> LENGTH: 65
<212> TYPE: DNA
<213> ORGANISM: Artificial
<220> FEATURE:
<223> OTHER INFORMATION: synthetic DNA

<400> SEQUENCE: 190
cagctgcctg ttttgcatgg tatttgcaaa aatgcctctt gcgtgaggaa atcttttacc      60
atttt                                                                  65

<210> SEQ ID NO 191
<211> LENGTH: 65
<212> TYPE: DNA
<213> ORGANISM: Artificial
<220> FEATURE:
<223> OTHER INFORMATION: synthetic DNA

<400> SEQUENCE: 191
gacaatgctg atggaagacc agactggaaa gtggatcgac tcctccttca ttgattctaa      60
attca                                                                  65

<210> SEQ ID NO 192
<211> LENGTH: 65
<212> TYPE: DNA
<213> ORGANISM: Artificial
<220> FEATURE:
<223> OTHER INFORMATION: synthetic DNA

<400> SEQUENCE: 192
ggttagttga tcaagaattt tggggtgggg gttgcggaga aatcaagttt aaaattcctt      60
ctgat                                                                  65

<210> SEQ ID NO 193
<211> LENGTH: 62
<212> TYPE: DNA
<213> ORGANISM: Artificial
<220> FEATURE:
<223> OTHER INFORMATION: synthetic DNA

<400> SEQUENCE: 193
ctctctctct ctctctctct ctctctctct ggtccagtac ttctatctga ttgttgtcca      60
```

```
<210> SEQ ID NO 194
<211> LENGTH: 59
<212> TYPE: DNA
<213> ORGANISM: Artificial
<220> FEATURE:
<223> OTHER INFORMATION: synthetic DNA

<400> SEQUENCE: 194
ctctctctct ctctctctct ctctctctca ggtgctacag ttctgccaga gatcagttg      59

<210> SEQ ID NO 195
<211> LENGTH: 58
<212> TYPE: DNA
<213> ORGANISM: Artificial
<220> FEATURE:
<223> OTHER INFORMATION: synthetic DNA

<400> SEQUENCE: 195
ctctctctct ctctctctct ctctctctcg agccaaagag ggaaaaggct caacactg       58

<210> SEQ ID NO 196
<211> LENGTH: 58
<212> TYPE: DNA
<213> ORGANISM: Artificial
<220> FEATURE:
<223> OTHER INFORMATION: synthetic DNA

<400> SEQUENCE: 196
ctctctctct ctctctctct ctctctctcg ccacaaaatt gttcacccccc aagcaacc     58

<210> SEQ ID NO 197
<211> LENGTH: 59
<212> TYPE: DNA
<213> ORGANISM: Artificial
<220> FEATURE:
<223> OTHER INFORMATION: synthetic DNA

<400> SEQUENCE: 197
ctctctctct ctctctctct ctctctctca tgagcatcaa ggacatctgc gaagcactg      59

<210> SEQ ID NO 198
<211> LENGTH: 73
<212> TYPE: DNA
<213> ORGANISM: Artificial
<220> FEATURE:
<223> OTHER INFORMATION: synthetic DNA

<400> SEQUENCE: 198
ctctctctct ctctctctct ctctctctcg gattcaggca attgttaaaa taagctatac     60
aaatggtgat agg                                                        73

<210> SEQ ID NO 199
<211> LENGTH: 55
<212> TYPE: DNA
<213> ORGANISM: Artificial
<220> FEATURE:
<223> OTHER INFORMATION: synthetic DNA

<400> SEQUENCE: 199
ctctctctct ctctctctct ctctctctcc aggcttccct attgagctcg tggac          55

<210> SEQ ID NO 200
<211> LENGTH: 72
```

```
<212> TYPE: DNA
<213> ORGANISM: Artificial
<220> FEATURE:
<223> OTHER INFORMATION: synthetic DNA

<400> SEQUENCE: 200
ctctctctct ctctctctct ctctctctca ggtaatcaaa gtatgttgca ggttgtgctt    60
gtttttaaac ag                                                         72

<210> SEQ ID NO 201
<211> LENGTH: 60
<212> TYPE: DNA
<213> ORGANISM: Artificial
<220> FEATURE:
<223> OTHER INFORMATION: synthetic DNA

<400> SEQUENCE: 201
ctctctctct ctctctctct ctctctctca cataggccct gaatacaggt gatatagggc    60

<210> SEQ ID NO 202
<211> LENGTH: 51
<212> TYPE: DNA
<213> ORGANISM: Artificial
<220> FEATURE:
<223> OTHER INFORMATION: synthetic DNA

<400> SEQUENCE: 202
ctctctctct ctctctctct ctctctctcg gacagctcct cgtcccggaa g              51

<210> SEQ ID NO 203
<211> LENGTH: 60
<212> TYPE: DNA
<213> ORGANISM: Artificial
<220> FEATURE:
<223> OTHER INFORMATION: synthetic DNA

<400> SEQUENCE: 203
ctctctctct ctctctctct ctctctctca agagagtaaa caaagcgtga gaagccgtcc    60

<210> SEQ ID NO 204
<211> LENGTH: 54
<212> TYPE: DNA
<213> ORGANISM: Artificial
<220> FEATURE:
<223> OTHER INFORMATION: synthetic DNA

<400> SEQUENCE: 204
ctctctctct ctctctctct ctctctctcc ttgcctgccc acagcttact tggc           54

<210> SEQ ID NO 205
<211> LENGTH: 59
<212> TYPE: DNA
<213> ORGANISM: Artificial
<220> FEATURE:
<223> OTHER INFORMATION: synthetic DNA

<400> SEQUENCE: 205
ctctctctct ctctctctct ctctctctct gattgggcat atggtcagca gtagtgtcc     59

<210> SEQ ID NO 206
<211> LENGTH: 60
<212> TYPE: DNA
<213> ORGANISM: Artificial
<220> FEATURE:
<223> OTHER INFORMATION: synthetic DNA

<400> SEQUENCE: 206
```

```
ctctctctct ctctctctct ctctctctcg agtgtctcca catgccaaaa tcagaggaag    60
```

<210> SEQ ID NO 207
<211> LENGTH: 55
<212> TYPE: DNA
<213> ORGANISM: Artificial
<220> FEATURE:
<223> OTHER INFORMATION: synthetic DNA

<400> SEQUENCE: 207

```
ctctctctct ctctctctct ctctctctcc tgagtagtca tagtcggctc ccgag    55
```

<210> SEQ ID NO 208
<211> LENGTH: 67
<212> TYPE: DNA
<213> ORGANISM: Artificial
<220> FEATURE:
<223> OTHER INFORMATION: synthetic DNA

<400> SEQUENCE: 208

```
ctctctctct ctctctctct ctctctctcc cgaaatattc ttgctgacat ttgcatgtta    60
ctgcttc                                                               67
```

<210> SEQ ID NO 209
<211> LENGTH: 53
<212> TYPE: DNA
<213> ORGANISM: Artificial
<220> FEATURE:
<223> OTHER INFORMATION: synthetic DNA

<400> SEQUENCE: 209

```
ctctctctct ctctctctct ctctctctcc tggagtcctc ccattctgag ccc    53
```

<210> SEQ ID NO 210
<211> LENGTH: 52
<212> TYPE: DNA
<213> ORGANISM: Artificial
<220> FEATURE:
<223> OTHER INFORMATION: synthetic DNA

<400> SEQUENCE: 210

```
ctctctctct ctctctctct ctctctctca ggaaccgagg ggtgaccacc tc    52
```

<210> SEQ ID NO 211
<211> LENGTH: 56
<212> TYPE: DNA
<213> ORGANISM: Artificial
<220> FEATURE:
<223> OTHER INFORMATION: synthetic DNA

<400> SEQUENCE: 211

```
ctctctctct ctctctctct ctctctctcc ctcaaaggca cctgggagtt cactac    56
```

<210> SEQ ID NO 212
<211> LENGTH: 52
<212> TYPE: DNA
<213> ORGANISM: Artificial
<220> FEATURE:
<223> OTHER INFORMATION: synthetic DNA

<400> SEQUENCE: 212

```
ctctctctct ctctctctct ctctctctcg gcgtctcacc tggcttgaga gc    52
```

<210> SEQ ID NO 213
<211> LENGTH: 57

```
<212> TYPE: DNA
<213> ORGANISM: Artificial
<220> FEATURE:
<223> OTHER INFORMATION: synthetic DNA

<400> SEQUENCE: 213
ctctctctct ctctctctct ctctctctcg ttgtcgcttg gcaaagaggc tcttgac          57

<210> SEQ ID NO 214
<211> LENGTH: 51
<212> TYPE: DNA
<213> ORGANISM: Artificial
<220> FEATURE:
<223> OTHER INFORMATION: synthetic DNA

<400> SEQUENCE: 214
ctctctctct ctctctctct ctctctctcc tccgctctgg accaacgcag g               51

<210> SEQ ID NO 215
<211> LENGTH: 63
<212> TYPE: DNA
<213> ORGANISM: Artificial
<220> FEATURE:
<223> OTHER INFORMATION: synthetic DNA

<400> SEQUENCE: 215
ctctctctct ctctctctct ctctctctca gtcaagatcg tacttcccat tgcgatagaa      60
ctc                                                                     63

<210> SEQ ID NO 216
<211> LENGTH: 64
<212> TYPE: DNA
<213> ORGANISM: Artificial
<220> FEATURE:
<223> OTHER INFORMATION: synthetic DNA

<400> SEQUENCE: 216
ctctctctct ctctctctct ctctctctct ttccaaaagc aaggtagttg ctgtcccaaa      60
aagc                                                                    64

<210> SEQ ID NO 217
<211> LENGTH: 67
<212> TYPE: DNA
<213> ORGANISM: Artificial
<220> FEATURE:
<223> OTHER INFORMATION: synthetic DNA

<400> SEQUENCE: 217
ctctctctct ctctctctct ctctctctca gcagctgtca cctatacaga gttatgaatc      60
atctttg                                                                 67

<210> SEQ ID NO 218
<211> LENGTH: 60
<212> TYPE: DNA
<213> ORGANISM: Artificial
<220> FEATURE:
<223> OTHER INFORMATION: synthetic DNA

<400> SEQUENCE: 218
ctctctctct ctctctctct ctctctctca ggtgcctgtc tccaactcca agtatatagg      60

<210> SEQ ID NO 219
<211> LENGTH: 56
<212> TYPE: DNA
<213> ORGANISM: Artificial
```

-continued

```
<220> FEATURE:
<223> OTHER INFORMATION: synthetic DNA

<400> SEQUENCE: 219
ctctctctct ctctctctct ctctctctcg caaggcacta gagacccaca tccttc        56

<210> SEQ ID NO 220
<211> LENGTH: 65
<212> TYPE: DNA
<213> ORGANISM: Artificial
<220> FEATURE:
<223> OTHER INFORMATION: synthetic DNA

<400> SEQUENCE: 220
ctctctctct ctctctctct ctctctctcc ttttggagaa aatattgcgt tgtaaggctg    60
acgtc                                                                 65

<210> SEQ ID NO 221
<211> LENGTH: 68
<212> TYPE: DNA
<213> ORGANISM: Artificial
<220> FEATURE:
<223> OTHER INFORMATION: synthetic DNA

<400> SEQUENCE: 221
ctctctctct ctctctctct ctctctctcg aacagattta ccacaacatg ttagaaagag    60
aacagcag                                                              68

<210> SEQ ID NO 222
<211> LENGTH: 66
<212> TYPE: DNA
<213> ORGANISM: Artificial
<220> FEATURE:
<223> OTHER INFORMATION: synthetic DNA

<400> SEQUENCE: 222
ctctctctct ctctctctct ctctctctct tacaagaaaa tcagaacctc ttcaaactca    60
ccctcc                                                                66

<210> SEQ ID NO 223
<211> LENGTH: 56
<212> TYPE: DNA
<213> ORGANISM: Artificial
<220> FEATURE:
<223> OTHER INFORMATION: synthetic DNA

<400> SEQUENCE: 223
ctctctctct ctctctctct ctctctctca actgcctcca ttagggttcg taccgc        56

<210> SEQ ID NO 224
<211> LENGTH: 62
<212> TYPE: DNA
<213> ORGANISM: Artificial
<220> FEATURE:
<223> OTHER INFORMATION: synthetic DNA

<400> SEQUENCE: 224
ctctctctct ctctctctct ctctctctcc aacgactgaa aatgcacttg cttgttgtgg    60
tg                                                                    62

<210> SEQ ID NO 225
<211> LENGTH: 49
<212> TYPE: DNA
<213> ORGANISM: Artificial
```

```
<220> FEATURE:
<223> OTHER INFORMATION: synthetic DNA

<400> SEQUENCE: 225
ctctctctct ctctctctct ctctctctcg gcccctgcct cctctccac        49

<210> SEQ ID NO 226
<211> LENGTH: 58
<212> TYPE: DNA
<213> ORGANISM: Artificial
<220> FEATURE:
<223> OTHER INFORMATION: synthetic DNA

<400> SEQUENCE: 226
ctctctctct ctctctctct ctctctctcc tgaggtcgat ggggtatatc aagtacg    58

<210> SEQ ID NO 227
<211> LENGTH: 54
<212> TYPE: DNA
<213> ORGANISM: Artificial
<220> FEATURE:
<223> OTHER INFORMATION: synthetic DNA

<400> SEQUENCE: 227
ctctctctct ctctctctct ctctctctct ccgaggaaga gctgtcctgt gagg        54

<210> SEQ ID NO 228
<211> LENGTH: 58
<212> TYPE: DNA
<213> ORGANISM: Artificial
<220> FEATURE:
<223> OTHER INFORMATION: synthetic DNA

<400> SEQUENCE: 228
ctctctctct ctctctctct ctctctctca ctgagtttgc aacagaggac ctgccatc    58

<210> SEQ ID NO 229
<211> LENGTH: 51
<212> TYPE: DNA
<213> ORGANISM: Artificial
<220> FEATURE:
<223> OTHER INFORMATION: synthetic DNA

<400> SEQUENCE: 229
ctctctctct ctctctctct ctctctctcc tgcttggccg tgtcggtgag g        51

<210> SEQ ID NO 230
<211> LENGTH: 53
<212> TYPE: DNA
<213> ORGANISM: Artificial
<220> FEATURE:
<223> OTHER INFORMATION: synthetic DNA

<400> SEQUENCE: 230
ctctctctct ctctctctct ctctctctcg cagaggcagg acaataccca gcc        53

<210> SEQ ID NO 231
<211> LENGTH: 61
<212> TYPE: DNA
<213> ORGANISM: Artificial
<220> FEATURE:
<223> OTHER INFORMATION: synthetic DNA

<400> SEQUENCE: 231
ctctctctct ctctctctct ctctctctct tactgaccac aggagaagta acgctaacag    60
g                                                                    61
```

<210> SEQ ID NO 232
<211> LENGTH: 59
<212> TYPE: DNA
<213> ORGANISM: Artificial
<220> FEATURE:
<223> OTHER INFORMATION: synthetic DNA

<400> SEQUENCE: 232
ctctctctct ctctctctct ctctctctca tgagggcatt gcagcccttg ttaaagagg        59

<210> SEQ ID NO 233
<211> LENGTH: 52
<212> TYPE: DNA
<213> ORGANISM: Artificial
<220> FEATURE:
<223> OTHER INFORMATION: synthetic DNA

<400> SEQUENCE: 233
ctctctctct ctctctctct ctctctctcg gggagggaga acagctgagt gg              52

<210> SEQ ID NO 234
<211> LENGTH: 62
<212> TYPE: DNA
<213> ORGANISM: Artificial
<220> FEATURE:
<223> OTHER INFORMATION: synthetic DNA

<400> SEQUENCE: 234
ctctctctct ctctctctct ctctctctca ctggttccaa aactggtgac tgattacggt       60
tc                                                                      62

<210> SEQ ID NO 235
<211> LENGTH: 49
<212> TYPE: DNA
<213> ORGANISM: Artificial
<220> FEATURE:
<223> OTHER INFORMATION: synthetic DNA

<400> SEQUENCE: 235
ctctctctct ctctctctct ctctctctcg ccatggggca cccctgccc                  49

<210> SEQ ID NO 236
<211> LENGTH: 52
<212> TYPE: DNA
<213> ORGANISM: Artificial
<220> FEATURE:
<223> OTHER INFORMATION: synthetic DNA

<400> SEQUENCE: 236
ctctctctct ctctctctct ctctctctca cacgtgggtt gcgtcagtcc cg              52

<210> SEQ ID NO 237
<211> LENGTH: 58
<212> TYPE: DNA
<213> ORGANISM: Artificial
<220> FEATURE:
<223> OTHER INFORMATION: synthetic DNA

<400> SEQUENCE: 237
ctctctctct ctctctctct ctctctctcg aaagagaaaa gagacacaga cccaggcc        58

<210> SEQ ID NO 238
<211> LENGTH: 53
<212> TYPE: DNA
<213> ORGANISM: Artificial

<220> FEATURE:
<223> OTHER INFORMATION: synthetic DNA

<400> SEQUENCE: 238
ctctctctct ctctctctct ctctctctct ggcaaactgc tccacccgtt gcc            53

<210> SEQ ID NO 239
<211> LENGTH: 62
<212> TYPE: DNA
<213> ORGANISM: Artificial
<220> FEATURE:
<223> OTHER INFORMATION: synthetic DNA

<400> SEQUENCE: 239
ctctctctct ctctctctct ctctctctcg atgaagttct cctttagttc cgaagtcagc    60
tc                                                                    62

<210> SEQ ID NO 240
<211> LENGTH: 69
<212> TYPE: DNA
<213> ORGANISM: Artificial
<220> FEATURE:
<223> OTHER INFORMATION: synthetic DNA

<400> SEQUENCE: 240
ctctctctct ctctctctct ctctctctct tacatctcca tgtctgtacc gtaatgttta    60
tttccttcc                                                             69

<210> SEQ ID NO 241
<211> LENGTH: 56
<212> TYPE: DNA
<213> ORGANISM: Artificial
<220> FEATURE:
<223> OTHER INFORMATION: synthetic DNA

<400> SEQUENCE: 241
ctctctctct ctctctctct ctctctctca ctcactgaag tccacctggg catctc        56

<210> SEQ ID NO 242
<211> LENGTH: 54
<212> TYPE: DNA
<213> ORGANISM: Artificial
<220> FEATURE:
<223> OTHER INFORMATION: synthetic DNA

<400> SEQUENCE: 242
ctctctctct ctctctctct ctctctctct gccaggaggc caatcatggt aggc          54

<210> SEQ ID NO 243
<211> LENGTH: 62
<212> TYPE: DNA
<213> ORGANISM: Artificial
<220> FEATURE:
<223> OTHER INFORMATION: synthetic DNA

<400> SEQUENCE: 243
ctctctctct ctctctctct ctctctctct ggtggaaaag taagttgcgt acttacccaa    60
gc                                                                    62

<210> SEQ ID NO 244
<211> LENGTH: 69
<212> TYPE: DNA
<213> ORGANISM: Artificial
<220> FEATURE:
<223> OTHER INFORMATION: synthetic DNA

```
<400> SEQUENCE: 244
ctctctctct ctctctctct ctctctctct agatgcaagt ctagacaata tcaagaactg    60
atggttctc                                                            69

<210> SEQ ID NO 245
<211> LENGTH: 58
<212> TYPE: DNA
<213> ORGANISM: Artificial
<220> FEATURE:
<223> OTHER INFORMATION: synthetic DNA

<400> SEQUENCE: 245
ctctctctct ctctctctct ctctctctct aaccaggtca ggcagcataa gtcctcag      58

<210> SEQ ID NO 246
<211> LENGTH: 65
<212> TYPE: DNA
<213> ORGANISM: Artificial
<220> FEATURE:
<223> OTHER INFORMATION: synthetic DNA

<400> SEQUENCE: 246
ctctctctct ctctctctct ctctctctcc tcttcttttg cagagaagaa agagtcaaaa    60
tcccc                                                                65

<210> SEQ ID NO 247
<211> LENGTH: 66
<212> TYPE: DNA
<213> ORGANISM: Artificial
<220> FEATURE:
<223> OTHER INFORMATION: synthetic DNA

<400> SEQUENCE: 247
ctctctctct ctctctctct ctctctctcc tgtatatctg ttcagcaggg gatctgttta    60
tatctg                                                               66

<210> SEQ ID NO 248
<211> LENGTH: 55
<212> TYPE: DNA
<213> ORGANISM: Artificial
<220> FEATURE:
<223> OTHER INFORMATION: synthetic DNA

<400> SEQUENCE: 248
ctctctctct ctctctctct ctctctctcg acagtagaca cagtgcctgt ggctg          55

<210> SEQ ID NO 249
<211> LENGTH: 72
<212> TYPE: DNA
<213> ORGANISM: Artificial
<220> FEATURE:
<223> OTHER INFORMATION: synthetic DNA

<400> SEQUENCE: 249
ctctctctct ctctctctct ctctctctct acaaagcagt taaaaactca ttcttaccct    60
tgcatgctat tc                                                        72

<210> SEQ ID NO 250
<211> LENGTH: 68
<212> TYPE: DNA
<213> ORGANISM: Artificial
<220> FEATURE:
<223> OTHER INFORMATION: synthetic DNA
```

<400> SEQUENCE: 250
ctctctctct ctctctctct ctctctctca agtggtgttt ggaaagttcc tccattcatt    60
tgatttcc    68

<210> SEQ ID NO 251
<211> LENGTH: 72
<212> TYPE: DNA
<213> ORGANISM: Artificial
<220> FEATURE:
<223> OTHER INFORMATION: synthetic DNA

<400> SEQUENCE: 251
ctctctctct ctctctctct ctctctctca aaaagtaaac agaagtgggt gacaaggtac    60
atataaaatg cc    72

<210> SEQ ID NO 252
<211> LENGTH: 71
<212> TYPE: DNA
<213> ORGANISM: Artificial
<220> FEATURE:
<223> OTHER INFORMATION: synthetic DNA

<400> SEQUENCE: 252
ctctctctct ctctctctct ctctctctct cacaattaca aattatcaca acaattagcg    60
cctgtacttg g    71

<210> SEQ ID NO 253
<211> LENGTH: 57
<212> TYPE: DNA
<213> ORGANISM: Artificial
<220> FEATURE:
<223> OTHER INFORMATION: synthetic DNA

<400> SEQUENCE: 253
ctctctctct ctctctctct ctctctctct tcgcctggca ctcttaaacc actcctc    57

<210> SEQ ID NO 254
<211> LENGTH: 50
<212> TYPE: DNA
<213> ORGANISM: Artificial
<220> FEATURE:
<223> OTHER INFORMATION: synthetic DNA

<400> SEQUENCE: 254
ctctctctct ctctctctct ctctctctct ggctcagcca gtcagcccgg    50

<210> SEQ ID NO 255
<211> LENGTH: 63
<212> TYPE: DNA
<213> ORGANISM: Artificial
<220> FEATURE:
<223> OTHER INFORMATION: synthetic DNA

<400> SEQUENCE: 255
ctctctctct ctctctctct ctctctctcc tactgtcttt accccaaac attgcaaaac    60 ctg    63

<210> SEQ ID NO 256
<211> LENGTH: 51
<212> TYPE: DNA
<213> ORGANISM: Artificial
<220> FEATURE:
<223> OTHER INFORMATION: synthetic DNA

```
<400> SEQUENCE: 256
ctctctctct ctctctctct ctctctctcg cacagatgca cagggtcccc c        51

<210> SEQ ID NO 257
<211> LENGTH: 64
<212> TYPE: DNA
<213> ORGANISM: Artificial
<220> FEATURE:
<223> OTHER INFORMATION: synthetic DNA

<400> SEQUENCE: 257
ctctctctct ctctctctct ctctctctcc ttctctctcc ttctacaaaa agtccaagta    60
cctg                                                                64

<210> SEQ ID NO 258
<211> LENGTH: 67
<212> TYPE: DNA
<213> ORGANISM: Artificial
<220> FEATURE:
<223> OTHER INFORMATION: synthetic DNA

<400> SEQUENCE: 258
ctctctctct ctctctctct ctctctctct gtctcttgct tattgtttag ttctaccatc    60
tgtagcc                                                             67

<210> SEQ ID NO 259
<211> LENGTH: 63
<212> TYPE: DNA
<213> ORGANISM: Artificial
<220> FEATURE:
<223> OTHER INFORMATION: synthetic DNA

<400> SEQUENCE: 259
ctctctctct ctctctctct ctctctctct tgctgagaac ctcttccacc ataagattca    60
ctg                                                                 63

<210> SEQ ID NO 260
<211> LENGTH: 67
<212> TYPE: DNA
<213> ORGANISM: Artificial
<220> FEATURE:
<223> OTHER INFORMATION: synthetic DNA

<400> SEQUENCE: 260
ctctctctct ctctctctct ctctctctcc ttcatagcat cttaccactt acttacacaa    60
atagccc                                                             67

<210> SEQ ID NO 261
<211> LENGTH: 74
<212> TYPE: DNA
<213> ORGANISM: Artificial
<220> FEATURE:
<223> OTHER INFORMATION: synthetic DNA

<400> SEQUENCE: 261
ctctctctct ctctctctct ctctctctct ctttcttttt attcacagca ttgctaaatc    60
agaagcattc acag                                                     74

<210> SEQ ID NO 262
<211> LENGTH: 53
<212> TYPE: DNA
<213> ORGANISM: Artificial
```

```
<220> FEATURE:
<223> OTHER INFORMATION: synthetic DNA

<400> SEQUENCE: 262
ctctctctct ctctctctct ctctctctca cgtccaggat gaggcgctcg tag          53

<210> SEQ ID NO 263
<211> LENGTH: 62
<212> TYPE: DNA
<213> ORGANISM: Artificial
<220> FEATURE:
<223> OTHER INFORMATION: synthetic DNA

<400> SEQUENCE: 263
ctctctctct ctctctctct ctctctctct ctgcgcaagt taggttttgt caagaaaggg    60
tg                                                                   62

<210> SEQ ID NO 264
<211> LENGTH: 54
<212> TYPE: DNA
<213> ORGANISM: Artificial
<220> FEATURE:
<223> OTHER INFORMATION: synthetic DNA

<400> SEQUENCE: 264
ctctctctct ctctctctct ctctctctct tggcctgggc tccaaactgc ttgc          54

<210> SEQ ID NO 265
<211> LENGTH: 54
<212> TYPE: DNA
<213> ORGANISM: Artificial
<220> FEATURE:
<223> OTHER INFORMATION: synthetic DNA

<400> SEQUENCE: 265
ctctctctct ctctctctct ctctctctcc tgcttcccac tctccacctc atcc          54

<210> SEQ ID NO 266
<211> LENGTH: 60
<212> TYPE: DNA
<213> ORGANISM: Artificial
<220> FEATURE:
<223> OTHER INFORMATION: synthetic DNA

<400> SEQUENCE: 266
ctctctctct ctctctctct ctctctctcc tacatgctgg aatcaaacac ctgaaggagc    60

<210> SEQ ID NO 267
<211> LENGTH: 61
<212> TYPE: DNA
<213> ORGANISM: Artificial
<220> FEATURE:
<223> OTHER INFORMATION: synthetic DNA

<400> SEQUENCE: 267
ctctctctct ctctctctct ctctctctcc agttttgtca cctgtataat gggggaagca    60
c                                                                    61

<210> SEQ ID NO 268
<211> LENGTH: 61
<212> TYPE: DNA
<213> ORGANISM: Artificial
<220> FEATURE:
<223> OTHER INFORMATION: synthetic DNA

<400> SEQUENCE: 268
```
ctctctctct ctctctctct ctctctctcc ctctactttt cacaatgacc gaataccgca    60
g                                                                    61

<210> SEQ ID NO 269
<211> LENGTH: 70
<212> TYPE: DNA
<213> ORGANISM: Artificial
<220> FEATURE:
<223> OTHER INFORMATION: synthetic DNA

<400> SEQUENCE: 269
ctctctctct ctctctctct ctctctctcc aaagcatgtt atctttgggg aatgctttaa    60
gatccattac                                                           70

<210> SEQ ID NO 270
<211> LENGTH: 59
<212> TYPE: DNA
<213> ORGANISM: Artificial
<220> FEATURE:
<223> OTHER INFORMATION: synthetic DNA

<400> SEQUENCE: 270
ctctctctct ctctctctct ctctctctcg ccagagatct tgaatagcct cttggtcag     59

<210> SEQ ID NO 271
<211> LENGTH: 63
<212> TYPE: DNA
<213> ORGANISM: Artificial
<220> FEATURE:
<223> OTHER INFORMATION: synthetic DNA

<400> SEQUENCE: 271
ctctctctct ctctctctct ctctctctcc tacacagtag aagggagaca actgtttatg    60
tcc                                                                  63

<210> SEQ ID NO 272
<211> LENGTH: 74
<212> TYPE: DNA
<213> ORGANISM: Artificial
<220> FEATURE:
<223> OTHER INFORMATION: synthetic DNA

<400> SEQUENCE: 272
ctctctctct ctctctctct ctctctctct tgacaataaa ctctacagaa ctggaaatgt    60
tcaaaagtgt caag                                                      74

<210> SEQ ID NO 273
<211> LENGTH: 56
<212> TYPE: DNA
<213> ORGANISM: Artificial
<220> FEATURE:
<223> OTHER INFORMATION: synthetic DNA

<400> SEQUENCE: 273
ctctctctct ctctctctct ctctctctca aacgcctcct cgcccacaac acaatc        56

<210> SEQ ID NO 274
<211> LENGTH: 51
<212> TYPE: DNA
<213> ORGANISM: Artificial
<220> FEATURE:
<223> OTHER INFORMATION: synthetic DNA

<400> SEQUENCE: 274

```
ctctctctct ctctctctct ctctctctca gaaagggggc gcagggctac g            51

<210> SEQ ID NO 275
<211> LENGTH: 55
<212> TYPE: DNA
<213> ORGANISM: Artificial
<220> FEATURE:
<223> OTHER INFORMATION: synthetic DNA

<400> SEQUENCE: 275
ctctctctct ctctctctct ctctctctct cagcagctcc tccttcttct tcccg        55

<210> SEQ ID NO 276
<211> LENGTH: 60
<212> TYPE: DNA
<213> ORGANISM: Artificial
<220> FEATURE:
<223> OTHER INFORMATION: synthetic DNA

<400> SEQUENCE: 276
ctctctctct ctctctctct ctctctctcc aattccagct cccttggatg caaataaccc   60

<210> SEQ ID NO 277
<211> LENGTH: 55
<212> TYPE: DNA
<213> ORGANISM: Artificial
<220> FEATURE:
<223> OTHER INFORMATION: synthetic DNA

<400> SEQUENCE: 277
ctctctctct ctctctctct ctctctctcc agagatccgc acacaaggca cagag        55

<210> SEQ ID NO 278
<211> LENGTH: 60
<212> TYPE: DNA
<213> ORGANISM: Artificial
<220> FEATURE:
<223> OTHER INFORMATION: synthetic DNA

<400> SEQUENCE: 278
ctctctctct ctctctctct ctctctctcc tgcacagcag caaaactcaa tcccaaactc   60

<210> SEQ ID NO 279
<211> LENGTH: 71
<212> TYPE: DNA
<213> ORGANISM: Artificial
<220> FEATURE:
<223> OTHER INFORMATION: synthetic DNA

<400> SEQUENCE: 279
ctctctctct ctctctctct ctctctctcc ctattacata atcagctcgg aatagataca   60
aataattcgg c                                                        71

<210> SEQ ID NO 280
<211> LENGTH: 58
<212> TYPE: DNA
<213> ORGANISM: Artificial
<220> FEATURE:
<223> OTHER INFORMATION: synthetic DNA

<400> SEQUENCE: 280
ctctctctct ctctctctct ctctctctca tagctgaacc ccttggataa gcacacgc     58

<210> SEQ ID NO 281
<211> LENGTH: 68
```

```
<212> TYPE: DNA
<213> ORGANISM: Artificial
<220> FEATURE:
<223> OTHER INFORMATION: synthetic DNA

<400> SEQUENCE: 281
ctctctctct ctctctctct ctctctctca acattacatc tggtgaacag caaagatttc     60
actacacc                                                              68

<210> SEQ ID NO 282
<211> LENGTH: 63
<212> TYPE: DNA
<213> ORGANISM: Artificial
<220> FEATURE:
<223> OTHER INFORMATION: synthetic DNA

<400> SEQUENCE: 282
ctctctctct ctctctctct ctctctctca taaaggtcca ccctgaacct aaatgtgtct     60
gag                                                                   63

<210> SEQ ID NO 283
<211> LENGTH: 62
<212> TYPE: DNA
<213> ORGANISM: Artificial
<220> FEATURE:
<223> OTHER INFORMATION: synthetic DNA

<400> SEQUENCE: 283
ctctctctct ctctctctct ctctctctca ctatagttcc ccttcatgaa attcaccccc     60
ac                                                                    62

<210> SEQ ID NO 284
<211> LENGTH: 61
<212> TYPE: DNA
<213> ORGANISM: Artificial
<220> FEATURE:
<223> OTHER INFORMATION: synthetic DNA

<400> SEQUENCE: 284
ctctctctct ctctctctct ctctctctct gtaaaagcca ctgcttgaga gggaatacag     60
c                                                                     61

<210> SEQ ID NO 285
<211> LENGTH: 62
<212> TYPE: DNA
<213> ORGANISM: Artificial
<220> FEATURE:
<223> OTHER INFORMATION: synthetic DNA

<400> SEQUENCE: 285
ctctctctct ctctctctct ctctctctct tgtaagtttt atactttgtc tggcccaggc     60
cc                                                                    62

<210> SEQ ID NO 286
<211> LENGTH: 67
<212> TYPE: DNA
<213> ORGANISM: Artificial
<220> FEATURE:
<223> OTHER INFORMATION: synthetic DNA

<400> SEQUENCE: 286
ctctctctct ctctctctct ctctctctca tgtaaaatca aggttgatc tgatggtgag     60 caatggg                                                               67
```

-continued

<210> SEQ ID NO 287
<211> LENGTH: 74
<212> TYPE: DNA
<213> ORGANISM: Artificial
<220> FEATURE:
<223> OTHER INFORMATION: synthetic DNA

<400> SEQUENCE: 287
ctctctctct ctctctctct ctctctctcg aaccatttat aattacaatc caaacactcc    60
ataaaccact tgtg                                                      74

<210> SEQ ID NO 288
<211> LENGTH: 72
<212> TYPE: DNA
<213> ORGANISM: Artificial
<220> FEATURE:
<223> OTHER INFORMATION: synthetic DNA

<400> SEQUENCE: 288
ctctctctct ctctctctct ctctctctcc cctattacat taaatcaatg gttcttaagc    60
tcttatgcaa gc                                                        72

<210> SEQ ID NO 289
<211> LENGTH: 55
<212> TYPE: DNA
<213> ORGANISM: Artificial
<220> FEATURE:
<223> OTHER INFORMATION: synthetic DNA

<400> SEQUENCE: 289
ctctctctct ctctctctct ctctctctca gcaggtcagg gtactgctgt gtgag          55

<210> SEQ ID NO 290
<211> LENGTH: 74
<212> TYPE: DNA
<213> ORGANISM: Artificial
<220> FEATURE:
<223> OTHER INFORMATION: synthetic DNA

<400> SEQUENCE: 290
ctctctctct ctctctctct ctctctctct ctgaattttg aattgcaagt agctgtaaaa    60
tccaatcttt gagt                                                      74

<210> SEQ ID NO 291
<211> LENGTH: 59
<212> TYPE: DNA
<213> ORGANISM: Artificial
<220> FEATURE:
<223> OTHER INFORMATION: synthetic DNA

<400> SEQUENCE: 291
ctctctctct ctctctctct ctctctctct ctggcactgc tctgttacaa ctccctatc     59

<210> SEQ ID NO 292
<211> LENGTH: 50
<212> TYPE: DNA
<213> ORGANISM: Artificial
<220> FEATURE:
<223> OTHER INFORMATION: synthetic DNA

<400> SEQUENCE: 292
ctctctctct ctctctctct ctctctctcc caagggcctc cctccctgag                50

```
<210> SEQ ID NO 293
<211> LENGTH: 68
<212> TYPE: DNA
<213> ORGANISM: Artificial
<220> FEATURE:
<223> OTHER INFORMATION: synthetic DNA

<400> SEQUENCE: 293
ctctctctct ctctctctct ctctctctca atgatttaga ccacttgact actgaaagaa    60
gttgcctc                                                              68

<210> SEQ ID NO 294
<211> LENGTH: 56
<212> TYPE: DNA
<213> ORGANISM: Artificial
<220> FEATURE:
<223> OTHER INFORMATION: synthetic DNA

<400> SEQUENCE: 294
ctctctctct ctctctctct ctctctctcc ttggaatagg aagccatggc tggacg         56

<210> SEQ ID NO 295
<211> LENGTH: 70
<212> TYPE: DNA
<213> ORGANISM: Artificial
<220> FEATURE:
<223> OTHER INFORMATION: synthetic DNA

<400> SEQUENCE: 295
ctctctctct ctctctctct ctctctctcc tcatgtttga gcaaacgaag aggtaaatat    60
acacacattc                                                            70

<210> SEQ ID NO 296
<211> LENGTH: 63
<212> TYPE: DNA
<213> ORGANISM: Artificial
<220> FEATURE:
<223> OTHER INFORMATION: synthetic DNA

<400> SEQUENCE: 296
ctctctctct ctctctctct ctctctctcc acacaacagt tgacttatgg actgtcgagt    60
aac                                                                   63

<210> SEQ ID NO 297
<211> LENGTH: 51
<212> TYPE: DNA
<213> ORGANISM: Artificial
<220> FEATURE:
<223> OTHER INFORMATION: synthetic DNA

<400> SEQUENCE: 297
ctctctctct ctctctctct ctctctctcg ggaggagatg ccgctcttgg c              51

<210> SEQ ID NO 298
<211> LENGTH: 59
<212> TYPE: DNA
<213> ORGANISM: Artificial
<220> FEATURE:
<223> OTHER INFORMATION: synthetic DNA

<400> SEQUENCE: 298
ctctctctct ctctctctct ctctctctcc ggaggccaac aactgtattt ccatgtcag     59

<210> SEQ ID NO 299
<211> LENGTH: 61
```

```
<212> TYPE: DNA
<213> ORGANISM: Artificial
<220> FEATURE:
<223> OTHER INFORMATION: synthetic DNA

<400> SEQUENCE: 299
ctctctctct ctctctctct ctctctctct ggctttcacc tgctcattca ggtaatgtgt      60
c                                                                      61

<210> SEQ ID NO 300
<211> LENGTH: 70
<212> TYPE: DNA
<213> ORGANISM: Artificial
<220> FEATURE:
<223> OTHER INFORMATION: synthetic DNA

<400> SEQUENCE: 300
ctctctctct ctctctctct ctctctctct gttcatctcc ttctcgtaca tggaatgtat      60
gttcaaatac                                                             70

<210> SEQ ID NO 301
<211> LENGTH: 61
<212> TYPE: DNA
<213> ORGANISM: Artificial
<220> FEATURE:
<223> OTHER INFORMATION: synthetic DNA

<400> SEQUENCE: 301
ctctctctct ctctctctct ctctctctcc ttctcagatt gaagtggagg gtccagaaat      60
g                                                                      61

<210> SEQ ID NO 302
<211> LENGTH: 62
<212> TYPE: DNA
<213> ORGANISM: Artificial
<220> FEATURE:
<223> OTHER INFORMATION: synthetic DNA

<400> SEQUENCE: 302
ctctctctct ctctctctct ctctctctcc ttcttaccac agtcaccta aagaaccaaa       60 gc                                                                     62

<210> SEQ ID NO 303
<211> LENGTH: 58
<212> TYPE: DNA
<213> ORGANISM: Artificial
<220> FEATURE:
<223> OTHER INFORMATION: synthetic DNA

<400> SEQUENCE: 303
ctctctctct ctctctctct ctctctctct ctgcactggc ttcgtgatgt ccatttgg        58

<210> SEQ ID NO 304
<211> LENGTH: 50
<212> TYPE: DNA
<213> ORGANISM: Artificial
<220> FEATURE:
<223> OTHER INFORMATION: synthetic DNA

<400> SEQUENCE: 304
ctctctctct ctctctctct ctctctctcc ttcgttgccc ctcagccccc                 50

<210> SEQ ID NO 305
<211> LENGTH: 52
```

```
<212> TYPE: DNA
<213> ORGANISM: Artificial
<220> FEATURE:
<223> OTHER INFORMATION: synthetic DNA

<400> SEQUENCE: 305
ctctctctct ctctctctct ctctctctcc tgccgcagct gttcacttgg gc        52

<210> SEQ ID NO 306
<211> LENGTH: 68
<212> TYPE: DNA
<213> ORGANISM: Artificial
<220> FEATURE:
<223> OTHER INFORMATION: synthetic DNA

<400> SEQUENCE: 306
ctctctctct ctctctctct ctctctctct ttaagccttc acaatgtcgc aatggattca        60
gttacttg        68

<210> SEQ ID NO 307
<211> LENGTH: 58
<212> TYPE: DNA
<213> ORGANISM: Artificial
<220> FEATURE:
<223> OTHER INFORMATION: synthetic DNA

<400> SEQUENCE: 307
ctctctctct ctctctctct ctctctctct tggaggttag acacagcaag ctcccaac        58

<210> SEQ ID NO 308
<211> LENGTH: 65
<212> TYPE: DNA
<213> ORGANISM: Artificial
<220> FEATURE:
<223> OTHER INFORMATION: synthetic DNA

<400> SEQUENCE: 308
ctctctctct ctctctctct ctctctctct attgatttaa caatagcctg agctttgggg        60
ctctg        65

<210> SEQ ID NO 309
<211> LENGTH: 66
<212> TYPE: DNA
<213> ORGANISM: Artificial
<220> FEATURE:
<223> OTHER INFORMATION: synthetic DNA

<400> SEQUENCE: 309
ctctctctct ctctctctct ctctctctcg aacatgtagc ttataaaatg cctacacagg        60
tttggc        66

<210> SEQ ID NO 310
<211> LENGTH: 64
<212> TYPE: DNA
<213> ORGANISM: Artificial
<220> FEATURE:
<223> OTHER INFORMATION: synthetic DNA

<400> SEQUENCE: 310
ctctctctct ctctctctct ctctctctct ttgggtgggg gatcacattt attgtattga        60
ggtc        64

<210> SEQ ID NO 311
<211> LENGTH: 50
```

<212> TYPE: DNA
<213> ORGANISM: Artificial
<220> FEATURE:
<223> OTHER INFORMATION: synthetic DNA

<400> SEQUENCE: 311
ctctctctct ctctctctct ctctctctcg gaaaccagga cccggctccc            50

<210> SEQ ID NO 312
<211> LENGTH: 65
<212> TYPE: DNA
<213> ORGANISM: Artificial
<220> FEATURE:
<223> OTHER INFORMATION: synthetic DNA

<400> SEQUENCE: 312
ctctctctct ctctctctct ctctctctca gcttacctag gatgatacca ctttcgctta   60
aacag                                                              65

<210> SEQ ID NO 313
<211> LENGTH: 52
<212> TYPE: DNA
<213> ORGANISM: Artificial
<220> FEATURE:
<223> OTHER INFORMATION: synthetic DNA

<400> SEQUENCE: 313
ctctctctct ctctctctct ctctctctcg taagtcgggt gctgcggagg tg          52

<210> SEQ ID NO 314
<211> LENGTH: 62
<212> TYPE: DNA
<213> ORGANISM: Artificial
<220> FEATURE:
<223> OTHER INFORMATION: synthetic DNA

<400> SEQUENCE: 314
ctctctctct ctctctctct ctctctctct gttaagcagt atctatcagg tggcaaccta   60
gg                                                                 62

<210> SEQ ID NO 315
<211> LENGTH: 57
<212> TYPE: DNA
<213> ORGANISM: Artificial
<220> FEATURE:
<223> OTHER INFORMATION: synthetic DNA

<400> SEQUENCE: 315
ctctctctct ctctctctct ctctctctcc ttctggaggg acgtcgatgg tattagg      57

<210> SEQ ID NO 316
<211> LENGTH: 59
<212> TYPE: DNA
<213> ORGANISM: Artificial
<220> FEATURE:
<223> OTHER INFORMATION: synthetic DNA

<400> SEQUENCE: 316
ctctctctct ctctctctct ctctctctca tcccacattt tacagtgcag gggagaagg    59

<210> SEQ ID NO 317
<211> LENGTH: 61
<212> TYPE: DNA
<213> ORGANISM: Artificial
<220> FEATURE:
<223> OTHER INFORMATION: synthetic DNA

<400> SEQUENCE: 317
ctctctctct ctctctctct ctctctctcg gactcgttca agtatctact gattcaggca    60
g                                                                    61

<210> SEQ ID NO 318
<211> LENGTH: 60
<212> TYPE: DNA
<213> ORGANISM: Artificial
<220> FEATURE:
<223> OTHER INFORMATION: synthetic DNA

<400> SEQUENCE: 318
ctctctctct ctctctctct ctctctctcg tttcctgttg gggagaagct gtaattagcc    60

<210> SEQ ID NO 319
<211> LENGTH: 57
<212> TYPE: DNA
<213> ORGANISM: Artificial
<220> FEATURE:
<223> OTHER INFORMATION: synthetic DNA

<400> SEQUENCE: 319
ctctctctct ctctctctct ctctctctct ccagacactc tctgacaaca cgaaggc       57

<210> SEQ ID NO 320
<211> LENGTH: 57
<212> TYPE: DNA
<213> ORGANISM: Artificial
<220> FEATURE:
<223> OTHER INFORMATION: synthetic DNA

<400> SEQUENCE: 320
ctctctctct ctctctctct ctctctctcg ggacagtctc tgaatgggtc gcttttg       57

<210> SEQ ID NO 321
<211> LENGTH: 67
<212> TYPE: DNA
<213> ORGANISM: Artificial
<220> FEATURE:
<223> OTHER INFORMATION: synthetic DNA

<400> SEQUENCE: 321
ctctctctct ctctctctct ctctctctca tcttctcaag gataggcaca atcatgtcaa    60
atttggg                                                              67

<210> SEQ ID NO 322
<211> LENGTH: 59
<212> TYPE: DNA
<213> ORGANISM: Artificial
<220> FEATURE:
<223> OTHER INFORMATION: synthetic DNA

<400> SEQUENCE: 322
ctctctctct ctctctctct ctctctctct gaactaaagc tggacacgga ctgggtttc     59

<210> SEQ ID NO 323
<211> LENGTH: 62
<212> TYPE: DNA
<213> ORGANISM: Artificial
<220> FEATURE:
<223> OTHER INFORMATION: synthetic DNA

<400> SEQUENCE: 323
ctctctctct ctctctctct ctctctctct ataaatacag ctgtttgggc aggaatcggg    60
tg                                                              62

<210> SEQ ID NO 324
<211> LENGTH: 63
<212> TYPE: DNA
<213> ORGANISM: Artificial
<220> FEATURE:
<223> OTHER INFORMATION: synthetic DNA

<400> SEQUENCE: 324
ctctctctct ctctctctct ctctctctcc cctcataggc ataagtctga agagagtcat    60
aag                                                                 63

<210> SEQ ID NO 325
<211> LENGTH: 59
<212> TYPE: DNA
<213> ORGANISM: Artificial
<220> FEATURE:
<223> OTHER INFORMATION: synthetic DNA

<400> SEQUENCE: 325
ctctctctct ctctctctct ctctctctcg aaaaggcatc tctgtatgt ttccgtggc     59

<210> SEQ ID NO 326
<211> LENGTH: 61
<212> TYPE: DNA
<213> ORGANISM: Artificial
<220> FEATURE:
<223> OTHER INFORMATION: synthetic DNA

<400> SEQUENCE: 326
ctctctctct ctctctctct ctctctctcc actgctttct ccacggggga tcttaattat    60
c                                                                   61

<210> SEQ ID NO 327
<211> LENGTH: 58
<212> TYPE: DNA
<213> ORGANISM: Artificial
<220> FEATURE:
<223> OTHER INFORMATION: synthetic DNA

<400> SEQUENCE: 327
ctctctctct ctctctctct ctctctctcg tgggggagtt caaggagtct gatgattg      58

<210> SEQ ID NO 328
<211> LENGTH: 67
<212> TYPE: DNA
<213> ORGANISM: Artificial
<220> FEATURE:
<223> OTHER INFORMATION: synthetic DNA

<400> SEQUENCE: 328
ctctctctct ctctctctct ctctctctca gagcccttat aaataaaatc ccccagttag    60
tgtttgc                                                             67

<210> SEQ ID NO 329
<211> LENGTH: 69
<212> TYPE: DNA
<213> ORGANISM: Artificial
<220> FEATURE:
<223> OTHER INFORMATION: synthetic DNA

<400> SEQUENCE: 329
ctctctctct ctctctctct ctctctctcc agaaatacta ggaaatgcaa agtcttgaag    60

```
ctccaaaac                                                              69

<210> SEQ ID NO 330
<211> LENGTH: 64
<212> TYPE: DNA
<213> ORGANISM: Artificial
<220> FEATURE:
<223> OTHER INFORMATION: synthetic DNA

<400> SEQUENCE: 330
ctctctctct ctctctctct ctctctctca cccaaagaca tgtgagcaac tgctaatgaa      60
aagc                                                                   64

<210> SEQ ID NO 331
<211> LENGTH: 51
<212> TYPE: DNA
<213> ORGANISM: Artificial
<220> FEATURE:
<223> OTHER INFORMATION: synthetic DNA

<400> SEQUENCE: 331
ctctctctct ctctctctct ctctctctcc caggtctcag cgtctctgcg g               51

<210> SEQ ID NO 332
<211> LENGTH: 56
<212> TYPE: DNA
<213> ORGANISM: Artificial
<220> FEATURE:
<223> OTHER INFORMATION: synthetic DNA

<400> SEQUENCE: 332
ctctctctct ctctctctct ctctctctca atcgcagcct tccagccctc gaaatc         56

<210> SEQ ID NO 333
<211> LENGTH: 52
<212> TYPE: DNA
<213> ORGANISM: Artificial
<220> FEATURE:
<223> OTHER INFORMATION: synthetic DNA

<400> SEQUENCE: 333
ctctctctct ctctctctct ctctctctca cccccagagc cctagctcat cc             52

<210> SEQ ID NO 334
<211> LENGTH: 61
<212> TYPE: DNA
<213> ORGANISM: Artificial
<220> FEATURE:
<223> OTHER INFORMATION: synthetic DNA

<400> SEQUENCE: 334
ctctctctct ctctctctct ctctctctca aggcactgtt ctctttgaag tagggtgagt      60
c                                                                      61

<210> SEQ ID NO 335
<211> LENGTH: 63
<212> TYPE: DNA
<213> ORGANISM: Artificial
<220> FEATURE:
<223> OTHER INFORMATION: synthetic DNA

<400> SEQUENCE: 335
ctctctctct ctctctctct ctctctctca ctttattaca tatgcaacct tgccatgcct      60
gcc                                                                    63
```

<210> SEQ ID NO 336
<211> LENGTH: 55
<212> TYPE: DNA
<213> ORGANISM: Artificial
<220> FEATURE:
<223> OTHER INFORMATION: synthetic DNA

<400> SEQUENCE: 336
ctctctctct ctctctctct ctctctctcg actatggaac cttgggttcc cacgg    55

<210> SEQ ID NO 337
<211> LENGTH: 61
<212> TYPE: DNA
<213> ORGANISM: Artificial
<220> FEATURE:
<223> OTHER INFORMATION: synthetic DNA

<400> SEQUENCE: 337
ctctctctct ctctctctct ctctctctcg tccacacatt atctcagcgg cataaaacgt    60
g    61

<210> SEQ ID NO 338
<211> LENGTH: 51
<212> TYPE: DNA
<213> ORGANISM: Artificial
<220> FEATURE:
<223> OTHER INFORMATION: synthetic DNA

<400> SEQUENCE: 338
ctctctctct ctctctctct ctctctctca gtgacccaga ggcccatccg g    51

<210> SEQ ID NO 339
<211> LENGTH: 67
<212> TYPE: DNA
<213> ORGANISM: Artificial
<220> FEATURE:
<223> OTHER INFORMATION: synthetic DNA

<400> SEQUENCE: 339
ctctctctct ctctctctct ctctctctcc aaccttcttc aagttcacat ctagtagttt    60
tctctgc    67

<210> SEQ ID NO 340
<211> LENGTH: 56
<212> TYPE: DNA
<213> ORGANISM: Artificial
<220> FEATURE:
<223> OTHER INFORMATION: synthetic DNA

<400> SEQUENCE: 340
ctctctctct ctctctctct ctctctctct cactgctctg agggagaaag acgacc    56

<210> SEQ ID NO 341
<211> LENGTH: 59
<212> TYPE: DNA
<213> ORGANISM: Artificial
<220> FEATURE:
<223> OTHER INFORMATION: synthetic DNA

<400> SEQUENCE: 341
ctctctctct ctctctctct ctctctctcg gagcaaagga gagtgcaaag catgtactg    59

<210> SEQ ID NO 342
<211> LENGTH: 56

-continued

```
<212> TYPE: DNA
<213> ORGANISM: Artificial
<220> FEATURE:
<223> OTHER INFORMATION: synthetic DNA

<400> SEQUENCE: 342
ctctctctct ctctctctct ctctctctcg cctccaggtc actcagcttc ttcatg        56

<210> SEQ ID NO 343
<211> LENGTH: 62
<212> TYPE: DNA
<213> ORGANISM: Artificial
<220> FEATURE:
<223> OTHER INFORMATION: synthetic DNA

<400> SEQUENCE: 343
ctctctctct ctctctctct ctctctctca attgcatgaa gcagggcat gaacatctgt    60 tg                                                                    62

<210> SEQ ID NO 344
<211> LENGTH: 61
<212> TYPE: DNA
<213> ORGANISM: Artificial
<220> FEATURE:
<223> OTHER INFORMATION: synthetic DNA

<400> SEQUENCE: 344
ctctctctct ctctctctct ctctctctcg ttctccaccc cacatgtata ccaataccat    60
g                                                                     61

<210> SEQ ID NO 345
<211> LENGTH: 68
<212> TYPE: DNA
<213> ORGANISM: Artificial
<220> FEATURE:
<223> OTHER INFORMATION: synthetic DNA

<400> SEQUENCE: 345
ctctctctct ctctctctct ctctctctct cccaaatagg tgttttacag ataagggtca    60
atacgaag                                                              68

<210> SEQ ID NO 346
<211> LENGTH: 67
<212> TYPE: DNA
<213> ORGANISM: Artificial
<220> FEATURE:
<223> OTHER INFORMATION: synthetic DNA

<400> SEQUENCE: 346
ctctctctct ctctctctct ctctctctct tcaggtctta aggtaaaata gttccacagt    60
ctacagg                                                               67

<210> SEQ ID NO 347
<211> LENGTH: 69
<212> TYPE: DNA
<213> ORGANISM: Artificial
<220> FEATURE:
<223> OTHER INFORMATION: synthetic DNA

<400> SEQUENCE: 347
ctctctctct ctctctctct ctctctctca tgagcagcat tgtaagttgt gatgcattca    60
tttggattg                                                             69
```

-continued

```
<210> SEQ ID NO 348
<211> LENGTH: 56
<212> TYPE: DNA
<213> ORGANISM: Artificial
<220> FEATURE:
<223> OTHER INFORMATION: synthetic DNA

<400> SEQUENCE: 348
ctctctctct ctctctctct ctctctctct ctgctaagcc aagggctgcc acaatg         56

<210> SEQ ID NO 349
<211> LENGTH: 58
<212> TYPE: DNA
<213> ORGANISM: Artificial
<220> FEATURE:
<223> OTHER INFORMATION: synthetic DNA

<400> SEQUENCE: 349
ctctctctct ctctctctct ctctctctcc ctcccctacc tcaaaatgct ttagggag      58

<210> SEQ ID NO 350
<211> LENGTH: 54
<212> TYPE: DNA
<213> ORGANISM: Artificial
<220> FEATURE:
<223> OTHER INFORMATION: synthetic DNA

<400> SEQUENCE: 350
ctctctctct ctctctctct ctctctctca ggacaagcgg tggccaatca accg           54

<210> SEQ ID NO 351
<211> LENGTH: 54
<212> TYPE: DNA
<213> ORGANISM: Artificial
<220> FEATURE:
<223> OTHER INFORMATION: synthetic DNA

<400> SEQUENCE: 351
ctctctctct ctctctctct ctctctctcg tccaggtggc tcatggctcc ttag           54

<210> SEQ ID NO 352
<211> LENGTH: 60
<212> TYPE: DNA
<213> ORGANISM: Artificial
<220> FEATURE:
<223> OTHER INFORMATION: synthetic DNA

<400> SEQUENCE: 352
ctctctctct ctctctctct ctctctctcc cactggggtt tttatccatg tccaattcgc     60

<210> SEQ ID NO 353
<211> LENGTH: 50
<212> TYPE: DNA
<213> ORGANISM: Artificial
<220> FEATURE:
<223> OTHER INFORMATION: synthetic DNA

<400> SEQUENCE: 353
ctctctctct ctctctctct ctctctctcc tccttggagc tgaccgggcc               50

<210> SEQ ID NO 354
<211> LENGTH: 66
<212> TYPE: DNA
<213> ORGANISM: Artificial
<220> FEATURE:
<223> OTHER INFORMATION: synthetic DNA

<400> SEQUENCE: 354
```

```
ctctctctct ctctctctct ctctctctcc ttttagaata gcacactcca aacaagtgat    60
gggaac                                                                66
```

<210> SEQ ID NO 355
<211> LENGTH: 69
<212> TYPE: DNA
<213> ORGANISM: Artificial
<220> FEATURE:
<223> OTHER INFORMATION: synthetic DNA

<400> SEQUENCE: 355

```
ctctctctct ctctctctct ctctctctct ctgcaaacag attcctcttc aacagattat    60
atgcaagag                                                             69
```

<210> SEQ ID NO 356
<211> LENGTH: 67
<212> TYPE: DNA
<213> ORGANISM: Artificial
<220> FEATURE:
<223> OTHER INFORMATION: synthetic DNA

<400> SEQUENCE: 356

```
ctctctctct ctctctctct ctctctctct ttctctcaaa tacactctgg cataccttat    60
cttctcc                                                               67
```

<210> SEQ ID NO 357
<211> LENGTH: 63
<212> TYPE: DNA
<213> ORGANISM: Artificial
<220> FEATURE:
<223> OTHER INFORMATION: synthetic DNA

<400> SEQUENCE: 357

```
ctctctctct ctctctctct ctctctctcc cagttttcca tagtttctag taacgcccaa    60
cag                                                                   63
```

<210> SEQ ID NO 358
<211> LENGTH: 54
<212> TYPE: DNA
<213> ORGANISM: Artificial
<220> FEATURE:
<223> OTHER INFORMATION: synthetic DNA

<400> SEQUENCE: 358

```
ctctctctct ctctctctct ctctctctct ccttggacag aggtgcctga gcac           54
```

<210> SEQ ID NO 359
<211> LENGTH: 56
<212> TYPE: DNA
<213> ORGANISM: Artificial
<220> FEATURE:
<223> OTHER INFORMATION: synthetic DNA

<400> SEQUENCE: 359

```
ctctctctct ctctctctct ctctctctcc atccacctcc actagagcct caaagg         56
```

<210> SEQ ID NO 360
<211> LENGTH: 72
<212> TYPE: DNA
<213> ORGANISM: Artificial
<220> FEATURE:
<223> OTHER INFORMATION: synthetic DNA

<400> SEQUENCE: 360

```
ctctctctct ctctctctct ctctctctct ttctgttata caagtatatt acacagcttg    60
gggtagtaac ag                                                         72

<210> SEQ ID NO 361
<211> LENGTH: 60
<212> TYPE: DNA
<213> ORGANISM: Artificial
<220> FEATURE:
<223> OTHER INFORMATION: synthetic DNA

<400> SEQUENCE: 361
ctctctctct ctctctctct ctctctctcg gcaacagtga gatccagaag cagatcattg    60

<210> SEQ ID NO 362
<211> LENGTH: 60
<212> TYPE: DNA
<213> ORGANISM: Artificial
<220> FEATURE:
<223> OTHER INFORMATION: synthetic DNA

<400> SEQUENCE: 362
ctctctctct ctctctctct ctctctctca cacatggtgc cggaatgata tgtagtcgtc    60

<210> SEQ ID NO 363
<211> LENGTH: 57
<212> TYPE: DNA
<213> ORGANISM: Artificial
<220> FEATURE:
<223> OTHER INFORMATION: synthetic DNA

<400> SEQUENCE: 363
ctctctctct ctctctctct ctctctctcg gatctcattc ctaatggtcc gccgaag       57

<210> SEQ ID NO 364
<211> LENGTH: 64
<212> TYPE: DNA
<213> ORGANISM: Artificial
<220> FEATURE:
<223> OTHER INFORMATION: synthetic DNA

<400> SEQUENCE: 364
ctctctctct ctctctctct ctctctctcg ctgcaaactg gtttaagata gcttgccgat    60
tttg                                                                  64

<210> SEQ ID NO 365
<211> LENGTH: 56
<212> TYPE: DNA
<213> ORGANISM: Artificial
<220> FEATURE:
<223> OTHER INFORMATION: synthetic DNA

<400> SEQUENCE: 365
ctctctctct ctctctctct ctctctctcg gcttccagga cctctgagtt gatacc        56

<210> SEQ ID NO 366
<211> LENGTH: 59
<212> TYPE: DNA
<213> ORGANISM: Artificial
<220> FEATURE:
<223> OTHER INFORMATION: synthetic DNA

<400> SEQUENCE: 366
ctctctctct ctctctctct ctctctctct actgcagaca ctttcctgtg agccagaag     59
```

<210> SEQ ID NO 367
<211> LENGTH: 63
<212> TYPE: DNA
<213> ORGANISM: Artificial
<220> FEATURE:
<223> OTHER INFORMATION: synthetic DNA

<400> SEQUENCE: 367
ctctctctct ctctctctct ctctctctct ttatttccat gttcaacctg cggagaaaac    60
cgg                                                                  63

<210> SEQ ID NO 368
<211> LENGTH: 61
<212> TYPE: DNA
<213> ORGANISM: Artificial
<220> FEATURE:
<223> OTHER INFORMATION: synthetic DNA

<400> SEQUENCE: 368
ctctctctct ctctctctct ctctctctct ttcaggggat taacttggga atggtgcagt    60
g                                                                    61

<210> SEQ ID NO 369
<211> LENGTH: 67
<212> TYPE: DNA
<213> ORGANISM: Artificial
<220> FEATURE:
<223> OTHER INFORMATION: synthetic DNA

<400> SEQUENCE: 369
ctctctctct ctctctctct ctctctctcc tgaatatacc atggaaaact ggggatttat    60
agacagg                                                              67

<210> SEQ ID NO 370
<211> LENGTH: 66
<212> TYPE: DNA
<213> ORGANISM: Artificial
<220> FEATURE:
<223> OTHER INFORMATION: synthetic DNA

<400> SEQUENCE: 370
ctctctctct ctctctctct ctctctctcg gaaaataagt acagtctatt gatccgtgat    60
gcatgc                                                               66

<210> SEQ ID NO 371
<211> LENGTH: 74
<212> TYPE: DNA
<213> ORGANISM: Artificial
<220> FEATURE:
<223> OTHER INFORMATION: synthetic DNA

<400> SEQUENCE: 371
ctctctctct ctctctctct ctctctctct gattctacag gtttaaagtt ttgactgaaa    60
atacacagaa ctca                                                      74

<210> SEQ ID NO 372
<211> LENGTH: 49
<212> TYPE: DNA
<213> ORGANISM: Artificial
<220> FEATURE:
<223> OTHER INFORMATION: synthetic DNA

<400> SEQUENCE: 372
ctctctctct ctctctctct ctctctctcc cggtccaaag cccccctccg               49

<210> SEQ ID NO 373
<211> LENGTH: 64
<212> TYPE: DNA
<213> ORGANISM: Artificial
<220> FEATURE:
<223> OTHER INFORMATION: synthetic DNA

<400> SEQUENCE: 373
ctctctctct ctctctctct ctctctctcc tgataccaca gaattacctt gtcacaatac    60
aggg                                                                  64

<210> SEQ ID NO 374
<211> LENGTH: 63
<212> TYPE: DNA
<213> ORGANISM: Artificial
<220> FEATURE:
<223> OTHER INFORMATION: synthetic DNA

<400> SEQUENCE: 374
ctctctctct ctctctctct ctctctctcg accattctcg gctgaaaatt gacatggtca    60
aag                                                                   63

<210> SEQ ID NO 375
<211> LENGTH: 56
<212> TYPE: DNA
<213> ORGANISM: Artificial
<220> FEATURE:
<223> OTHER INFORMATION: synthetic DNA

<400> SEQUENCE: 375
ctctctctct ctctctctct ctctctctcc tcccattctg ctctgccacg tttacc         56

<210> SEQ ID NO 376
<211> LENGTH: 64
<212> TYPE: DNA
<213> ORGANISM: Artificial
<220> FEATURE:
<223> OTHER INFORMATION: synthetic DNA

<400> SEQUENCE: 376
ctctctctct ctctctctct ctctctctcg actttaagtc acataatcga tcccaagcac    60
tctc                                                                  64

<210> SEQ ID NO 377
<211> LENGTH: 67
<212> TYPE: DNA
<213> ORGANISM: Artificial
<220> FEATURE:
<223> OTHER INFORMATION: synthetic DNA

<400> SEQUENCE: 377
ctctctctct ctctctctct ctctctctct atcagaatca aagtagaggc aataacaagc    60
caaggtg                                                               67

<210> SEQ ID NO 378
<211> LENGTH: 67
<212> TYPE: DNA
<213> ORGANISM: Artificial
<220> FEATURE:
<223> OTHER INFORMATION: synthetic DNA

<400> SEQUENCE: 378
ctctctctct ctctctctct ctctctctcg gatggagttt ttaaaagccc acatgtacca    60

```
ataatgg                                                              67

<210> SEQ ID NO 379
<211> LENGTH: 73
<212> TYPE: DNA
<213> ORGANISM: Artificial
<220> FEATURE:
<223> OTHER INFORMATION: synthetic DNA

<400> SEQUENCE: 379
ctctctctct ctctctctct ctctctctca tttctagact ttcatgtttg tcttttttgtc    60 ttctgctgga aac                                                       73

<210> SEQ ID NO 380
<211> LENGTH: 65
<212> TYPE: DNA
<213> ORGANISM: Artificial
<220> FEATURE:
<223> OTHER INFORMATION: synthetic DNA

<400> SEQUENCE: 380
ctctctctct ctctctctct ctctctctcc ctaggaacct aattgtgaac aaaactcaca    60
gcttc                                                                65

<210> SEQ ID NO 381
<211> LENGTH: 68
<212> TYPE: DNA
<213> ORGANISM: Artificial
<220> FEATURE:
<223> OTHER INFORMATION: synthetic DNA

<400> SEQUENCE: 381
ctctctctct ctctctctct ctctctctca tgacaagtgt actgatgttt gatggtaaca    60
tccagatg                                                             68

<210> SEQ ID NO 382
<211> LENGTH: 69
<212> TYPE: DNA
<213> ORGANISM: Artificial
<220> FEATURE:
<223> OTHER INFORMATION: synthetic DNA

<400> SEQUENCE: 382
ctctctctct ctctctctct ctctctctca aaatggtaaa agatttcctc acgcaagagg    60
cattttttgc                                                           69

<210> SEQ ID NO 383
<211> LENGTH: 68
<212> TYPE: DNA
<213> ORGANISM: Artificial
<220> FEATURE:
<223> OTHER INFORMATION: synthetic DNA

<400> SEQUENCE: 383
ctctctctct ctctctctct ctctctctct gaatttagaa tcaatgaagg aggagtcgat    60
ccactttc                                                             68

<210> SEQ ID NO 384
<211> LENGTH: 67
<212> TYPE: DNA
<213> ORGANISM: Artificial
<220> FEATURE:
<223> OTHER INFORMATION: synthetic DNA
```

```
<400> SEQUENCE: 384
ctctctctct ctctctctct ctctctctca tcagaaggaa ttttaaactt gatttctccg      60
caacccc                                                                67

<210> SEQ ID NO 385
<211> LENGTH: 29
<212> TYPE: DNA
<213> ORGANISM: Artificial
<220> FEATURE:
<223> OTHER INFORMATION: synthetic DNA

<400> SEQUENCE: 385
gagagagaga gagagagaga gagagagag                                        29
```

METHOD FOR CONFIRMING POSITIONS ON WHICH PROBES ARE IMMOBILIZED IN NUCLEIC ACID ARRAY

CROSS-REFERENCE TO PRIOR APPLICATION

This is a U.S. National Phase Application under 35 U.S.C. §371 of International Patent Application No. PCT/JP2006/322063 filed Oct. 30, 2006, and claims the benefit of Japanese Patent Application No. 2005-315190, filed Oct. 28, 2005, both of them are incorporated by reference herein. The International Application was published in Japanese on May 3, 2007 as WO 2007/049827 A1 under PCT Article 21(2).

FIELD OF THE INVENTION

The present invention relates to quality control of a nucleic acid array. Specifically, the present invention relates to a method for confirming types and positions of nucleic acid probes on a nucleic acid array utilizing hybridization reactions of the nucleic acid probes with nucleic acid molecules.

BACKGROUND OF THE INVENTION

A nucleic acid array consists of a carrier on which many nucleic acid probes (hereinafter sometimes referred to as "probes") are independently immobilized at high density without being mixed. A probe immobilized on a nucleic acid array functions as a sensor for capturing a nucleic acid molecule consisting of a sequence complementary to the nucleotide sequence of the probe by means of hybridization.

Conventionally, a product consisting of a carrier made of surface-treated glass, silicone or the like on which probes are immobilized is utilized as a nucleic acid array. Recently, such carriers have been modified using other techniques such as a gel carrier.

As methods for producing a nucleic acid array, a method in which nucleic acid probes prepared in advance are immobilized on a substrate such as slide glass and silicone, and a method in which nucleic acid probes are directly synthesized on a substrate are known.

For example, according to the optical lithography method in which probes are directly synthesized on a substrate, a nucleic acid array can be prepared by using a substance having a protective group which is selectively removed by light irradiation, combining the photolithography technique with the solid-phase synthesis technique, and by selectively synthesizing (masking) DNA on a predetermined region (reaction site) of a tiny matrix (Science 251, 767-773 (1991)).

A typical example of a method for immobilizing probes prepared in advance is a spotting method (Science 270, 467-470 (1995)). According to this method, drops of a solution comprising probes prepared by PCR or artificial synthesis in advance, which have a tiny volume of several nanoliters (nl) to several picoliters (pl), are arrayed on the surface of a chip using a particular apparatus (a spotter an arrayer), and thereby the probes are immobilized on a specific region of the substrate. In addition to the above-described method, a method for producing a microarray using a hollow-fiber-arranged body has been developed. According to this method, a base having through-holes is produced using a hollow-fiber-arranged body in which a plurality of hollow fibers made of synthetic polymer are regularly arrayed in the direction of the fiber axis. One of the features of this production method is that a lot of microarray products having the same specification can be produced from the same rod by immobilizing probes in the hollow portion of each of the hollow fibers in the hollow-fiber-arranged body and by slicing the hollow-fiber-arranged body in the direction perpendicular to the direction of the fiber axis (Japanese Patent No. 3488456).

In a nucleic acid detection method utilizing a nucleic acid array, nucleic acid samples targeted for a test are sequence-specifically hybridized to probes immobilized on the nucleic acid array, and sequence-specifically formed hybrids are detected using a fluorescent substance or the like. According to this method, nucleic acid molecules comprising nucleotide sequences in the samples, which correspond to a plurality of probes, can be examined quantitatively or qualitatively. Therefore, the method is used for analyzing the expression amount of a plurality of nucleotide sequences or the sequence itself of a specific nucleotide sequence.

Usually, in the above-described nucleic acid detection, a hybridization reaction is caused under appropriate preset conditions, and nucleic acid samples and other unnecessary substances remaining on the surface of the array are removed by washing to detect nucleic acid samples forming specific hybrids with probes. A probe is often designed to be complementary or identical to a nucleotide sequence desired to be detected and used for the purpose of sequence analysis, function analysis or the like. As a probe, a nucleic acid having a relatively long chain such as cDNA or the like, a synthetic oligonucleic acid having a relatively short chain, or the like is used. In the case where a synthetic oligonucleic acid is used as the probe for detecting a nucleic acid of human, mouse or other biological organisms, for which the findings of gene information are accumulated, the nucleotide sequence information thereof is usable. Using such nucleotide sequence information, and in consideration of the homology, function and the like of each of such sequences, the sequence of a synthetic oligonucleic acid is designed. Thus, a probe can be produced.

Such nucleic acid arrays can be provided for gene analysis (gene expression, gene polymorphism and the like), can be utilized for research applications such as the discovery of the mechanism of life phenomenon, diagnosis/therapy of diseases and the like, and are further expected to be applied to industrial applications such as breed classification made by differentiating the gene type and the like. In the meantime, in order to apply such nucleic acid arrays to industrial applications, it is essential to maintain the quality thereof. Therefore, one urgent need is to establish a quality control method for guarantee of quality.

Among quality control items, the most important task is to examine whether or not probes immobilized on a nucleic acid array produced are accurately immobilized on predetermined positions. As an example of a method of the above-described examination, a method, in which a nucleic acid array is immersed in a nucleic acid staining agent such as ethidium bromide to stain a probe or a predetermined position on which a probe is immobilized, is known. According to this method, the presence or absence of the probe on/in the nucleic acid array can be known, but it cannot be examined whether or not the probe is immobilized on the predetermined position. Moreover, when utilizing the stained nucleic acid array as it is for a test or the like, the staining agent is a noise in the detection. Therefore, in order to provide nucleic acid arrays as products, it is necessary to conduct an operation, in which a stain (ethidium bromide) that stains probes or predetermined positions on which probes are immobilized must be completely washed away. This procedure must be performed on a product-by-product basis. Therefore, this is a very complicated procedure.

Moreover, in order to confirm spot positions, it is necessary to prepare labeled nucleic acids, which correspond to all probes immobilized on an array, as complementary chains of the probes, and to conduct a detection operation by means of hybridization on a probe to probe basis. When a large number of probes are immobilized, operations are more complicated and unpractical.

Thus, it is very important to easily confirm "what kind of sequence a probe has and on which position of a nucleic acid array the probe is immobilized" to guarantee the quality of the nucleic acid array.

However, presently almost no operation for confirmation is performed. That is because, as described above, since a nucleic acid array has a lot of probes immobilized on a carrier, operations for confirmation are complicated. Moreover, that is because it is difficult to easily differentiate sequences of probes themselves.

That is, in order to confirm what kind of probe is present on which position of a nucleic acid array once prepared, only the information obtained from the production process of the nucleic acid array can be relied on. It is extremely difficult to determine each position on which each probe is immobilized after the production.

If unexpected probes are immobilized on unexpected positions of a nucleic acid array, with respect to probes whose immobilized positions are wrong, wrong data may be submitted without even noticing. Moreover, particularly in the case where a nucleic acid array in which the types of probes are narrowed is prepared, the level of importance of every probe is higher compared to a nucleic acid array on which a wide variety of probes are immobilized in an all-encompassing manner. Therefore, when statistically treating and interpreting the data of every probe obtained from the entire nucleic acid array, there is a high possibility that it will lead to radically wrong conclusions.

SUMMARY OF THE INVENTION

Therefore, the problem of the present invention is to provide a method for accurately and easily confirming that probes immobilized on a nucleic acid array are correctly arrayed on predetermined positions.

In order to solve the above-described problem, the present inventors made keen examination, focusing on the advantage that, in the case of one type of arrays which can be produced from the identical rod, all the array products obtained from the rod can be confirmed by examining a certain number of the arrays. As a result, it was found that, by giving predetermined pieces of identification information to nucleic acid samples to be hybridized to an array, and by effectively combining signals obtained by hybridization with pieces of identification information obtained from individual probes to apply the combination to the test, the positions of the probes can be confirmed individually. Thus, the present invention was completed.

More specifically, the present invention is as follows:

(1) A method for confirming immobilization conditions of nucleic acid probes immobilized on a nucleic acid array, comprising the steps of:
(a) defining the number of zones to which the nucleic acid probes immobilized on the nucleic acid array belong and one or more given pieces of identification information;
(b) calculating X using the following formula:

$$X=\{\log_{(N+1)} M\}+1$$

(wherein N represents the number of the pieces of identification information, and M represents the number of the zones to which the nucleic acid probes immobilized on the nucleic acid array belong), defining a number of the integer portion of X as the number of nucleic acid arrays required for confirming the immobilization conditions, $X_a$, and allocating non-overlapping numerical values (Y), which are expressed by notation system of base N+1, and which have the same digit number as $X_a$, to the respective nucleic acid probes belonging to the zones;

(c) preparing complementary nucleic acid molecules comprising nucleotide sequences complementary to all or a part of nucleotide sequences of the nucleic acid probes, preparing groups of nucleic acid samples corresponding to the number of nucleic acid arrays ($X_a$) by mixing the complementary nucleic acid molecules based on the number of every digit of each of the allocated numerical values (Y), and preparing nucleic acid arrays (the number: $X_a$);

(d) contacting each of the nucleic acid arrays (the number: $X_a$) prepared in the step (c) with the corresponding group of the nucleic acid samples to detect signals derived from hybrids between the nucleic acid probes immobilized on the nucleic acid arrays and the complementary nucleic acid molecules; and (e) matching patterns of expression of the signals detected to patterns of the numerical values (Y) allocated.

In the present invention, examples of the immobilization conditions of the nucleic acid probes include those related to types and/or positions of the nucleic acid probes. The identification information is, for example, at least one selected from the group consisting of: a presence or an absence of a signal; the strength of the signal; and the type of labeling. In the present invention, patterns of expression of the detected signals can be quantified by notation system of base N+1 based on the above-described identification information.

(2) A method for examining a quality of a nucleic acid array, wherein the quality of the nucleic acid array is examined based on results obtained according to the method described in item (1) above.

According to the present invention, a method for confirming types and positions of individual nucleic acid probes immobilized on the nucleic acid arrays by hybridization between the nucleic acid probes and nucleic acids comprising their complementary sequences is provided.

To confirm whether or not individual probes on a nucleic acid array are arrayed on predetermined positions is the most important examination item in terms of the quality control of DNA microarrays. According to the present invention, the positions on which the probes are arrayed can be accurately and easily examined. Therefore, conventionally-used complicated examination steps are no longer required.

BRIEF DESCRIPTION OF THE DRAWINGS

FIG. 2 shows a design of a nucleic acid array. Numbers represent SEQ ID NOs, and B represents a spot on which no probe is immobilized.

FIG. 3 shows images of detection in which hybridization was performed using Samples 1-8.

EXPLANATIONS OF LETTERS OR NUMERALS

Figure 1:
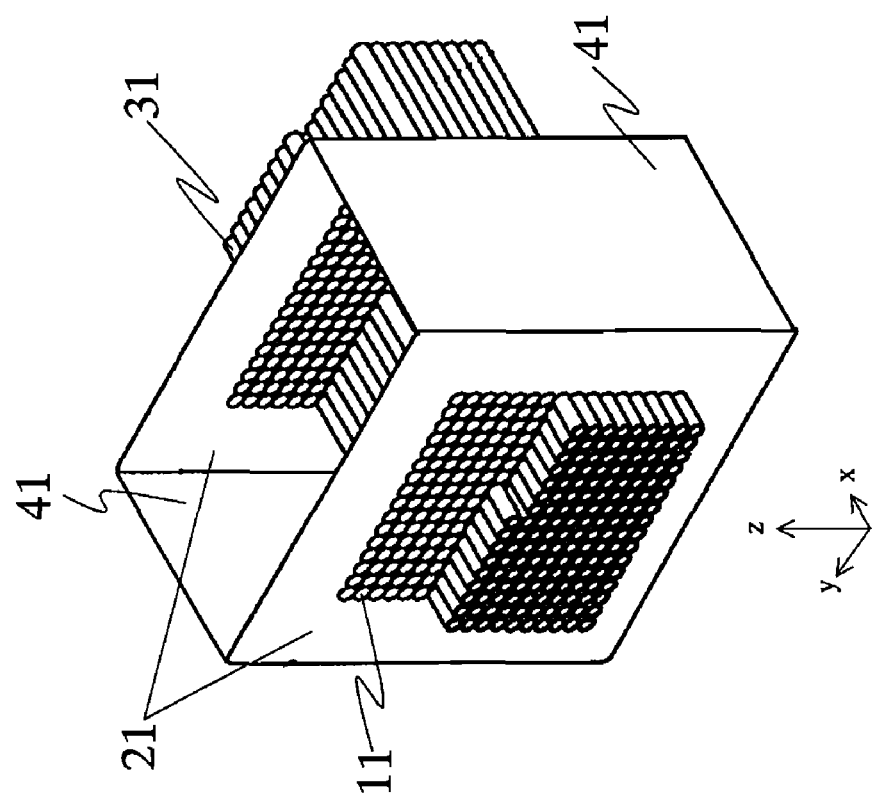
FIG. 1 shows an arrangement fixing tool for producing a fiber-arranged body.

11 . . . pore
21 . . . porous plate
31 . . . hollow fiber
41 . . . plate-like body

DETAILED DESCRIPTION OF THE INVENTION

Hereinafter, the present invention will be described in detail. The documents, laid-open publications, patents and other patent documents cited in this specification are incorporated herein by reference.

The present invention relates to a method for confirming immobilization conditions of nucleic acid probes immobilized on a nucleic acid array, comprising the steps of:
(a) defining the number of zones to which the nucleic acid probes immobilized on the nucleic acid array belong and one or more given pieces of identification information;
(b) calculating X using the following formula:

$$X = \{\log_{(N+1)} M\} + 1$$

(wherein N represents the number of the pieces of identification information, and M represents the number of the zones to which the nucleic acid probes immobilized on the nucleic acid array belong),
defining a number of the integer portion of X as the number of nucleic acid arrays required for confirming the immobilization conditions, $X_a$, and allocating non-overlapping numerical values (Y), which are expressed by notation system of base N+1, and which have the same digit number as $X_a$, to the respective nucleic acid probes belonging to the zones;
(c) preparing complementary nucleic acid molecules comprising nucleotide sequences complementary to all or a part of nucleotide sequences of the nucleic acid probes, preparing groups of nucleic acid samples corresponding to the number of nucleic acid arrays ($X_a$) by mixing the complementary nucleic acid molecules based on the number of every digit of each of the allocated numerical values (Y), and preparing nucleic acid arrays (the number: $X_a$);
(d) contacting each of the nucleic acid arrays (the number: $X_a$) prepared in the step (c) with the corresponding group of the nucleic acid samples to detect signals derived from hybrids between the nucleic acid probes immobilized on the nucleic acid arrays and the complementary nucleic acid molecules; and
(e) matching patterns of expression of the signals detected to patterns of the numerical values (Y) allocated.

1. Method for Confirming Types and Positions of Nucleic Acid Probes

In a general method of using a nucleic acid array, firstly, a sample whose sequence is unknown is hybridized to a nucleic acid probe having a predetermined sequence. If a nucleic acid molecule having a nucleotide sequence complementary to the nucleotide sequence of the nucleic acid probe is present in the sample, a hybrid is formed between the nucleic acid probe and the nucleic acid molecule.

Next, by quantifying or qualifying the hybrid formation using a signal derived from a substance by which the sample is labeled in advance (e.g., fluorescence, chemiluminescence, radioisotope, etc.), the presence of the complementary nucleic acid molecule corresponding to the pertinent nucleic acid probe can be confirmed.

Further, by utilizing the above-described method, the arrangement of a probe immobilized on a nucleic acid array can also be examined. By using a nucleic acid molecule complementary to the probe as a sample, the position of the probe to be present on the nucleic acid array can be identified by means of hybridization.

As described above, in order to confirm on which portion of a nucleic acid array a specific nucleic acid probe is immobilized, a sample comprising a nucleic acid molecule having a nucleotide sequence complementary to the nucleic acid probe (complementary nucleic acid molecule) is hybridized to the nucleic acid array, and a hybrid formed between the nucleic acid probe and the complementary nucleic acid molecule is detected by a signal sent from a labeling substance (e.g., a fluorescent substance, an enzyme, etc.) by which the complementary nucleic acid molecule is labeled. For example, in the case of a nucleic acid array in which nucleic acid probes with 5 different nucleotide sequences are independently immobilized on a substrate, in order to examine the presence or absence of the 5 nucleic acid probes and the positions on which they are present, each of nucleic acid molecules complementary to the respective nucleic acid probes (complementary nucleic acid molecules) is hybridized to each of nucleic acid arrays, and signals derived from hybridization are read, and thereby the relative positions of the nucleic acid probes and nucleotide sequences of the nucleic acid probes immobilized on the positions can be identified.

In this case, the required number of the nucleic acid arrays to be used is 5, corresponding to the number of the nucleic acid probes. Further, if signals, by which 5 types of complementary nucleic acid molecules corresponding to 5 types of nucleic acid probes can be recognized independently (e.g., 5 types of fluorescent substances having different wavelength), can be read, by hybridizing 5 types of the complementary nucleic acid molecules to one nucleic acid array, the relative positions of the nucleic acid probes immobilized and the nucleotide sequences of the nucleic acid probes immobilized on the positions can be confirmed independently.

However, many types of probes are immobilized on a nucleic acid array. At least several tens to several hundreds of types of nucleic acid probes are immobilized. In such a case, it is extremely complicated to confirm the position of each of the nucleic acid probes immobilized by preparing complementary nucleic acid molecules whose number corresponds to the number of the nucleic acid probes and using nucleic acid arrays whose number is the same as that of the immobilized probes. Moreover, such a process cannot be substantially practiced since the number of nucleic acid arrays to be used is excessive. Under present circumstances, it is difficult to provide signal molecules, by which several tens to several hundreds of types of probes can be independently recognized, to respective complementary nucleic acid molecules.

According to the present invention, in order to efficiently identify the positions of nucleic acid probes immobilized, (groups of) complementary nucleic acid samples prepared following definite laws are hybridized to a nucleic acid array, and signals obtained therefrom are matched to the presence or absence of complementary nucleic acid molecules in the nucleic acid samples or the type of labeling.

In this regard, the term "complementary nucleic acid sample" (also referred to as "nucleic acid sample") refers to a sample which comprises a molecule comprising a nucleotide sequence complementary to at least a part of a nucleotide sequence of a nucleic acid probe (complementary nucleic acid molecule) following definite laws. The population of a plurality of complementary nucleic acid samples is referred to as "the group of complementary nucleic acid samples" (also referred to as "the group of nucleic acid samples"). It is preferred to prepare nucleic acid samples as many as nucleic acid arrays to be used for confirmation. The phrase "prepared following definite laws" means that a nucleic acid sample included in a complementary nucleic acid sample is prepared so that respective probes show different patterns at the time of hybridization detection depending on the type of labeling or the presence or absence of the nucleic acid sample. The detailed method will be exemplified below.

7

(1) Definition of the Number of Zones to which Nucleic Acid Probes Immobilized on a Nucleic Acid Array Belong and One or More Given Pieces of Identification Information Nucleic acid probes immobilized on a nucleic acid array are positioned within certain zones. Therefore, the number of zones on which nucleic acid probes are immobilized means the number of the nucleic acid probes (the number of the types of probes). In the present invention, the above-described number of zones is defined as the number of probes. However, the number of zones on which probes are not immobilized can be included in the number of probes, for example, as negative control. "The number of probes" does not mean the number of respective probes included in zones, but refers to the number of populations of probes in zones.

When preparing (groups of) complementary nucleic acid samples, sequence information, concentration, the type of labeling and the like of complementary nucleic acid molecules constituting the (groups of) samples are recorded in advance. These pieces of information are used as pieces of "identification information" for evaluating conditions of hybrids formed between probes and complementary nucleic acid molecules after hybridization. Further, complementary nucleic acid molecules, nucleic acid samples and groups of nucleic acid samples are identified (defined) by number allocation or the like. For example, the presence or absence of a certain nucleic acid sample in a group of nucleic acid samples is represented by a piece of identification information, "the presence or absence of hybridization signal", at the time of detection after hybridization. Further, when using a group of nucleic acid samples including nucleic acid samples labeled with different types of labels (for example, Cy3 and Cy5), "the type of hybridization signal" is utilized as a piece of identification information in the sense that the difference between labels can be distinguished. Moreover, change in the concentration of nucleic acid sample can also be employed as identification information from the viewpoint of "the strength of hybridization signal". Thus, pieces of identification information are used as parameters indicating differences in information obtained after hybridization and causes thereof.

Specifically, when a probe A is immobilized on a nucleic acid array, at the time of putting its complementary chain A' into respective complementary nucleic acid samples of a group of complementary nucleic acid samples, already-known pieces of information such as "whether or not A' is put", "the type of label applied to A'" and "the amount of A' put" can be identified by pieces of information obtained after hybridization such as "whether or not signal was obtained", "the type of fluorescence obtained" and "the degree of signal obtained". Therefore, conditions of input of the complementary nucleic acid molecule A' into respective complementary nucleic acid samples can be easily judged based on results of hybridization.

The number of arrays required for confirming immobilized nucleic acid probes is determined by the number of types of nucleic acid probes and the number of pieces of identification information. When confirming positions of nucleic acid probes immobilized on a nucleic acid array, the more pieces of identification information, the smaller the number of complementary nucleic acid samples to be prepared. Therefore, the number of nucleic acid arrays to be used can be reduced, and as a result, confirmation can be efficiently made.

(2) Calculation of the Number of Nucleic Acid Arrays Required for Confirmation of Immobilization Conditions and Allocation of Numerical Values to Nucleic Acid Probes When confirming positions of all nucleic acid probes immobilized on a nucleic acid array, the number of pieces of identification information required, the number of arrays to be used and the number of complementary nucleic acid samples are represented by conditions satisfying the following formula:

$$M \leq (N+1)^X - 1$$

wherein:
M: the number of types of nucleic acid probes;
N: the number of pieces of identification information; and
X: the number of arrays to be used.

The equality portion of the above-described formula can be represented by the following formula:

$$X = \{\log_{(N+1)} M\} + 1$$

(wherein N represents the number of the pieces of identification information, and M represents the number of the zones to which the nucleic acid probes immobilized on the nucleic acid array belong), and X can be calculated using this formula. The calculated X is represented by a number of the integer portion and a number of the fractional portion. In the present invention, the number of the integer portion of X is defined as the number of nucleic acid arrays required for confirmation of immobilization conditions ($X_a$).

For example, when judging a nucleic acid array, wherein the number of probes (M) is 250 and the number of pieces of identification information is 1 (the presence or absence of signal), since the number of pieces of identification information by which hybridization can be confirmed is 1 (N=1), $X=\log_2 250+1=8.9657$ .... Since the integer portion of X is "8", the number of arrays required for confirmation ($X_a$) is 8. By using 8 arrays ($X_a=8$), the relative positions of all the probes immobilized on the array can be confirmed.

Further, in another embodiment of the present invention, when judgment is made using the following pieces of identification information: 2 types of fluorescence (Cy3 and Cy5); and 2 concentrations of complementary nucleic acid molecule, the number of pieces of identification information by which hybridization can be confirmed is 4 (N=4). Therefore, by using 4 arrays ($X_a=4$), the relative positions of all the probes immobilized on the array can be confirmed.

Hereinafter, an embodiment of the present invention in which a nucleic acid array on which 24 types of nucleic acid probes are immobilized is examined by the presence or absence of fluorescence signal will be considered.

Since the presence or absence of fluorescence signal can be confirmed by one fluorescent label, the number of pieces of identification information (N) is 1. When this number and the number of the probes (M) are applied to the above-described formula, the number of arrays required for confirmation is 5.

Complementary nucleic acid samples, which are to be hybridized to 5 arrays, respectively, are designated as Sample A, Sample B, Sample C, Sample D and Sample E, respectively. Non-overlapping numerical values (Y), which are represented by notation system of base N+1, and which have the same digit number as $X_a$ (Samples A to E=5 types of samples, that is, 5-digit), are allocated to the respective nucleic acid probes belonging to the aforementioned zones. In the above-described example, $X_a=5$, and N+1=2, and therefore, numerical values (Y), which are allocated to probes 1 to 24 in Table 1, can be represented by 5-digit numbers in binary notation, using "1" and "0" as shown in columns A-E therein. In columns of samples A-E, "1" indicates that a fluorescently-labeled complementary nucleic acid is included, and "0" indicates that no complementary nucleic acid is included.

As shown in Table 1, the numerical value allocated to probe 1 (designated as $Y_1$) is "10000", and the numerical value allocated to probe 2 (designated as $Y_2$) is "10001". Numerical values allocated to probes 1-24 do not overlap each other and are different.

TABLE 1

| probe | nucleic acid sample | | | | |
|---|---|---|---|---|---|
| | A | B | C | D | E |
| 1 | 1 | 0 | 0 | 0 | 0 |
| 2 | 1 | 0 | 0 | 0 | 1 |
| 3 | 1 | 0 | 0 | 1 | 0 |
| 4 | 1 | 0 | 0 | 1 | 1 |
| 5 | 1 | 0 | 1 | 0 | 0 |
| 6 | 1 | 0 | 1 | 0 | 1 |
| 7 | 1 | 0 | 1 | 1 | 0 |
| 8 | 1 | 0 | 1 | 1 | 1 |
| 9 | 1 | 1 | 0 | 0 | 0 |
| 10 | 1 | 1 | 0 | 0 | 1 |
| 11 | 1 | 1 | 0 | 1 | 0 |
| 12 | 1 | 1 | 0 | 1 | 1 |
| 13 | 1 | 1 | 1 | 0 | 0 |
| 14 | 1 | 1 | 1 | 0 | 1 |
| 15 | 1 | 1 | 1 | 1 | 0 |
| 16 | 1 | 1 | 1 | 1 | 1 |
| 17 | 0 | 1 | 0 | 0 | 0 |
| 18 | 0 | 1 | 0 | 0 | 1 |
| 19 | 0 | 1 | 0 | 1 | 0 |
| 20 | 0 | 1 | 0 | 1 | 1 |
| 21 | 0 | 1 | 1 | 0 | 0 |
| 22 | 0 | 1 | 1 | 0 | 1 |
| 23 | 0 | 1 | 1 | 1 | 0 |
| 24 | 0 | 1 | 1 | 1 | 1 |

(3) Preparation of Groups of Complementary Nucleic Acid Samples and Preparation of Arrays for Hybridization In this step: complementary nucleic acid molecules comprising a nucleotide sequence complementary to all or a part of nucleotide sequences of the aforementioned nucleic acid probes are prepared; complementary nucleic acid molecules are mixed based on each numerical value in 5 digits of the allocated numerical values (Y) to prepare groups of nucleic acid samples whose number corresponds to the number of nucleic acid arrays ($X_a$); and the nucleic acid arrays (the number thereof: $X_a$) are prepared.

After allocating the above-described numerical values (Y), groups of complementary nucleic acid samples to be independently hybridized to 5 arrays are prepared and designated as samples A, B, C, D and E (Table 1). Nucleic acids can be synthesized using a chemical synthesis apparatus based on sequence information of probes.

Each sample is a mixture obtained by mixing complementary chains of probes, to which the numerical value "1" is allocated. For example, sample A includes complementary chains corresponding to probes 1-16, and sample B includes complementary chains corresponding to probes 9-24. "Complementary chains" are not required to be complementary to all nucleic acid probes, and may be complementary to a part of them.

When complementary nucleic acid molecules are labeled to give identification information, such complementary nucleic acid molecules are confirmed with single labeling, or they are independently detected with single labeling, and it is required that differences can be confirmed simultaneously or with time intervals at the time of detection. That is, regarding labeling, there is a case where single labeling is conducted and confirmation is made by one detection, and there is a case where single labeling is conducted but complementary nucleic acid molecules are independently confirmed by a plurality of detections. Specifically, the following cases are included:

(i) the case where difference in labels is confirmed simultaneously at the time of detection (e.g., combination of Cy3 and Cy5, etc.); and (ii) the case where difference in labels is confirmed with time intervals at the time of detection (e.g., the case where using an identical labeling substance, detection is performed with direct labeling, and thereafter detection is performed with indirect labeling).

In the case of item (2) above, detection can be performed using the combination of Cy5 direct labeling and biotin direct labeling-streptavidin-Cy5 indirect labeling.

The above-described method of "labeling" is not particularly limited as long as hybridization of nucleic acid can be detected. Examples of labeling substances to be used for labeling include: fluorescent substances such as Cy3, Cy5, Alexa Fluor® and the like; enzymes or proteins for utilizing chemiluminescence associated with substrate degradation using alkaline phosphatase, horseradish peroxidase or the like; and radioisotopes such as $\gamma\text{-}^{32}P$, $\alpha\text{-}^{32}P$, etc. From the viewpoint of convenience, use of fluorescent substances is preferable.

When these labeling substances are introduced into complementary nucleic acid molecules, any method (associated with direct, indirect, physical, or chemical binding) can be used as long as it is stable and does not inhibit specific hybridization to probe nucleic acids. Examples of methods of chemical modification include a method, in which an analog base modified by biotin or an aminoaryl group is introduced at the time of reaction, and a labeling substance is introduced via the modified analog base. Moreover, a method for intercalating a labeling substance into a complementary nucleic acid molecule using SYBR® Green, acridine orange, SYBR® Gold or the like, a method for binding a labeling substance such as ULYSIS to a complementary nucleic acid molecule via platinum and the like can also be employed.

However, preparation of many complementary nucleic acid molecules labeled with a labeling molecule may lead to high costs. In order to avoid this, aside from a portion of each complementary nucleic acid molecule complementary to a corresponding nucleic acid probe, a common nucleotide sequence (tag) is added to the 3'- or 5'-terminus of each complementary nucleic acid molecule, and then, a labeled nucleic acid molecule complementary to the tag sequence can be used. In this case, any labeling method can be employed as long as signals can be independently detected. Moreover, a plurality of types of tag sequences themselves can also be used.

(4) Hybridization and Signal Detection

In this step, each of the nucleic acid arrays (the number thereof: $X_a$) prepared as described above is contacted with the aforementioned corresponding group of the nucleic acid samples, and signals derived from hybrids between the nucleic acid probes immobilized on the nucleic acid array and the aforementioned complementary nucleic acid molecules are detected.

When contact of probes with complementary nucleic acids (hybridization) is performed by adding the samples A-E to the nucleic acid arrays A-E, respectively, in the case of the nucleic acid array A, fluorescence signal is detected with respect to the probes 1-16, and in the case of the nucleic acid array B, fluorescence signal is detected with respect to the probes 9-24. Similarly, in the cases of the nucleic acid arrays C-E, fluorescence signal is detected with respect to probes to which the numerical value "1" is allocated.

(5) Matching of Expression Patterns of Detected Signals to Patterns of Allocated Numerical Values (Y)

According to the above-described method, by matching the combination of complementary nucleic acid molecules included in the complementary nucleic acid sample, position information of probes at each position of the nucleic acid array and signals actually obtained by hybridization to identification information, it can be confirmed to which position on the nucleic acid array each nucleic acid probe corresponding to each complementary nucleic acid sample is spotted.

When detection results of each nucleic acid array are examined with respect to each complementary nucleic acid, for example, in the case of the complementary nucleic acid corresponding to probe 1 in Table 1, since it is included only in nucleic acid sample A, the combination of pieces of identification information among nucleic acid samples A-E (the numerical value $Y_1$) is "10000". Further, in the case of the complementary nucleic acid corresponding to probe 16, since it is included in all the nucleic acid samples A-E, the combination of pieces of identification information among nucleic acid samples A-E is "11111". Each complementary nucleic acid has a different combination of pieces of identification information. Therefore, when the pattern of numerical value allocated to each of the probes is matched to the pattern of detection result, and the obtained detection result corresponds to the combination, i.e., the pattern of value Y, it can be judged that the type and the position of the nucleic acid probe immobilized on the nucleic acid array are correct.

For example, when the presence of signal is represented by "+" and the absence of signal is represented by "−", and given that the results "+, −, −, −, −" were obtained in the order of samples A-E as detection results of probe 1, the detection results correspond to $Y_1$="10000". The above-described detection results ("+" and "−") can be represented by numerical values. When the detection results are represented by "1" and "0" (binary notation), the detection results correspond to the allocated numerical value $Y_1$ ("10000"). Therefore, it can be judged that the nucleic acid is immobilized on the correct position.

Next, an embodiment, in which a nucleic acid array on which 24 types of nucleic acid probes are immobilized is examined with 3 types of fluorescence signals, will be considered. Since 3 types of fluorescent labels are used, the number of pieces of identification information (N) is 3. When this number and the number of the probes (M) are applied to the above-described formula, the number of arrays required for confirmation ($X_a$) is 3.

Complementary nucleic acid samples, which are to be hybridized to 3 arrays, respectively, are prepared and designated as Sample A, Sample B and Sample C, respectively (Table 2). As pieces of identification information, "0" represents a green fluorescent label, "1" represents a yellow fluorescent label, and "2" represents a red fluorescent label. "0", "1" or "2" is applied to column of Samples A-C in Table 2.

In this case, since $X_a$=3 and N+1=3, numerical values (Y), which are allocated to probes 1 to 24 in Table 2, can be represented by 3-digit numbers in ternary notation, using "0", "1" and "0" as shown in columns A-C therein.

TABLE 2

| probe | nucleic acid sample | | |
|---|---|---|---|
| | A | B | C |
| 1 | 0 | 0 | 0 |
| 2 | 0 | 0 | 1 |
| 3 | 0 | 0 | 2 |
| 4 | 0 | 1 | 0 |
| 5 | 0 | 1 | 1 |

TABLE 2-continued

| probe | nucleic acid sample | | |
|---|---|---|---|
| | A | B | C |
| 6 | 0 | 1 | 2 |
| 7 | 0 | 2 | 0 |
| 8 | 0 | 2 | 1 |
| 9 | 0 | 2 | 2 |
| 10 | 1 | 0 | 0 |
| 11 | 1 | 0 | 1 |
| 12 | 1 | 0 | 2 |
| 13 | 1 | 1 | 0 |
| 14 | 1 | 1 | 1 |
| 15 | 1 | 1 | 2 |
| 16 | 1 | 2 | 0 |
| 17 | 1 | 2 | 1 |
| 18 | 1 | 2 | 2 |
| 19 | 2 | 0 | 0 |
| 20 | 2 | 0 | 1 |
| 21 | 2 | 0 | 2 |
| 22 | 2 | 1 | 0 |
| 23 | 2 | 1 | 1 |
| 24 | 2 | 1 | 2 |

When detection results of each nucleic acid array are examined with respect to each complementary nucleic acid, for example, in the case of the complementary nucleic acid corresponding to probe 1, since all the nucleic acid samples A-C are labeled with the green fluorescent label, the combination of pieces of identification information among the nucleic acid samples A-C is "000". In the case of the complementary nucleic acid corresponding to probe 6, the combination of pieces of identification information among the nucleic acid samples A-C is "012". Each complementary nucleic acid has a different combination of pieces of identification information. Therefore, if detection results associated with the pieces of identification information corresponded to the combination, it can be judged that the type and the position of the nucleic acid probe immobilized on the nucleic acid array are correct.

2. Method for Examining Quality of Nucleic Acid Array

Based on the above-described method, one rod of the nucleic acid array is examined before shipment of the nucleic acid array, and it can be utilized as one of the quality control standard thereof.

Nucleic acid arrays to be used for quality examination for confirmation of positions of probes immobilized are desirably prepared from nucleic acid arrays mass-produced from the same rod. In the present method, any nucleic acid array is applicable, but a nucleic acid microarray, which can be produced in a manner in which respective probe spot positions are not physically mixed, is preferred. Such a nucleic acid microarray can be obtained by immobilizing probes to hollow fibers or the like, bundling them together and slicing the bundle. Immobilization of probes to hollow fibers can be evenly performed. Therefore, when determining immobilization positions of nucleic acid probes using microarrays obtained by slicing as described above, examination of the microarrays from the same rod can be conducted with high accuracy and without variation of quality.

Further, when a plurality of nucleic acid arrays cannot be used for confirmation of immobilization positions of probes, a nucleic acid array, which was used for hybridization once, can be reutilized. Specifically, after hybridization, hybrids between nucleic acid probes and complementary nucleic acid samples are dissociated from each other. Hybrids can be dissociated by immersing the nucleic acid array in water or the like and heating it to a given temperature or higher. The dissociated nucleic acid array can be reutilized depending on the immobilization conditions of probes or conditions of remaining signals. In the case of nucleic acid arrays prepared on a dried substrate, reutilization is often not recommended. However, in the case of nucleic acid arrays utilized in the state of constant moistness, since hybrids can be easily dissociated and it is more difficult to remove immobilized probes compared to the case of dried substrates, there is no particular false recognition with respect to, for example, just a piece of identification information regarding the presence or absence of signals.

EXAMPLES

Hereinafter, the present invention will be described in more detail with reference to working examples. The present invention, however, is not limited to the examples described below.

Preparation of Nucleic Acid Array

Synthesis of Nucleic Acid Probes

In order to prepare a nucleic acid array, oligo DNAs set forth in SEQ ID NOs: 1-192 in Table 3 below were synthesized.

TABLE 3

| SEQ ID NO: | Sequence |
|---|---|
| 1 | actgttgacaccataaaagattctgacgaagagctggacaacaatcagatagaagtactggacca |
| 2 | gatcgtcagccaatggatcgtgggcaatggacacgcaactgatctctggcagaactgtagcacct |
| 3 | tcatggcccctctgacctgcactggggagcccgtctcagtgttgagccttttccctctttggctc |
| 4 | cgccatctccactgcatccgatctcattatttcggtggttgcttgggggtgaacaattttgtggc |
| 5 | tatgaagtcatgcgtttaatcacattcgagtgtttcagtgcttcgcagatgtccttgatgctcat |
| 6 | gatattgtggacacggccatgcctatcaccatttgtatagcttattttaacaattgcctgaatcc |
| 7 | gctaaagtccaagagaggatccgagaacgctctaagcctgtccacgagctcaatagggaagcctg |
| 8 | agcctatggtcccggatgacatctgtttaaaaacaagcacaacctgcaacatactttgattacct |
| 9 | tatttggtttcacaatggaggagcgctcatgggggccctatatcacctgtattcagggcctatgt |
| 10 | taatggtgcccatgatgagtttgcatcacctgactataccttacttccgggacgaggagctgtcc |
| 11 | cacaagacacagaatagtttacacactgtgtgggggacggcttctcacgctttgtttactctctt |
| 12 | caaggctaagtttgccggcaggaacttcagaaacccccttggccaagtaagctgtgggcaggcaag |
| 13 | taatacagtgcttcatatcagctctcttcttgcatggacactactgctgaccatatgcccaatca |
| 14 | ctctagttttcagccttgggaggttttattctgacttcctctgattttggcatgtggagacactc |
| 15 | ttccctgtgagtgaaatgccttctagtagtgaaccgtcctcgggagccgactatgactactcag |
| 16 | ggagaatgcaaatatatagagcacctggaagcagtaacatgcaaatgtcagcaagaatatttcgg |
| 17 | gatatacatgctcaaccttcatcggcccacgtgtattgtccgggctcagaatgggaggactccag |
| 18 | gctcaatatgccccaggctatgacaaagtcaaggacatctcagaggtggtcacccctcggttcct |
| 19 | caaacagttcgacactgaccgatcagggaccatttgcagtagtgaactcccaggtgcctttgagg |
| 20 | caactggactatgttgacctctatcttcttcatttcccaatggctctcaagccaggtgagacgcc |
| 21 | aggagagcttctccaaaggctgagggacatttccacagtcaagagcctctttgccaagcgacaac |
| 22 | gaaagggccttgacatcagttcctttgtgtgtactcactgaagcctgcgttggtccagagcggag |
| 23 | ggtggtgatcggcatggatgtggcagcatctgagttctatcgcaatgggaagtacgatcttgact |
| 24 | agcccgttccgcagggactagaggctttcggcttttttgggacagcaactaccttgcttttggaaa |
| 25 | tcttacttctacaggttccttgagcaccaaagatgattcataactctgtataggtgacagctgct |
| 26 | tacgttaaaagctgtgctggatattgcgtgatcacctatatacttggagttggagacaggcacct |
| 27 | tggcttgcttggtgggacctgacgagttggtggcatgggaaggatgtgggtctctagtgccttgc |
| 28 | agatcttgatccttgtcctcgtccaaaaagacgtcagccttacaacgcaatattttctccaaaag |
| 29 | catctccttgtctgaaaacatttcccctgctgttctctttctaacatgttgtggtaaatctgttc |
| 30 | cctttaattccttacttggctatgggtggagggtgagtttgaagaggttctgattttcttgtaa |
| 31 | ggttgagacaactgtcacaagcctcaagacgaaagtaggcggtacgaaccctaatggaggcagtt |
| 32 | cttgtgggcttcaggtgttttcaagcacaacccaccacaacaagcaagtgcattttcagtcgttg |

TABLE 3-continued

| SEQ ID NO: | Sequence |
|---|---|
| 33 | aggagtgaatgtaaaaataaatatcgcttagaatgcaggagaagggtggagaggaggcaggggcc |
| 34 | gtgaaattgtgccttgcctgagtgagcttcataaagcgtaccttgatataccccatcgacctcag |
| 35 | acctgaggcagtatgacatctctgacccacagagaccccgcctcacaggacagctcttcctcgga |
| 36 | ttctcccagcgttaacacaaaatccatgggcagcatgatggcaggtcctctgttgcaaactcagt |
| 37 | cccagaccaaaatgagtgccagcgacccaaactcctccatcttcctcaccgacacggccaagcag |
| 38 | ccaaattgccaaaactcaagtcacctcagtaccatccaggaggctgggtattgtcctgcctctgc |
| 39 | gcttgcagcatggtcttgactgaatgtactgttcctgttagcgttacttctcctgtggtcagtaa |
| 40 | gctgggaactgacataggcttcaattggtggaattcctctttaacaagggctgcaatgccctcat |
| 41 | aggaaggagccttggatctcagcggcctcagagctatagacaccactcagctgttctccctcccc |
| 42 | aagggtgccatggcagctacatattctgctttgaaccgtaatcagtcaccagttttggaaccagt |
| 43 | gctttatgtaaatattctgcagttgttacttaggaagcctggggagggcaggggtgcccatggc |
| 44 | gttgatgcaatcggtttaaacatggctgaacgcgtgtgtacacgggactgacgcaacccacgtgt |
| 45 | cttcagagagctggtagttagtagcatgttgagccaggcctgggtctgtgtctcttttctctttc |
| 46 | gcttaaggactcagaaacaagtcagcgtctggccaacctcaggcaacgggtggagcagtttgcca |
| 47 | acttcaagatcaccctctacgggagaaccaaggagctgacttcggaactaaaggagaacttcatc |
| 48 | cactggtttcaagaatatggaggctggaaggaaataaacattacggtacagacatggagatgtaa |
| 49 | tgccgtggataaattgctcaaggacctggacgccaatggagatgcccaggtggacttcagtgagt |
| 50 | tgctcctattccggactcagacctctgaccctgcaatgctgcctaccatgattggcctcctggca |
| 51 | aaaacaaactggcttgataatcatttgggcagcttgggtaagtacgcaacttacttttccacca |
| 52 | cccaaaatgctctgtcttgagtcatgagaaccatcagttcttgatattgtctagacttgcatcta |
| 53 | gaatactttggcttgaagccggcacacccagggttactgaggacttatgctgcctgacctggtta |
| 54 | cccagatcttcaatgaggagcagtactgtggggattttgactcttcttctctgcaaaagaagag |
| 55 | gacccccctaagttagtcagattactagacagatataaacagatcccctgctgaacagatatacag |
| 56 | ccaaggagaaaggcatgaatcttccctgtcaggctcttacagccacaggcactgtgtctactgtc |
| 57 | ggaggcagccatcataaccattgaatagcatgcaagggtaagaatgagtttttaactgctttgta |
| 58 | gcacaccttggaattcgctttctaaaggaaatcaaatgaatggaggaacttccaaacaccactt |
| 59 | gccactgcagctaccgtagaatggcattttatatgtaccttgtcacccacttctgtttacttttt |
| 60 | ggcctcctcaatttgcagatcccccaagtacaggcgctaattgttgtgataatttgtaattgtga |
| 61 | tcagcggctgttgattcaaggtcaacattgaccattggaggagtggtttaagagtgccaggcgaa |
| 62 | gaaggatattactaccgtcaagtctttgaacgccattacccaggccgggctgactggctgagcca |
| 63 | ctacattataactcacagcattgttccattgcaggttttgcaatgtttgggggtaaagacagtag |
| 64 | cttttatttaagttgtgattacctgctgcatgaaaagtggcatgggggaccctgtgcatctgtgc |
| 65 | gatatcgaagagcagggggttgtgaatttccaggtacttggacttttttgtagaaggagagagaag |
| 66 | ccagaatcgctagactaagaattaggtggctacagatggtagaactaaacaataagcaagagaca |
| 67 | gaaatggcttctatgatcagaactgggaaaacagtgaatcttatggtggaagaggttctcagcaa |
| 68 | gcaatcacaatgccagatggtgtttatgggctatttgtgtaagtaagtggtaagatgctatgaag |
| 69 | ggaagattcccggagggaaactgtgaatgcttctgatttagcaatgctgtgaataaaaagaaaga |
| 70 | acctacggcaacagatacaagaacgtgaagctccctgacgcctacgagcgcctcatcctggacgt |
| 71 | gcttctaggcggactatgacttagttgcgttacacccttttcttgacaaaacctaacttgcgcaga |

TABLE 3-continued

| SEQ ID NO: | Sequence |
|---|---|
| 72 | acggaggagcatgcccgacagcagcacaatgagaggctacgcaagcagtttggagcccaggccaa |
| 73 | agagtgccttttcgagactggcagggacgaggacaaatatggatgaggtggagagtgggaagcag |
| 74 | acactgttgccctggctgtattcataagattccagctccttcaggtgtttgattccagcatgtag |
| 75 | attgaggctcttggaaggagtcaggcaaggattgtgcttcccccattatacaggtgacaaaactg |
| 76 | attcaagcgcacgagtgggtgccgctgtggctactgcggtattcggtcattgtgaaaagtagagg |
| 77 | tgtgactttcaagctactcaccctgtaatggatcttaaagcattccccaaagataacatgctttg |
| 78 | attcatcaattatgtgaagaattgcttccggatgactgaccaagaggctattcaagatctctggc |
| 79 | tatccaagttgtccttgaattgtctaaccatggacataaacagttgtctcccttctactgtgtag |
| 80 | ggaaaacagccagaagccaccttgacacttttgaacatttccagttctgtagagtttattgtcaa |
| 81 | ggtggaggtgggatttagccaggaaaggggtgagagtgattgtgttgtgggcgaggaggcgttt |
| 82 | attgtggggtcgatcatgaatgtccgaagagtggccttttcccgtagccctgcgccccttttct |
| 83 | ttgtgcagcaatggccaagatcaaggctcgagatcttcgcgggaagaagaaggaggagctgctga |
| 84 | aagcaaagagaagactttgtacacactgtcaccagggttatttgcatccaagggagctggaattg |
| 85 | cgtgcccgaaatcaggtggtgataagagcagagcccccaactctgtgccttgtgtgcggatctctg |
| 86 | tctagaactgacctaccacaagcatccaccaaaggagtttgggattgagttttgctgctgtgcag |
| 87 | ggtctcttccagattgctcttctgccgaattatttgtatctattccgagctgattatgtaatagg |
| 88 | gctcttgatgagaggctcgctttaaagaagcccaaagcgtgtgcttatccaaggggttcagctat |
| 89 | ctgcttcataggtgttctgcatttgaggtgtagtgaaatctttgctgttcaccagatgtaatgtt |
| 90 | tgaagtagtagccacagtacaacactgactgctcagacacatttaggttcagggtggacctttat |
| 91 | ttgtggtgagacgtcatagtcttcatgagaacgtgggggtgaatttcatgaagggaactatagt |
| 92 | gactctatcgtggtttatctcttaattacattcgctgtattccctctcaagcagtggcttttaca |
| 93 | gaagtcgagatgactttgatcattggtaacttgggcctgggccagacaaagtataaaacttacaa |
| 94 | tctgtctatacctgccccatctgagcacccattgctcaccatcagatcaacctttgattttacat |
| 95 | ccagtttctgtatagaatcgcacaagtggtttatggagtgtttggattgtaattataaatggttc |
| 96 | ctagcctgcattgagcttgcatgcttgcataagagcttaagaaccattgatttaatgtaataggg |
| 97 | gcctgcatccggagaattgcctctacctggaccttttgtctcacacagcagtaccctgacctgct |
| 98 | cctcacacccaccccatgcactcaaagattggattttacagctacttgcaattcaaaattcaga |
| 99 | gggccatctcttggagtgacaaagctgggatcaaggatagggagttgtaacagagcagtgccaga |
| 100 | gcctgaactagccaatcagatcaactctgtcttgggcgtttgaactcagggagggaggcccttgg |
| 101 | ctgacaagtcttaatcaactaggcgagaggcaacttctttcagtagtcaagtggtctaaatcatt |
| 102 | caagttcagctccacgtgtgccatcagtggatccgatccgtccagccatggcttcctattccaag |
| 103 | gcaagtgtacagatctgtgtagaggaatgtgtgtatatttacctcttcgtttgctcaaacatgag |
| 104 | ctgaccctgaagttttcctaccccaaggagagttactcgacagtccataagtcaactgttgtgtg |
| 105 | tcacttgctgaacgccgtgaccgatgctttggtttgggtgattgccaagagcggcatctcctccc |
| 106 | ctgttgtcctcccttgggcggctgagagcccagctgacatggaaatacagttgttggcctccg |
| 107 | caaaaatgaccccccatttgtgtgacttcattgagacacattacctgaatgagcaggtgaaagcca |
| 108 | ggcctgggtaggatcatgtatacggtatttgaacatacattccatgtacgagaaggagatgaaca |
| 109 | gctattattttctttaaagaatgctgggtgttgcatttctggaccctccacttcaatctgagaag |

TABLE 3-continued

| SEQ ID NO: | Sequence |
|---|---|
| 110 | ctctttctgcatggttgtgtccctagtcctaagctttggttctttagggtgactgtggtaagaag |
| 111 | attgcgaagaacctgctctccgcgcctctcggtgctccaaatggacatcacgaagccagtgcaga |
| 112 | tcatgctaacgcagcagttgcaaacattttgaagagagaccgtcgggggctgaggggcaacgaag |
| 113 | gacacgtgatgggaagctggtgtctgagtcctctgacgtcctgcccaagtgaacagctgcggcag |
| 114 | tctgtatgacaacccgggatcgtttgcaagtaactgaatccattgcgacattgtgaaggcttaaa |
| 115 | tgctgtgtttactctcccgtgtgccttcgcgtccgggttgggagcttgctgtgtctaacctccaa |
| 116 | ttgtatcacggattacaatgaacgcagtgcagagccccaaagctcaggctattgttaaatcaata |
| 117 | gcctacatgacacagttggatttattctgccaaacctgtgtaggcattttataagctacatgttc |
| 118 | tagtggggactagtgaatgacttgacctgtgacctcaatacaataaatgtgatcccccacccaaa |
| 119 | cagcacaaggaggatgtgatatgtgggggagtgagcactgggttgggagccgggtcctggtttcc |
| 120 | cactgttagatagttggaaaggggaaattctgtttaagcgaaagtggtatcatcctaggtaagct |
| 121 | cttccaagctctgcttcctcagtttccaaaatggaaccacctcacctccgcagcacccgacttac |
| 122 | cccctttgccattgatcaagccatattcaggtcctaggttgccacctgatagatactgcttaaca |
| 123 | cgacgacaccgttcgtggggtcccctggtgcttctatcctaataccatcgacgtccctccagaag |
| 124 | tttgggagagacttgttttggatgcccctaatccccttctccctgcactgtaaaatgtgggat |
| 125 | gcctcccttggtctgcccagccctcggttagccctgcctgaatcagtagatacttgaacgagtcc |
| 126 | ctgcgccctagctgggatctggtacctggactaggctaattacagcttctccccaacaggaaac |
| 127 | aactcctgtacttgaagctgagacctcatatgacgtggccttcgtgttgtcagagagtgtctgga |
| 128 | ctgagaggggaagcggccctaagggagtgtctaagaacaaaagcgacccattcagagactgtccc |
| 129 | tgcatgaatgaagaccctgcaaagcgacccaaatttgacatgattgtgcctatccttgagaagat |
| 130 | acagctgtagcaactttgtgtctgaagatgactcggaaacccagtccgtgtccagctttagttca |
| 131 | tgccctgtggaatgggctcaaggttcctgagacacccgattcctgcccaaacagctgtatttata |
| 132 | gcagaagcagacctagaccctagcgttccccctttatgactctcttcagacttatgcctatgaggg |
| 133 | ccagacaaaatttgagaatacataaacaacgcattgccacggaaacatacagaggatgccttttc |
| 134 | cagctctagaggtcacagtatcctcgtttgaaagataattaagatcccccgtggagaaagcagtg |
| 135 | tccaaggctcaccgcagaagcagtagcagcggggaccaatcatcagactccttgaactcccccac |
| 136 | ccacatgttaaccctctagctgataatgcaaacactaactgggggatttattttataagggctct |
| 137 | gggcctttccaagattgctgtttttgttttggagcttcaagactttgcatttcctagtatttctg |
| 138 | aaactgctatagcctaagcggctgtttactgcttttcattagcagttgctcacatgtctttgggt |
| 139 | tgaatgagatgcgtgaccagtacgagcagatggcagagaaaaaccgcagagacgctgagacctgg |
| 140 | tgatgctctgcgaagggctcttcgtggcagacgtcaccgatttcgagggctggaaggctgcgatt |
| 141 | gggggtgctctttggacactggattatgaggaatggataaatggatgagctagggctctgggggt |
| 142 | tgctgtggcttcaccaactatacggattttgaggactcaccctacttcaaagagaacagtgcctt |
| 143 | gaggataacattggcgggaggggagttaactggcaggcatggcaaggttgcatatgtaataaagt |
| 144 | tgatgatgaggaagaagaagaagaaggggctcatggggccgtgggaacccaaggttccatagtc |
| 145 | ccaggacaaaggccgcttgaactctaccgtgccacgttttatgccgctgagataatgtgtggac |
| 146 | tccatttctctgagggacctttagttggctctgtgggactgttccggatgggcctctgggtcact |
| 147 | agcagctgctagggggtgtccaaggagcagagaaaactactagatgtgaacttgaagaaggttg |
| 148 | gtggttggtgtcctgctcatcatcctgattgtgctgctggtcgtcttctccctcagagcagtga |

TABLE 3-continued

| SEQ ID NO: | Sequence |
|---|---|
| 149 | aatctgcattctgtcaggcacccgtagaaagacctcagtacatgctttgcactctcctttgctcc |
| 150 | tacatccagtaccaaggcttccgggtccagctggaatccatgaagaagctgagtgacctggaggc |
| 151 | ccaaattcaagatacaggtatccccgttttttacaacagatgttcatgccctgcttcatgcaatt |
| 152 | gaattggatttgaagaactcgactttatgtgatcatggtattggtatacatgggggtggagaac |
| 153 | acgattttcttctgtagaatgtttgacttcgtattgacccttatctgtaaaacacctatttggga |
| 154 | gcacgcattttttgttgccttggttttacctgtagactgtggaactattttaccttaagacctgaa |
| 155 | gtggaaggactgattgagaatgttccaatccaaatgaatgcatcacaacttacaatgctgctcat |
| 156 | gctgctctcattggaattgcaggatctggctactgtgtcattgtggcagcccttggcttagcaga |
| 157 | caaatttaataaggaaccatgtaatggtagcagtacctccctaaagcattttgaggtaggggagg |
| 158 | aacaaaaatctgggaatggtctgccgaaaaccgaccgaccggttgattggccaccgcttgtcct |
| 159 | tcctaacctgccggggtcattccccaccaaacaccccatactaaggagccatgagccacctggac |
| 160 | cggagggaactgcagggagaccaacttatttagagcgaattggacatggataaaaaccccagtgg |
| 161 | tgctgggtaccaggactcacctctgacaagcaggagaaggtaagggcccggtcagctccaaggag |
| 162 | gccaaaggaagtctaaggaattagtagtgttcccatcacttgtttggagtgtgctattctaaaag |
| 163 | cataaagttgctggccagcttttacctcttgcatataatctgttgaagaggaatctgtttgcaga |
| 164 | gcaaactcatggatggctcttataccaggagaagataaggtatgccagagtgtatttgagagaaa |
| 165 | ctgttcagatgatctttcattcaatgtgttcctgttgggcgttactagaaactatggaaaactgg |
| 166 | tgggtacactttgtaccagtgtcggcctccactgatgctggtgctcaggcacctctgtccaagga |
| 167 | accagggtaccctgtcttggtggttaggggccacttttcctttgaggctctagtggaggtggatg |
| 168 | ggttgagaagagcttttcggacctgttactaccccaagctgtgtaatatacttgtataacagaaa |
| 169 | ctaaggccattgacgtggcctgcgatctcagtgacaatgatctgcttctggatctcactgttgcc |
| 170 | tgacagccaccgggtcatcaccttcgcaaaccaggacgactacatatcattccggcaccatgtgt |
| 171 | ctccagcatctcaactccgtctgtctactgtgtgagacttcggcggaccattaggaatgagatcc |
| 172 | cgattacagggacaacagcagttgatacaccaaaatcggcaagctatcttaaaccagtttgcagc |
| 173 | agaaggagcaatggtacgctggcatcaaccccctcggacggtatcaactcagaggtcctggaagcc |
| 174 | cccaaaggatggtcacacaccagcactttatacacttctggctcacaggaaagtgtctgcagta |
| 175 | atgccttgtaccccaccgtgcaggttgtggccggttttctccgcaggttgaacatggaaataaa |
| 176 | ttggtgcaagtcttgggagcgtgatctagattacactgcaccattcccaagttaatcccctgaaa |
| 177 | ttccatccactgccatgaccctgttccctgtctataaatccccagttttccatggtatattcag |
| 178 | gtatattaaagcaccaaattcatgtacagcatgcatcacggatcaatagactgtacttattttcc |
| 179 | ggcttcggacaaaatatctctgagttctgtgtattttcagtcaaaactttaaacctgtagaatca |
| 180 | agtggagctgtttgacttggagaataacccagagtacgtgtccagcggagggggctttggaccgg |
| 181 | tgagaactcgtggtacttcagtgtccctccccctgtattgtgacaaggtaattctgtggtatcag |
| 182 | ctaatacgatgcatatactgaagggcaaggactttgaccatgtcaattttcagccgagaatggtc |
| 183 | accaccatggttacagcggatgccccgagactctgcttggtaaacgtggcagagcagaatgggag |
| 184 | aaggcagagagtcagacccttcaatggaaggagagtgcttgggatcgattatgtgacttaaagtc |
| 185 | gtctgagcttctttagctaggctaaaacaccttggcttgttattgcctctactttgattctgata |
| 186 | gcatttaattcaaagagaggggagcatccattattggtacatgtgggcttttaaaaactccatcc |

TABLE 3-continued

| SEQ ID NO: | Sequence |
|---|---|
| 187 | gcaccaacatgtaaccggcatgtttccagcagaagacaaaaagacaaacatgaaagtctagaaat |
| 188 | atgcctgcccagttccctttttatttgcagaagctgtgagttttgttcacaattaggttcctagg |
| 189 | gtgccactagttaaatgccgaattctcatctggatgttaccatcaaacatcagtacacttgtcat |
| 190 | cagctgcctgttttgcatggtatttgcaaaaatgcctcttgcgtgaggaaatcttttaccattttt |
| 191 | gacaatgctgatggaagaccagactggaaagtggatcgactcctccttcattgattctaaattca |
| 192 | ggttagttgatcaagaatttttggggtgggggttgcggagaaatcaagtttaaaattccttctgat |

Production of Nucleic Acid Array

A hollow-fiber bundle was produced utilizing an arrangement fixing tool shown in FIG. 1. In FIG. 1, x, y and z are axes which are at right angles to one another and constitute three-dimensional coordinate. The direction of axis x corresponds to the longitudinal direction of fibers.

Firstly, 2 porous plates (21) having the thickness of 0.1 mm, in which 228 pores (11) (12 vertical rows×19 horizontal rows) having the diameter of 0.32 mm were provided with the center-to-center spacing of the pores of 0.42 mm, were prepared. These porous plates were overlapped with each other, and through each of the pores, one hollow fiber (31) made of polycarbonate (manufactured by Mitsubishi Engineering-Plastics Corporation; 1% by mass of carbon black was added) was passed.

The positions of 2 porous plates were moved under the conditions where 0.1 N of tensile force was applied to each fiber in the direction of axis X, and the porous plates were fixed to the positions at 20 mm and 100 mm from one end portion of the hollow fibers, respectively. That is, the distance between the porous plates was 80 mm.

Next, three faces surrounding the open space between the porous plates were surrounded by plate-like bodies (41). Thus, a container with only the upper side thereof being open was obtained.

Next, a resign material was poured into the container from the upper side thereof. The resin used was prepared by adding 2.5% by mass of carbon black to the total weight of polyurethane resin adhesive (Nippon Polyurethane Industry, Co., Ltd., NIPPOLAN 4276, CORONATE 4403). The resin was cured by being allowed to stand at 25° C. for one week. After that, the porous plates and the plate-like bodies were removed to obtain a hollow-fiber bundle.

Next, gel precursor polymerizable solutions comprising a monomer and an initiator mixed in the mass ratio shown in Table 4 were prepared for respective nucleic acid probes to be immobilized on the array.

TABLE 4

| Composition | Mass Ratio (Nucleic acid probe; Concentration) |
|---|---|
| N,N-dimethylacrylamide | 3.42% |
| N,N-methylenebisacrylamide | 0.38% |
| 2,2'-azobis[2-(2-imidazoline-2-yl) propane] dihydrochloride (VA-044) | 0.1% |
| Water | 96.2% |
| Solution of Nucleic acid probe | 5 pmol/l |

Next, containers containing the gel precursor polymerizable solutions and the hollow-fiber bundle prepared above were placed in a desiccator in order to fill hollow portions of the hollow fibers of the bundle corresponding to the positions shown in FIG. 2 with the respective gel precursor polymerizable solutions comprising the respective nucleic acid probes as prepared above. After the pressure in the desiccator was reduced, the end portion of the hollow-fiber bundle in which each fiber is not sealed was immersed in the predetermined gel precursor polymerizable solutions in the containers. The desiccator was filled with nitrogen gas, and the gel precursor polymerizable solutions comprising capture probes were introduced into the hollow portions of the hollow fibers. Next, the container was heated to 70° C. to perform polymerization reaction for 3 hours.

In this way, the hollow-fiber bundle, in which the nucleic acid probes were held in the hollow portions of the hollow fibers via the gel-like material, was obtained.

Next, the obtained hollow-fiber bundle was sliced in the direction perpendicular to the longitudinal direction of the fibers using a microtome to obtain 300 thin sheets (nucleic acid arrays) having the thickness of 0.25 mm.

The nucleic acid arrays were prepared to have probe positions shown in FIG. 2. In FIG. 2, the numbers represent SEQ ID NOs of probes, and probes having nucleotide sequences set forth in respective SEQ ID NOs are arrayed on the nucleic acid arrays. B represents a spot where no nucleic acid probe is present.

Preparation of Groups of Nucleic Acid Samples for Identification of Immobilization Positions of Nucleic Acid Probes Nucleic acid samples (oligo DNAs) for identification of probe positions on the nucleic acid array prepared above were prepared as follows. These nucleic acid samples comprise a portion complementary to a part of 3' terminal side of each corresponding probe, and 5' terminal side of the nucleic acid samples comprises a nucleotide sequence consisting of the GT repeat sequence, which is complementary to SEQ ID NO: 385. SEQ ID NO: 385 was prepared with oligo DNA whose 5' terminal side is Cy5-labeled in the concentration of 100 pmol/µl.

Regarding the correspondence relationship between the probe sequences and the sequences of the nucleic acid samples for confirmation of probe immobilization positions comprising complementary chains thereof, SEQ ID NOs: 1, 2, . . . and 192 correspond to SEQ ID NOs: 193, 194, . . . and 384, respectively (Tables 3 and 5). A part of each sequence in the table of probes above is complementary to a part of each corresponding sequence in Table 5. Each analyte has a sequence which forms a double strand with a corresponding sequence of a probe. For example, a sequence represented by small letters in the nucleotide sequence of SEQ ID NO: 193 in Table 5 is complementary to the underlined part of the nucleotide sequence set forth in SEQ ID NO: 1 in Table 3 (positions 33-65 of the sequence), and can form a double strand therewith.

TABLE 5

| SEQ ID NO: | Sequence |
|---|---|
| 193 | CTCTCTCTCTCTCTCTCTCTCTCTCTCtggtccagtacttctatctgattgttgtccagc |
| 194 | CTCTCTCTCTCTCTCTCTCTCTCTCTCaggtgctacagttctgccagagatcagttg |
| 195 | CTCTCTCTCTCTCTCTCTCTCTCTCTCgagccaaagagggaaaaggctcaacactg |
| 196 | CTCTCTCTCTCTCTCTCTCTCTCTCTCgccacaaaattgttcaccccccaagcaacc |
| 197 | CTCTCTCTCTCTCTCTCTCTCTCTCTCatgagcatcaaggacatctgcgaagcactg |
| 198 | CTCTCTCTCTCTCTCTCTCTCTCTCTCggattcaggcaattgttaaaataagctatacaaatggtgatagg |
| 199 | CTCTCTCTCTCTCTCTCTCTCTCTCTCcaggcttccctattgagctcgtggac |
| 200 | CTCTCTCTCTCTCTCTCTCTCTCTCTCaggtaatcaaagtatgttgcaggttgtgcttgttttttaaacag |
| 201 | CTCTCTCTCTCTCTCTCTCTCTCTCTCacataggccctgaatacaggtgatataggc |
| 202 | CTCTCTCTCTCTCTCTCTCTCTCTCTCggacagctcctcgtcccggaag |
| 203 | CTCTCTCTCTCTCTCTCTCTCTCTCTCaagagagtaaacaaagcgtgagaagccgtcc |
| 204 | CTCTCTCTCTCTCTCTCTCTCTCTCTCcttgcctgcccacagcttacttggc |
| 205 | CTCTCTCTCTCTCTCTCTCTCTCTCTCtgattgggcatatggtcagcagtagtgtcc |
| 206 | CTCTCTCTCTCTCTCTCTCTCTCTCTCgagtgtctccacatgccaaaatcagaggaag |
| 207 | CTCTCTCTCTCTCTCTCTCTCTCTCTCctgagtagtcatagtcggctcccgag |
| 208 | CTCTCTCTCTCTCTCTCTCTCTCTCTCccgaaatattcttgctgacatttgcatgttactgcttc |
| 209 | CTCTCTCTCTCTCTCTCTCTCTCTCTCctggagtcctcccattctgagccc |
| 210 | CTCTCTCTCTCTCTCTCTCTCTCTCTCaggaaccgaggggtgaccactc |
| 211 | CTCTCTCTCTCTCTCTCTCTCTCTCTCcctcaaaggcacctgggagttcactac |
| 212 | CTCTCTCTCTCTCTCTCTCTCTCTCTCggcgtctcacctggcttgagagc |
| 213 | CTCTCTCTCTCTCTCTCTCTCTCTCTCgttgtcgcttggcaaagaggctcttgac |
| 214 | CTCTCTCTCTCTCTCTCTCTCTCTCTCctccgctctggaccaacgcagg |
| 215 | CTCTCTCTCTCTCTCTCTCTCTCTCTCagtcaagatcgtacttcccattgcgatagaactc |
| 216 | CTCTCTCTCTCTCTCTCTCTCTCTCTCttttccaaaagcaaggtagttgctgtcccaaaaagc |
| 217 | CTCTCTCTCTCTCTCTCTCTCTCTCTCagcagctgtcacctatacagagttatgaatcatctttg |
| 218 | CTCTCTCTCTCTCTCTCTCTCTCTCTCaggtgcctgtctccaactccaagtatatagg |
| 219 | CTCTCTCTCTCTCTCTCTCTCTCTCTCgcaaggcactagagacccacatccttc |
| 220 | CTCTCTCTCTCTCTCTCTCTCTCTCTCcttttggagaaaatattgcgttgtaaggctgacgtc |
| 221 | CTCTCTCTCTCTCTCTCTCTCTCTCTCgaacagatttaccacaacatgttagaaagagaacagcag |
| 222 | CTCTCTCTCTCTCTCTCTCTCTCTCTCttacaagaaaatcagaacctcttcaaactcaccctcc |
| 223 | CTCTCTCTCTCTCTCTCTCTCTCTCTCaactgcctccattagggttcgtaccgc |
| 224 | CTCTCTCTCTCTCTCTCTCTCTCTCTCcaacgactgaaaatgcacttgcttgttgtggtg |
| 225 | CTCTCTCTCTCTCTCTCTCTCTCTCTCggcccctgcctcctctccac |
| 226 | CTCTCTCTCTCTCTCTCTCTCTCTCTCctgaggtcgatggggtatatcaaggtacg |
| 227 | CTCTCTCTCTCTCTCTCTCTCTCTCTCtccgaggaagagctgtcctgtgagg |
| 228 | CTCTCTCTCTCTCTCTCTCTCTCTCTCactgagtttgcaacagaggacctgccatc |
| 229 | CTCTCTCTCTCTCTCTCTCTCTCTCTCctgcttggccgtgtcggtgagg |
| 230 | CTCTCTCTCTCTCTCTCTCTCTCTCTCgcagaggcaggacaatacccagcc |
| 231 | CTCTCTCTCTCTCTCTCTCTCTCTCTCttactgaccacaggagaagtaacgctaacagg |

TABLE 5-continued

| SEQ ID NO: | Sequence |
|---|---|
| 232 | CTCTCTCTCTCTCTCTCTCTCTCTCTCTatgagggcattgcagcccttgttaaagagg |
| 233 | CTCTCTCTCTCTCTCTCTCTCTCTCTCTggggagggagaacagctgagtgg |
| 234 | CTCTCTCTCTCTCTCTCTCTCTCTCTCTactggttccaaaactggtgactgattacggttc |
| 235 | CTCTCTCTCTCTCTCTCTCTCTCTCTCTgccatggggcaccccctgccc |
| 236 | CTCTCTCTCTCTCTCTCTCTCTCTCTCTacacgtgggttgcgtcagtcccg |
| 237 | CTCTCTCTCTCTCTCTCTCTCTCTCTCTgaaagagaaaagagacacagacccaggcc |
| 238 | CTCTCTCTCTCTCTCTCTCTCTCTCTCTtggcaaactgctccacccgttgcc |
| 239 | CTCTCTCTCTCTCTCTCTCTCTCTCTCTgatgaagttctcctttagttccgaagtcagctc |
| 240 | CTCTCTCTCTCTCTCTCTCTCTCTCTCTtacatctccatgtctgtaccgtaatgtttatttccttcc |
| 241 | CTCTCTCTCTCTCTCTCTCTCTCTCTCTactcactgaagtccacctgggcatctc |
| 242 | CTCTCTCTCTCTCTCTCTCTCTCTCTCTgccaggaggccaatcatggtaggc |
| 243 | CTCTCTCTCTCTCTCTCTCTCTCTCTCTggtggaaaagtaagttgcgtacttacccaagc |
| 244 | CTCTCTCTCTCTCTCTCTCTCTCTCTCTagatgcaagtctagacaatatcaagaactgatggttctc |
| 245 | CTCTCTCTCTCTCTCTCTCTCTCTCTCTaaccaggtcaggcagcataagtcctcag |
| 246 | CTCTCTCTCTCTCTCTCTCTCTCTCTCTctcttcttttgcagagaagaaagagtcaaaatcccc |
| 247 | CTCTCTCTCTCTCTCTCTCTCTCTCTCTctgtatatctgttcagcaggggatctgtttatatctg |
| 248 | CTCTCTCTCTCTCTCTCTCTCTCTCTCTgacagtagacacagtgcctgtggctg |
| 249 | CTCTCTCTCTCTCTCTCTCTCTCTCTCTacaaagcagttaaaaactcattcttacccttgcatgctattc |
| 250 | CTCTCTCTCTCTCTCTCTCTCTCTCTCTaagtggtgtttggaaagttcctccattcatttgatttcc |
| 251 | CTCTCTCTCTCTCTCTCTCTCTCTCTCTaaaaagtaaacagaagtgggtgacaaggtacatataaaatgcc |
| 252 | CTCTCTCTCTCTCTCTCTCTCTCTCTCTcacaattacaaattatcacaacaattagcgcctgtacttgg |
| 253 | CTCTCTCTCTCTCTCTCTCTCTCTCTCTttcgcctggcactcttaaaccactcctc |
| 254 | CTCTCTCTCTCTCTCTCTCTCTCTCTCTggctcagccagtcagcccgg |
| 255 | CTCTCTCTCTCTCTCTCTCTCTCTCTCTctactgtcttaccccccaaacattgcaaaacctg |
| 256 | CTCTCTCTCTCTCTCTCTCTCTCTCTCTgcacagatgcacagggtccccc |
| 257 | CTCTCTCTCTCTCTCTCTCTCTCTCTCTccttctctctccttctacaaaaagtccaagtacctg |
| 258 | CTCTCTCTCTCTCTCTCTCTCTCTCTCTtgtctcttgcttattgtttagttctaccatctgtagcc |
| 259 | CTCTCTCTCTCTCTCTCTCTCTCTCTCTttgctgagaacctcttccaccataagattcactg |
| 260 | CTCTCTCTCTCTCTCTCTCTCTCTCTCTcttcatagcatcttaccacttacttacacaaatagccc |
| 261 | CTCTCTCTCTCTCTCTCTCTCTCTCTCTtcttttcttttttattcacagcattgctaaatcagaagcattcacag |
| 262 | CTCTCTCTCTCTCTCTCTCTCTCTCTCTacgtccaggatgaggcgctcgtag |
| 263 | CTCTCTCTCTCTCTCTCTCTCTCTCTCTctgcgcaagttaggttttgtcaagaaagggtg |
| 264 | CTCTCTCTCTCTCTCTCTCTCTCTCTCTttggcctgggctccaaactgcttgc |
| 265 | CTCTCTCTCTCTCTCTCTCTCTCTCTCTctgcttcccactctccacctcatcc |
| 266 | CTCTCTCTCTCTCTCTCTCTCTCTCTCTctacatgctggaatcaaacacctgaaggagc |
| 267 | CTCTCTCTCTCTCTCTCTCTCTCTCTCTcagttttgtcacctgtataatgggggaagcac |
| 268 | CTCTCTCTCTCTCTCTCTCTCTCTCTCTcctctacttttcacaatgaccgaataccgcag |
| 269 | CTCTCTCTCTCTCTCTCTCTCTCTCTCTcaaagcatgttatctttggggaatgctttaagatccattac |

TABLE 5-continued

| SEQ ID NO: | Sequence |
|---|---|
| 270 | CTCTCTCTCTCTCTCTCTCTCTCTCTCgccagagatcttgaatagcctcttggtcag |
| 271 | CTCTCTCTCTCTCTCTCTCTCTCTCTCctacacagtagaagggagacaactgtttatgtcc |
| 272 | CTCTCTCTCTCTCTCTCTCTCTCTCTCttgacaataaactctacagaactggaaatgttcaaaagtgtcaag |
| 273 | CTCTCTCTCTCTCTCTCTCTCTCTCTCaaacgcctcctcgcccacaacacaatc |
| 274 | CTCTCTCTCTCTCTCTCTCTCTCTCTCagaaaggggcgcagggctacg |
| 275 | CTCTCTCTCTCTCTCTCTCTCTCTCTCtcagcagctcctccttcttcttcccg |
| 276 | CTCTCTCTCTCTCTCTCTCTCTCTCTCcaattccagctcccttggatgcaaataaccc |
| 277 | CTCTCTCTCTCTCTCTCTCTCTCTCTCcagagatccgcacacaaggcacagag |
| 278 | CTCTCTCTCTCTCTCTCTCTCTCTCTCctgcacagcagcaaaactcaatcccaaactc |
| 279 | CTCTCTCTCTCTCTCTCTCTCTCTCTCcctattacataatcagctcggaatagatacaaataattcggc |
| 280 | CTCTCTCTCTCTCTCTCTCTCTCTCTCatagctgaacccctttggataagcacacgc |
| 281 | CTCTCTCTCTCTCTCTCTCTCTCTCTCaacattacatctggtgaacagcaaagatttcactacacc |
| 282 | CTCTCTCTCTCTCTCTCTCTCTCTCTCataaaggtccaccctgaacctaaatgtgtctgag |
| 283 | CTCTCTCTCTCTCTCTCTCTCTCTCTCactatagttccccttcatgaaattcacccccac |
| 284 | CTCTCTCTCTCTCTCTCTCTCTCTCTCtgtaaaagccactgcttgagagggaatacagc |
| 285 | CTCTCTCTCTCTCTCTCTCTCTCTCTCttgtaagttttatactttgtctggcccaggccc |
| 286 | CTCTCTCTCTCTCTCTCTCTCTCTCTCatgtaaaatcaaaggttgatctgatggtgagcaatggg |
| 287 | CTCTCTCTCTCTCTCTCTCTCTCTCTCgaaccatttataattacaatccaaacactccataaaccacttgtg |
| 288 | CTCTCTCTCTCTCTCTCTCTCTCTCTCccctattacattaaatcaatggttcttaagctcttatgcaagc |
| 289 | CTCTCTCTCTCTCTCTCTCTCTCTCTCagcaggtcagggtactgctgtgtgag |
| 290 | CTCTCTCTCTCTCTCTCTCTCTCTCTCtctgaattttgaattgcaagtagctgtaaaatccaatctttgagt |
| 291 | CTCTCTCTCTCTCTCTCTCTCTCTCTCtctggcactgctctgttacaactccctatc |
| 292 | CTCTCTCTCTCTCTCTCTCTCTCTCTCccaagggcctccctccctgag |
| 293 | CTCTCTCTCTCTCTCTCTCTCTCTCTCaatgatttagaccacttgactactgaaagaagttgcctc |
| 294 | CTCTCTCTCTCTCTCTCTCTCTCTCTCcttggaataggaagccatggctggacg |
| 295 | CTCTCTCTCTCTCTCTCTCTCTCTCTCctcatgtttgagcaaacgaagaggtaaatatacacacattc |
| 296 | CTCTCTCTCTCTCTCTCTCTCTCTCTCcacacaacagttgacttatggactgtcgagtaac |
| 297 | CTCTCTCTCTCTCTCTCTCTCTCTCTCgggaggagatgccgctcttggc |
| 298 | CTCTCTCTCTCTCTCTCTCTCTCTCTCcggaggccaacaactgtatttccatgtcag |
| 299 | CTCTCTCTCTCTCTCTCTCTCTCTCTCtggctttcacctgctcattcaggtaatgtgtc |
| 300 | CTCTCTCTCTCTCTCTCTCTCTCTCTCtgttcatctccttctcgtacatggaatgtatgttcaaatac |
| 301 | CTCTCTCTCTCTCTCTCTCTCTCTCTCcttctcagattgaagtggagggtccagaaatg |
| 302 | CTCTCTCTCTCTCTCTCTCTCTCTCTCcttcttaccacagtcaccctaaagaaccaaagc |
| 303 | CTCTCTCTCTCTCTCTCTCTCTCTCTCctgcactggcttcgtgatgtccatttgg |
| 304 | CTCTCTCTCTCTCTCTCTCTCTCTCTCcttcgttgcccctcagcccc |
| 305 | CTCTCTCTCTCTCTCTCTCTCTCTCTCctgccgcagctgttcacttgggc |
| 306 | CTCTCTCTCTCTCTCTCTCTCTCTCTCttttaagccttcacaatgtcgcaatggattcagttacttg |
| 307 | CTCTCTCTCTCTCTCTCTCTCTCTCTCttggaggttagacacagcaagctcccaac |
| 308 | CTCTCTCTCTCTCTCTCTCTCTCTCTCtattgatttaacaatagcctgagctttggggctctg |

TABLE 5-continued

| SEQ ID NO: | Sequence |
|---|---|
| 309 | CTCTCTCTCTCTCTCTCTCTCTCTCTCgaacatgtagcttataaaatgcctacacaggtttggc |
| 310 | CTCTCTCTCTCTCTCTCTCTCTCTCTCtttgggtgggggatcacatttattgtattgaggtc |
| 311 | CTCTCTCTCTCTCTCTCTCTCTCTCTCggaaaccaggacccggctccc |
| 312 | CTCTCTCTCTCTCTCTCTCTCTCTCTCagcttacctaggatgataccactttcgcttaaacag |
| 313 | CTCTCTCTCTCTCTCTCTCTCTCTCTCgtaagtcgggtgctgcggaggtg |
| 314 | CTCTCTCTCTCTCTCTCTCTCTCTCTCtgttaagcagtatctatcaggtggcaacctagg |
| 315 | CTCTCTCTCTCTCTCTCTCTCTCTCTCcttctggagggacgtcgatggtattagg |
| 316 | CTCTCTCTCTCTCTCTCTCTCTCTCTCatcccacattttacagtgcaggggagaagg |
| 317 | CTCTCTCTCTCTCTCTCTCTCTCTCTCggactcgttcaagtatctactgattcaggcag |
| 318 | CTCTCTCTCTCTCTCTCTCTCTCTCTCgttcctgttggggagaagctgtaattagcc |
| 319 | CTCTCTCTCTCTCTCTCTCTCTCTCTCtccagacactctctgacaacacgaaggc |
| 320 | CTCTCTCTCTCTCTCTCTCTCTCTCTCgggacagtctctgaatgggtcgcttttg |
| 321 | CTCTCTCTCTCTCTCTCTCTCTCTCTCatcttctcaaggataggcacaatcatgtcaaatttggg |
| 322 | CTCTCTCTCTCTCTCTCTCTCTCTCTCtgaactaaagctggacacggactgggtttc |
| 323 | CTCTCTCTCTCTCTCTCTCTCTCTCTCtataaatacagctgtttgggcaggaatcgggtg |
| 324 | CTCTCTCTCTCTCTCTCTCTCTCTCTCccctcataggcataagtctgaagagagtcataag |
| 325 | CTCTCTCTCTCTCTCTCTCTCTCTCTCgaaaaggcatcctctgtatgtttccgtggc |
| 326 | CTCTCTCTCTCTCTCTCTCTCTCTCTCcactgctttctccacggggatcttaattatc |
| 327 | CTCTCTCTCTCTCTCTCTCTCTCTCTCgtgggggagttcaaggagtctgatgattg |
| 328 | CTCTCTCTCTCTCTCTCTCTCTCTCTCagagcccttataaataaaatcccccagttagtgtttgc |
| 329 | CTCTCTCTCTCTCTCTCTCTCTCTCTCcagaaatactaggaaatgcaaagtcttgaagctccaaaac |
| 330 | CTCTCTCTCTCTCTCTCTCTCTCTCTCacccaaagacatgtgagcaactgctaatgaaaagc |
| 331 | CTCTCTCTCTCTCTCTCTCTCTCTCTCccaggtctcagcgtctctgcgg |
| 332 | CTCTCTCTCTCTCTCTCTCTCTCTCTCaatcgcagccttccagccctcgaaatc |
| 333 | CTCTCTCTCTCTCTCTCTCTCTCTCTCaccccagagccctagctcatcc |
| 334 | CTCTCTCTCTCTCTCTCTCTCTCTCTCaaggcactgttctctttgaagtagggtgagtc |
| 335 | CTCTCTCTCTCTCTCTCTCTCTCTCTCactttattacatatgcaaccttgccatgcctgcc |
| 336 | CTCTCTCTCTCTCTCTCTCTCTCTCTCgactatggaaccttgggttcccacgg |
| 337 | CTCTCTCTCTCTCTCTCTCTCTCTCTCgtccacacattatctcagcggcataaaacgtg |
| 338 | CTCTCTCTCTCTCTCTCTCTCTCTCTCagtgacccagaggcccatccgg |
| 339 | CTCTCTCTCTCTCTCTCTCTCTCTCTCcaaccttcttcaagttcacatctagtagttttctctgc |
| 340 | CTCTCTCTCTCTCTCTCTCTCTCTCTCtcactgctctgagggagaaagacgacc |
| 341 | CTCTCTCTCTCTCTCTCTCTCTCTCTCggagcaaaggagagtgcaaagcatgtactg |
| 342 | CTCTCTCTCTCTCTCTCTCTCTCTCTCgcctccaggtcactcagcttcttcatg |
| 343 | CTCTCTCTCTCTCTCTCTCTCTCTCTCaattgcatgaagcagggcatgaacatctgttg |
| 344 | CTCTCTCTCTCTCTCTCTCTCTCTCTCgttctccaccccacatgtataccaataccatg |
| 345 | CTCTCTCTCTCTCTCTCTCTCTCTCTCtcccaaataggtgttttacagataagggtcaatacgaag |
| 346 | CTCTCTCTCTCTCTCTCTCTCTCTCTCttcaggtcttaaggtaaaatagttccacagtctacagg |

TABLE 5-continued

| SEQ ID NO: | Sequence |
|---|---|
| 347 | CTCTCTCTCTCTCTCTCTCTCTCTCTCatgagcagcattgtaagttgtgatgcattcatttggattg |
| 348 | CTCTCTCTCTCTCTCTCTCTCTCTCTCtctgctaagccaagggctgccacaatg |
| 349 | CTCTCTCTCTCTCTCTCTCTCTCTCTCcctcccctacctcaaaatgctttagggag |
| 350 | CTCTCTCTCTCTCTCTCTCTCTCTCTCaggacaagcggtggccaatcaaccg |
| 351 | CTCTCTCTCTCTCTCTCTCTCTCTCTCgtccaggtggctcatggctccttag |
| 352 | CTCTCTCTCTCTCTCTCTCTCTCTCTCccactgggttttatccatgtccaattcgc |
| 353 | CTCTCTCTCTCTCTCTCTCTCTCTCTCctccttggagctgaccgggcc |
| 354 | CTCTCTCTCTCTCTCTCTCTCTCTCTCcttttagaatagcacactccaaacaagtgatgggaac |
| 355 | CTCTCTCTCTCTCTCTCTCTCTCTCTCtctgcaaacagattcctcttcaacagattatatgcaagag |
| 356 | CTCTCTCTCTCTCTCTCTCTCTCTCTCtttctctcaaatacactctggcataccttatcttctcc |
| 357 | CTCTCTCTCTCTCTCTCTCTCTCTCTCccagttttccatagtttctagtaacgcccaacag |
| 358 | CTCTCTCTCTCTCTCTCTCTCTCTCTCtccttggacagaggtgcctgagcac |
| 359 | CTCTCTCTCTCTCTCTCTCTCTCTCTCcatccacctccactagagcctcaaagg |
| 360 | CTCTCTCTCTCTCTCTCTCTCTCTCTCtttctgttatacaagtatattacacagcttggggtagtaacag |
| 361 | CTCTCTCTCTCTCTCTCTCTCTCTCTCggcaacagtgagatccagaagcagatcattg |
| 362 | CTCTCTCTCTCTCTCTCTCTCTCTCTCacacatggtgccggaatgatatgtagtcgtc |
| 363 | CTCTCTCTCTCTCTCTCTCTCTCTCTCggatctcattcctaatggtccgccgaag |
| 364 | CTCTCTCTCTCTCTCTCTCTCTCTCTCgctgcaaactggtttaagatagcttgccgattttg |
| 365 | CTCTCTCTCTCTCTCTCTCTCTCTCTCggcttccaggacctctgagttgatacc |
| 366 | CTCTCTCTCTCTCTCTCTCTCTCTCTCtactgcagacactttcctgtgagccagaag |
| 367 | CTCTCTCTCTCTCTCTCTCTCTCTCTCtttatttccatgttcaacctgcggagaaaaccgg |
| 368 | CTCTCTCTCTCTCTCTCTCTCTCTCTCttttcaggggattaacttgggaatggtgcagtg |
| 369 | CTCTCTCTCTCTCTCTCTCTCTCTCTCctgaatataccatggaaaactggggatttatagacagg |
| 370 | CTCTCTCTCTCTCTCTCTCTCTCTCTCggaaaataagtacagtctattgatccgtgatgcatgc |
| 371 | CTCTCTCTCTCTCTCTCTCTCTCTCTCTCtgattctacaggtttaaagttttgactgaaaatacacagaactca |
| 372 | CTCTCTCTCTCTCTCTCTCTCTCTCTCccggtccaaagccccctccg |
| 373 | CTCTCTCTCTCTCTCTCTCTCTCTCTCctgataccacagaattaccttgtcacaatacaggg |
| 374 | CTCTCTCTCTCTCTCTCTCTCTCTCTCgaccattctcggctgaaaattgacatggtcaaag |
| 375 | CTCTCTCTCTCTCTCTCTCTCTCTCTCctcccattctgctctgccacgtttacc |
| 376 | CTCTCTCTCTCTCTCTCTCTCTCTCTCgactttaagtcacataatcgatcccaagcactctc |
| 377 | CTCTCTCTCTCTCTCTCTCTCTCTCTCtatcagaatcaaagtagaggcaataacaagccaaggtg |
| 378 | CTCTCTCTCTCTCTCTCTCTCTCTCTCggatggagttttaaaagcccacatgtaccaataatgg |
| 379 | CTCTCTCTCTCTCTCTCTCTCTCTCTCTCatttctagactttcatgtttgtcttttgtcttctgctggaaac |
| 380 | CTCTCTCTCTCTCTCTCTCTCTCTCTCcctaggaacctaattgtgaacaaaactcacagcttc |
| 381 | CTCTCTCTCTCTCTCTCTCTCTCTCTCatgacaagtgtactgatgtttgatggtaacatccagatg |
| 382 | CTCTCTCTCTCTCTCTCTCTCTCTCTCTCaaaatggtaaaagatttcctcacgcaagaggcatttttgc |
| 383 | CTCTCTCTCTCTCTCTCTCTCTCTCTCtgaatttagaatcaatgaaggaggagtcgatccactttc |

TABLE 5-continued

| SEQ ID NO: | Sequence |
|---|---|
| 384 | CTCTCTCTCTCTCTCTCTCTCTCTCTCTCatcagaaggaatttaaacttgatttctccgcaacccc |
| 385 | Cy5-GAGAGAGAGAGAGAGAGAGAGAGAGAGAG |

These nucleic acid samples were mixed according to Table 6 to prepare 8 samples for identification of probe positions.

TABLE 6

| SEQ ID NO: | Sample 1 | Sample 2 | Sample 3 | Sample 4 | Sample 5 | Sample 6 | Sample 7 | Sample 8 |
|---|---|---|---|---|---|---|---|---|
| 193 | 0 | 0 | 0 | 0 | 0 | 0 | 0 | 1 |
| 194 | 0 | 0 | 0 | 0 | 0 | 0 | 1 | 0 |
| 195 | 0 | 0 | 0 | 0 | 0 | 0 | 1 | 1 |
| 196 | 0 | 0 | 0 | 0 | 0 | 1 | 0 | 0 |
| 197 | 0 | 0 | 0 | 0 | 0 | 1 | 0 | 1 |
| 198 | 0 | 0 | 0 | 0 | 0 | 1 | 1 | 0 |
| 199 | 0 | 0 | 0 | 0 | 0 | 1 | 1 | 1 |
| 200 | 0 | 0 | 0 | 0 | 1 | 0 | 0 | 0 |
| 201 | 0 | 0 | 0 | 0 | 1 | 0 | 0 | 1 |
| 202 | 0 | 0 | 0 | 0 | 1 | 0 | 1 | 0 |
| 203 | 0 | 0 | 0 | 0 | 1 | 0 | 1 | 1 |
| 204 | 0 | 0 | 0 | 0 | 1 | 1 | 0 | 0 |
| 205 | 0 | 0 | 0 | 0 | 1 | 1 | 0 | 1 |
| 206 | 0 | 0 | 0 | 0 | 1 | 1 | 1 | 0 |
| 207 | 0 | 0 | 0 | 0 | 1 | 1 | 1 | 1 |
| 208 | 0 | 0 | 0 | 1 | 0 | 0 | 0 | 0 |
| 209 | 0 | 0 | 0 | 1 | 0 | 0 | 0 | 1 |
| 210 | 0 | 0 | 0 | 1 | 0 | 0 | 1 | 0 |
| 211 | 0 | 0 | 0 | 1 | 0 | 0 | 1 | 1 |
| 212 | 0 | 0 | 0 | 1 | 0 | 1 | 0 | 0 |
| 213 | 0 | 0 | 0 | 1 | 0 | 1 | 0 | 1 |
| 214 | 0 | 0 | 0 | 1 | 0 | 1 | 1 | 0 |
| 215 | 0 | 0 | 0 | 1 | 0 | 1 | 1 | 1 |
| 216 | 0 | 0 | 0 | 1 | 1 | 0 | 0 | 0 |
| 217 | 0 | 0 | 0 | 1 | 1 | 0 | 0 | 1 |
| 218 | 0 | 0 | 0 | 1 | 1 | 0 | 1 | 0 |
| 219 | 0 | 0 | 0 | 1 | 1 | 0 | 1 | 1 |
| 220 | 0 | 0 | 0 | 1 | 1 | 1 | 0 | 0 |
| 221 | 0 | 0 | 0 | 1 | 1 | 1 | 0 | 1 |
| 222 | 0 | 0 | 0 | 1 | 1 | 1 | 1 | 0 |
| 223 | 0 | 0 | 0 | 1 | 1 | 1 | 1 | 1 |
| 224 | 0 | 0 | 1 | 0 | 0 | 0 | 0 | 0 |
| 225 | 0 | 0 | 1 | 0 | 0 | 0 | 0 | 1 |
| 226 | 0 | 0 | 1 | 0 | 0 | 0 | 1 | 0 |
| 227 | 0 | 0 | 1 | 0 | 0 | 0 | 1 | 1 |
| 228 | 0 | 0 | 1 | 0 | 0 | 1 | 0 | 0 |
| 229 | 0 | 0 | 1 | 0 | 0 | 1 | 0 | 1 |
| 230 | 0 | 0 | 1 | 0 | 0 | 1 | 1 | 0 |
| 231 | 0 | 0 | 1 | 0 | 0 | 1 | 1 | 1 |
| 232 | 0 | 0 | 1 | 0 | 1 | 0 | 0 | 0 |
| 233 | 0 | 0 | 1 | 0 | 1 | 0 | 0 | 1 |
| 234 | 0 | 0 | 1 | 0 | 1 | 0 | 1 | 0 |
| 235 | 0 | 0 | 1 | 0 | 1 | 0 | 1 | 1 |
| 236 | 0 | 0 | 1 | 0 | 1 | 1 | 0 | 0 |
| 237 | 0 | 0 | 1 | 0 | 1 | 1 | 0 | 1 |
| 238 | 0 | 0 | 1 | 0 | 1 | 1 | 1 | 0 |
| 239 | 0 | 0 | 1 | 0 | 1 | 1 | 1 | 1 |
| 240 | 0 | 0 | 1 | 1 | 0 | 0 | 0 | 0 |
| 241 | 0 | 0 | 1 | 1 | 0 | 0 | 0 | 1 |
| 242 | 0 | 0 | 1 | 1 | 0 | 0 | 1 | 0 |
| 243 | 0 | 0 | 1 | 1 | 0 | 0 | 1 | 1 |
| 244 | 0 | 0 | 1 | 1 | 0 | 1 | 0 | 0 |
| 245 | 0 | 0 | 1 | 1 | 0 | 1 | 0 | 1 |
| 246 | 0 | 0 | 1 | 1 | 0 | 1 | 1 | 0 |
| 247 | 0 | 0 | 1 | 1 | 0 | 1 | 1 | 1 |
| 248 | 0 | 0 | 1 | 1 | 1 | 0 | 0 | 0 |
| 249 | 0 | 0 | 1 | 1 | 1 | 0 | 0 | 1 |
| 250 | 0 | 0 | 1 | 1 | 1 | 0 | 1 | 0 |
| 251 | 0 | 0 | 1 | 1 | 1 | 0 | 1 | 1 |
| 252 | 0 | 0 | 1 | 1 | 1 | 1 | 0 | 0 |
| 253 | 0 | 0 | 1 | 1 | 1 | 1 | 0 | 1 |

TABLE 6-continued

| SEQ ID NO: | Sample 1 | Sample 2 | Sample 3 | Sample 4 | Sample 5 | Sample 6 | Sample 7 | Sample 8 |
|---|---|---|---|---|---|---|---|---|
| 254 | 0 | 0 | 1 | 1 | 1 | 1 | 1 | 0 |
| 255 | 0 | 0 | 1 | 1 | 1 | 1 | 1 | 1 |
| 256 | 0 | 1 | 0 | 0 | 0 | 0 | 0 | 0 |
| 257 | 0 | 1 | 0 | 0 | 0 | 0 | 0 | 1 |
| 258 | 0 | 1 | 0 | 0 | 0 | 0 | 1 | 0 |
| 259 | 0 | 1 | 0 | 0 | 0 | 0 | 1 | 1 |
| 260 | 0 | 1 | 0 | 0 | 0 | 1 | 0 | 0 |
| 261 | 0 | 1 | 0 | 0 | 0 | 1 | 0 | 1 |
| 262 | 0 | 1 | 0 | 0 | 0 | 1 | 1 | 0 |
| 263 | 0 | 1 | 0 | 0 | 0 | 1 | 1 | 1 |
| 264 | 0 | 1 | 0 | 0 | 1 | 0 | 0 | 0 |
| 265 | 0 | 1 | 0 | 0 | 1 | 0 | 0 | 1 |
| 266 | 0 | 1 | 0 | 0 | 1 | 0 | 1 | 0 |
| 267 | 0 | 1 | 0 | 0 | 1 | 0 | 1 | 1 |
| 268 | 0 | 1 | 0 | 0 | 1 | 1 | 0 | 0 |
| 269 | 0 | 1 | 0 | 0 | 1 | 1 | 0 | 1 |
| 270 | 0 | 1 | 0 | 0 | 1 | 1 | 1 | 0 |
| 271 | 0 | 1 | 0 | 0 | 1 | 1 | 1 | 1 |
| 272 | 0 | 1 | 0 | 1 | 0 | 0 | 0 | 0 |
| 273 | 0 | 1 | 0 | 1 | 0 | 0 | 0 | 1 |
| 274 | 0 | 1 | 0 | 1 | 0 | 0 | 1 | 0 |
| 275 | 0 | 1 | 0 | 1 | 0 | 0 | 1 | 1 |
| 276 | 0 | 1 | 0 | 1 | 0 | 1 | 0 | 0 |
| 277 | 0 | 1 | 0 | 1 | 0 | 1 | 0 | 1 |
| 278 | 0 | 1 | 0 | 1 | 0 | 1 | 1 | 0 |
| 279 | 0 | 1 | 0 | 1 | 0 | 1 | 1 | 1 |
| 280 | 0 | 1 | 0 | 1 | 1 | 0 | 0 | 0 |
| 281 | 0 | 1 | 0 | 1 | 1 | 0 | 0 | 1 |
| 282 | 0 | 1 | 0 | 1 | 1 | 0 | 1 | 0 |
| 283 | 0 | 1 | 0 | 1 | 1 | 0 | 1 | 1 |
| 284 | 0 | 1 | 0 | 1 | 1 | 1 | 0 | 0 |
| 285 | 0 | 1 | 0 | 1 | 1 | 1 | 0 | 1 |
| 286 | 0 | 1 | 0 | 1 | 1 | 1 | 1 | 0 |
| 287 | 0 | 1 | 0 | 1 | 1 | 1 | 1 | 1 |
| 288 | 0 | 1 | 1 | 0 | 0 | 0 | 0 | 0 |
| 289 | 0 | 1 | 1 | 0 | 0 | 0 | 0 | 1 |
| 290 | 0 | 1 | 1 | 0 | 0 | 0 | 1 | 0 |
| 291 | 0 | 1 | 1 | 0 | 0 | 0 | 1 | 1 |
| 292 | 0 | 1 | 1 | 0 | 0 | 1 | 0 | 0 |
| 293 | 0 | 1 | 1 | 0 | 0 | 1 | 0 | 1 |
| 294 | 0 | 1 | 1 | 0 | 0 | 1 | 1 | 0 |
| 295 | 0 | 1 | 1 | 0 | 0 | 1 | 1 | 1 |
| 296 | 0 | 1 | 1 | 0 | 1 | 0 | 0 | 0 |
| 297 | 0 | 1 | 1 | 0 | 1 | 0 | 0 | 1 |
| 298 | 0 | 1 | 1 | 0 | 1 | 0 | 1 | 0 |
| 299 | 0 | 1 | 1 | 0 | 1 | 0 | 1 | 1 |
| 300 | 0 | 1 | 1 | 0 | 1 | 1 | 0 | 0 |
| 301 | 0 | 1 | 1 | 0 | 1 | 1 | 0 | 1 |
| 302 | 0 | 1 | 1 | 0 | 1 | 1 | 1 | 0 |
| 303 | 0 | 1 | 1 | 0 | 1 | 1 | 1 | 1 |
| 304 | 0 | 1 | 1 | 1 | 0 | 0 | 0 | 0 |
| 305 | 0 | 1 | 1 | 1 | 0 | 0 | 0 | 1 |
| 306 | 0 | 1 | 1 | 1 | 0 | 0 | 1 | 0 |
| 307 | 0 | 1 | 1 | 1 | 0 | 0 | 1 | 1 |
| 308 | 0 | 1 | 1 | 1 | 0 | 1 | 0 | 0 |
| 309 | 0 | 1 | 1 | 1 | 0 | 1 | 0 | 1 |
| 310 | 0 | 1 | 1 | 1 | 0 | 1 | 1 | 0 |
| 311 | 0 | 1 | 1 | 1 | 0 | 1 | 1 | 1 |
| 312 | 0 | 1 | 1 | 1 | 1 | 0 | 0 | 0 |
| 313 | 0 | 1 | 1 | 1 | 1 | 0 | 0 | 1 |
| 314 | 0 | 1 | 1 | 1 | 1 | 0 | 1 | 0 |
| 315 | 0 | 1 | 1 | 1 | 1 | 0 | 1 | 1 |
| 316 | 0 | 1 | 1 | 1 | 1 | 1 | 0 | 0 |
| 317 | 0 | 1 | 1 | 1 | 1 | 1 | 0 | 1 |
| 318 | 0 | 1 | 1 | 1 | 1 | 1 | 1 | 0 |
| 319 | 0 | 1 | 1 | 1 | 1 | 1 | 1 | 1 |
| 320 | 1 | 0 | 0 | 0 | 0 | 0 | 0 | 0 |
| 321 | 1 | 0 | 0 | 0 | 0 | 0 | 0 | 1 |
| 322 | 1 | 0 | 0 | 0 | 0 | 0 | 1 | 0 |
| 323 | 1 | 0 | 0 | 0 | 0 | 0 | 1 | 1 |
| 324 | 1 | 0 | 0 | 0 | 0 | 1 | 0 | 0 |
| 325 | 1 | 0 | 0 | 0 | 0 | 1 | 0 | 1 |
| 326 | 1 | 0 | 0 | 0 | 0 | 1 | 1 | 0 |
| 327 | 1 | 0 | 0 | 0 | 0 | 1 | 1 | 1 |
| 328 | 1 | 0 | 0 | 0 | 1 | 0 | 0 | 0 |
| 329 | 1 | 0 | 0 | 0 | 1 | 0 | 0 | 1 |
| 330 | 1 | 0 | 0 | 0 | 1 | 0 | 1 | 0 |

TABLE 6-continued

| SEQ ID NO: | Sample 1 | Sample 2 | Sample 3 | Sample 4 | Sample 5 | Sample 6 | Sample 7 | Sample 8 |
|---|---|---|---|---|---|---|---|---|
| 331 | 1 | 0 | 0 | 0 | 1 | 0 | 1 | 1 |
| 332 | 1 | 0 | 0 | 0 | 1 | 1 | 0 | 0 |
| 333 | 1 | 0 | 0 | 0 | 1 | 1 | 0 | 1 |
| 334 | 1 | 0 | 0 | 0 | 1 | 1 | 1 | 0 |
| 335 | 1 | 0 | 0 | 0 | 1 | 1 | 1 | 1 |
| 336 | 1 | 0 | 0 | 1 | 0 | 0 | 0 | 0 |
| 337 | 1 | 0 | 0 | 1 | 0 | 0 | 0 | 1 |
| 338 | 1 | 0 | 0 | 1 | 0 | 0 | 1 | 0 |
| 339 | 1 | 0 | 0 | 1 | 0 | 0 | 1 | 1 |
| 340 | 1 | 0 | 0 | 1 | 0 | 1 | 0 | 0 |
| 341 | 1 | 0 | 0 | 1 | 0 | 1 | 0 | 1 |
| 342 | 1 | 0 | 0 | 1 | 0 | 1 | 1 | 0 |
| 343 | 1 | 0 | 0 | 1 | 0 | 1 | 1 | 1 |
| 344 | 1 | 0 | 0 | 1 | 1 | 0 | 0 | 0 |
| 345 | 1 | 0 | 0 | 1 | 1 | 0 | 0 | 1 |
| 346 | 1 | 0 | 0 | 1 | 1 | 0 | 1 | 0 |
| 347 | 1 | 0 | 0 | 1 | 1 | 0 | 1 | 1 |
| 348 | 1 | 0 | 0 | 1 | 1 | 1 | 0 | 0 |
| 349 | 1 | 0 | 0 | 1 | 1 | 1 | 0 | 1 |
| 350 | 1 | 0 | 0 | 1 | 1 | 1 | 1 | 0 |
| 351 | 1 | 0 | 0 | 1 | 1 | 1 | 1 | 1 |
| 352 | 1 | 0 | 1 | 0 | 0 | 0 | 0 | 0 |
| 353 | 1 | 0 | 1 | 0 | 0 | 0 | 0 | 1 |
| 354 | 1 | 0 | 1 | 0 | 0 | 0 | 1 | 0 |
| 355 | 1 | 0 | 1 | 0 | 0 | 0 | 1 | 1 |
| 356 | 1 | 0 | 1 | 0 | 0 | 1 | 0 | 0 |
| 357 | 1 | 0 | 1 | 0 | 0 | 1 | 0 | 1 |
| 358 | 1 | 0 | 1 | 0 | 0 | 1 | 1 | 0 |
| 359 | 1 | 0 | 1 | 0 | 0 | 1 | 1 | 1 |
| 360 | 1 | 0 | 1 | 0 | 1 | 0 | 0 | 0 |
| 361 | 1 | 0 | 1 | 0 | 1 | 0 | 0 | 1 |
| 362 | 1 | 0 | 1 | 0 | 1 | 0 | 1 | 0 |
| 363 | 1 | 0 | 1 | 0 | 1 | 0 | 1 | 1 |
| 364 | 1 | 0 | 1 | 0 | 1 | 1 | 0 | 0 |
| 365 | 1 | 0 | 1 | 0 | 1 | 1 | 0 | 1 |
| 366 | 1 | 0 | 1 | 0 | 1 | 1 | 1 | 0 |
| 367 | 1 | 0 | 1 | 0 | 1 | 1 | 1 | 1 |
| 368 | 1 | 0 | 1 | 1 | 0 | 0 | 0 | 0 |
| 369 | 1 | 0 | 1 | 1 | 0 | 0 | 0 | 1 |
| 370 | 1 | 0 | 1 | 1 | 0 | 0 | 1 | 0 |
| 371 | 1 | 0 | 1 | 1 | 0 | 0 | 1 | 1 |
| 372 | 1 | 0 | 1 | 1 | 0 | 1 | 0 | 0 |
| 373 | 1 | 0 | 1 | 1 | 0 | 1 | 0 | 1 |
| 374 | 1 | 0 | 1 | 1 | 0 | 1 | 1 | 0 |
| 375 | 1 | 0 | 1 | 1 | 0 | 1 | 1 | 1 |
| 376 | 1 | 0 | 1 | 1 | 1 | 0 | 0 | 0 |
| 377 | 1 | 0 | 1 | 1 | 1 | 0 | 0 | 1 |
| 378 | 1 | 0 | 1 | 1 | 1 | 0 | 1 | 0 |
| 379 | 1 | 0 | 1 | 1 | 1 | 0 | 1 | 1 |
| 380 | 1 | 0 | 1 | 1 | 1 | 1 | 0 | 0 |
| 381 | 1 | 0 | 1 | 1 | 1 | 1 | 0 | 1 |
| 382 | 1 | 0 | 1 | 1 | 1 | 1 | 1 | 0 |
| 383 | 1 | 0 | 1 | 1 | 1 | 1 | 1 | 1 |
| 384 | 1 | 1 | 0 | 0 | 0 | 0 | 0 | 0 |

In Table 6, "1" means that a complementary nucleic acid having a nucleotide sequence represented by SEQ ID NO: described in the leftmost column in Table 6 is included in a sample. "0" means that a complementary nucleic acid having a nucleotide sequence represented by SEQ ID NO: described in the leftmost column in Table 6 is not included in a sample. Samples 1-8 were prepared by mixing each model analyte indicated by SEQ ID NO: shown as "1" in an amount of 500 pmol/5 µl, and adding pure water so that the final liquid volume was adjusted to 500 µl. That is, Samples 1-8 were prepared so that the concentration of each of the model analytes contained was adjusted to 1 pmol/µl. Further, patterns of the presence/absence of input of all the analytes represented by SEQ ID NOs: 193-384 in Samples 1-8 were different from each other.

0.2 µl (20 pmol) of Cy5-labeled analyte represented by SEQ ID NO: 385 was added to 0.2 µl of each of 8 samples prepared according to the above table (0.2 pmol each), and hybridization was performed under the following conditions. One hybridization reaction was performed for each nucleic acid array, i.e., a hybridization was performed 8 times.

| | |
|---|---|
| Labeled oligonucleotide (Combination of those selected from SEQ ID NOs: 193-384) | 0.2 pmol each |
| Cy5-labeled oligonucleotide (SEQ ID NO: 385) | 20 pmol |
| 2 × SSC (300 mM of sodium chloride, 30 mM of sodium citrate, pH 7.0) | |
| 0.2% SDS (sodium dodecyl sulfate) | |

Hybridization Reaction, Washing and Detection Operation

The nucleic acid samples prepared above were contacted with the nucleic acid arrays prepared above, and hybridization was conducted in a temperature-controlled bath at 65° C. for 1 hour.

After hybridization, washing was conducted using a mixed solution of 2×SSC and 0.2% SDS and 2×SSC, and subsequently detection was conducted. In the detection operation: a cooled CCD camera-type automatic detection apparatus for nucleic acid array was used; arrays were immersed in 2×SSC; a cover glass was applied thereto; and subsequently the fluorescence signal strength of labeled nucleic acid sample molecules was measured.

Results

Images of detection of Samples 1-8 are shown in FIG. 3. In the case where the types and immobilization positions of the nucleic acid probes are confirmed based on the results in FIG. 3, for example, ON/OFF of signal from the position identified by column (R)=1 and row (C)=2 (SEQ ID NO: 96) in FIG. 2 is expressed as "OFF, ON, ON, OFF, OFF, OFF, OFF, OFF" in the order of Samples 1-8. In Table 6, only SEQ ID NO: 288, which is an analyte corresponding to SEQ ID NO: 96, has this combination of ON and OFF. Therefore, it was confirmed that on the position identified by R=1 and C=2, a nucleic acid probe, which has a sequence complementary to SEQ ID NO: 288, i.e., a nucleic acid probe set forth in SEQ ID NO: 96, is surely immobilized. Similarly, ONs/OFFs of signals from the positions of respective nucleic acid probes obtained this time were compared and the results are described in Table 7. In Table 7, "Presence or absence of analyte input (predetermined)" is expressed by numerical values allocated to probes set forth in respective SEQ ID NOs. "0" means that a complementary nucleic acid with respect to a corresponding probe is not included, and "1" means that a complementary nucleic acid with respect to a corresponding probe is included. Regarding ON/OFF of signal, when the ratio of S/N is 5 or higher, it is defined as ON, and when the ratio is less than 5, it is defined as OFF. "ON" and "OFF" in Table 7 can be replaced by "1" and "0" in binary notation, respectively.

TABLE 7

| | Presence or absence of analyte input (predetermined) Sample No. | | | | | | | | Position on array | | ON/OFF of signal (Result) Nucleic acid array (chip) | | | | | | | | |
|---|---|---|---|---|---|---|---|---|---|---|---|---|---|---|---|---|---|---|---|
| *a | 1 | 2 | 3 | 4 | 5 | 6 | 7 | 8 | *b | *c | 1 | 2 | 3 | 4 | 5 | 6 | 7 | 8 | *d |
| 193 | 0 | 0 | 0 | 0 | 0 | 0 | 0 | 1 | 5 | 15 | OFF | OFF | OFF | OFF | OFF | OFF | OFF | ON | 1 |
| 194 | 0 | 0 | 0 | 0 | 0 | 0 | 1 | 0 | 5 | 16 | OFF | OFF | OFF | OFF | OFF | OFF | ON | OFF | 2 |
| 195 | 0 | 0 | 0 | 0 | 0 | 0 | 1 | 1 | 5 | 17 | OFF | OFF | OFF | OFF | OFF | OFF | ON | ON | 3 |
| 196 | 0 | 0 | 0 | 0 | 0 | 1 | 0 | 0 | 5 | 18 | OFF | OFF | OFF | OFF | OFF | ON | OFF | OFF | 4 |
| 197 | 0 | 0 | 0 | 0 | 0 | 1 | 0 | 1 | 6 | 2 | OFF | OFF | OFF | OFF | OFF | ON | OFF | ON | 5 |
| 198 | 0 | 0 | 0 | 0 | 0 | 1 | 1 | 0 | 6 | 3 | OFF | OFF | OFF | OFF | OFF | ON | ON | OFF | 6 |
| 199 | 0 | 0 | 0 | 0 | 0 | 1 | 1 | 1 | 6 | 4 | OFF | OFF | OFF | OFF | OFF | ON | ON | ON | 7 |
| 200 | 0 | 0 | 0 | 0 | 1 | 0 | 0 | 0 | 6 | 5 | OFF | OFF | OFF | OFF | ON | OFF | OFF | OFF | 8 |
| 201 | 0 | 0 | 0 | 0 | 1 | 0 | 0 | 1 | 6 | 6 | OFF | OFF | OFF | OFF | ON | OFF | OFF | ON | 9 |
| 202 | 0 | 0 | 0 | 0 | 1 | 0 | 1 | 0 | 6 | 7 | OFF | OFF | OFF | OFF | ON | OFF | ON | OFF | 10 |
| 203 | 0 | 0 | 0 | 0 | 1 | 0 | 1 | 1 | 6 | 8 | OFF | OFF | OFF | OFF | ON | OFF | ON | ON | 11 |
| 204 | 0 | 0 | 0 | 0 | 1 | 1 | 0 | 0 | 6 | 9 | OFF | OFF | OFF | OFF | ON | ON | OFF | OFF | 12 |
| 205 | 0 | 0 | 0 | 0 | 1 | 1 | 0 | 1 | 6 | 10 | OFF | OFF | OFF | OFF | ON | ON | OFF | ON | 13 |
| 206 | 0 | 0 | 0 | 0 | 1 | 1 | 1 | 0 | 6 | 11 | OFF | OFF | OFF | OFF | ON | ON | ON | OFF | 14 |
| 207 | 0 | 0 | 0 | 0 | 1 | 1 | 1 | 1 | 6 | 12 | OFF | OFF | OFF | OFF | ON | ON | ON | ON | 15 |
| 208 | 0 | 0 | 0 | 1 | 0 | 0 | 0 | 0 | 6 | 13 | OFF | OFF | OFF | ON | OFF | OFF | OFF | OFF | 16 |
| 209 | 0 | 0 | 0 | 1 | 0 | 0 | 0 | 1 | 6 | 14 | OFF | OFF | OFF | ON | OFF | OFF | OFF | ON | 17 |
| 210 | 0 | 0 | 0 | 1 | 0 | 0 | 1 | 0 | 6 | 15 | OFF | OFF | OFF | ON | OFF | OFF | ON | OFF | 18 |
| 211 | 0 | 0 | 0 | 1 | 0 | 0 | 1 | 1 | 6 | 16 | OFF | OFF | OFF | ON | OFF | OFF | ON | ON | 19 |
| 212 | 0 | 0 | 0 | 1 | 0 | 1 | 0 | 0 | 6 | 17 | OFF | OFF | OFF | ON | OFF | ON | OFF | OFF | 20 |
| 213 | 0 | 0 | 0 | 1 | 0 | 1 | 0 | 1 | 6 | 18 | OFF | OFF | OFF | ON | OFF | ON | OFF | ON | 21 |
| 214 | 0 | 0 | 0 | 1 | 0 | 1 | 1 | 0 | 7 | 2 | OFF | OFF | OFF | ON | OFF | ON | ON | OFF | 22 |
| 215 | 0 | 0 | 0 | 1 | 0 | 1 | 1 | 1 | 7 | 3 | OFF | OFF | OFF | ON | OFF | ON | ON | ON | 23 |
| 216 | 0 | 0 | 0 | 1 | 1 | 0 | 0 | 0 | 7 | 4 | OFF | OFF | OFF | ON | ON | OFF | OFF | OFF | 24 |
| 217 | 0 | 0 | 0 | 1 | 1 | 0 | 0 | 1 | 7 | 5 | OFF | OFF | OFF | ON | ON | OFF | OFF | ON | 25 |
| 218 | 0 | 0 | 0 | 1 | 1 | 0 | 1 | 0 | 7 | 6 | OFF | OFF | OFF | ON | ON | OFF | ON | OFF | 26 |
| 219 | 0 | 0 | 0 | 1 | 1 | 0 | 1 | 1 | 7 | 7 | OFF | OFF | OFF | ON | ON | OFF | ON | ON | 27 |
| 220 | 0 | 0 | 0 | 1 | 1 | 1 | 0 | 0 | 7 | 8 | OFF | OFF | OFF | ON | ON | ON | OFF | OFF | 28 |
| 221 | 0 | 0 | 0 | 1 | 1 | 1 | 0 | 1 | 7 | 9 | OFF | OFF | OFF | ON | ON | ON | OFF | ON | 29 |
| 222 | 0 | 0 | 0 | 1 | 1 | 1 | 1 | 0 | 7 | 10 | OFF | OFF | OFF | ON | ON | ON | ON | OFF | 30 |
| 223 | 0 | 0 | 0 | 1 | 1 | 1 | 1 | 1 | 7 | 11 | OFF | OFF | OFF | ON | ON | ON | ON | ON | 31 |
| 224 | 0 | 0 | 1 | 0 | 0 | 0 | 0 | 0 | 7 | 12 | OFF | OFF | ON | OFF | OFF | OFF | OFF | OFF | 32 |
| 225 | 0 | 0 | 1 | 0 | 0 | 0 | 0 | 1 | 7 | 13 | OFF | OFF | ON | OFF | OFF | OFF | OFF | ON | 33 |
| 226 | 0 | 0 | 1 | 0 | 0 | 0 | 1 | 0 | 7 | 14 | OFF | OFF | ON | OFF | OFF | OFF | ON | OFF | 34 |
| 227 | 0 | 0 | 1 | 0 | 0 | 0 | 1 | 1 | 7 | 15 | OFF | OFF | ON | OFF | OFF | OFF | ON | ON | 35 |
| 228 | 0 | 0 | 1 | 0 | 0 | 1 | 0 | 0 | 7 | 16 | OFF | OFF | ON | OFF | OFF | ON | OFF | OFF | 36 |
| 229 | 0 | 0 | 1 | 0 | 0 | 1 | 0 | 1 | 7 | 17 | OFF | OFF | ON | OFF | OFF | ON | OFF | ON | 37 |
| 230 | 0 | 0 | 1 | 0 | 0 | 1 | 1 | 0 | 7 | 18 | OFF | OFF | ON | OFF | OFF | ON | ON | OFF | 38 |
| 231 | 0 | 0 | 1 | 0 | 0 | 1 | 1 | 1 | 8 | 2 | OFF | OFF | ON | OFF | OFF | ON | ON | ON | 39 |
| 232 | 0 | 0 | 1 | 0 | 1 | 0 | 0 | 0 | 8 | 3 | OFF | OFF | ON | OFF | ON | OFF | OFF | OFF | 40 |
| 233 | 0 | 0 | 1 | 0 | 1 | 0 | 0 | 1 | 8 | 4 | OFF | OFF | ON | OFF | ON | OFF | OFF | ON | 41 |
| 234 | 0 | 0 | 1 | 0 | 1 | 0 | 1 | 0 | 8 | 5 | OFF | OFF | ON | OFF | ON | OFF | ON | OFF | 42 |
| 235 | 0 | 0 | 1 | 0 | 1 | 0 | 1 | 1 | 8 | 6 | OFF | OFF | ON | OFF | ON | OFF | ON | ON | 43 |
| 236 | 0 | 0 | 1 | 0 | 1 | 1 | 0 | 0 | 8 | 7 | OFF | OFF | ON | OFF | ON | ON | OFF | OFF | 44 |
| 237 | 0 | 0 | 1 | 0 | 1 | 1 | 0 | 1 | 8 | 8 | OFF | OFF | ON | OFF | ON | ON | OFF | ON | 45 |
| 238 | 0 | 0 | 1 | 0 | 1 | 1 | 1 | 0 | 8 | 12 | OFF | OFF | ON | OFF | ON | ON | ON | OFF | 46 |
| 239 | 0 | 0 | 1 | 0 | 1 | 1 | 1 | 1 | 8 | 13 | OFF | OFF | ON | OFF | ON | ON | ON | ON | 47 |
| 240 | 0 | 0 | 1 | 1 | 0 | 0 | 0 | 0 | 8 | 14 | OFF | OFF | ON | ON | OFF | OFF | OFF | OFF | 48 |
| 241 | 0 | 0 | 1 | 1 | 0 | 0 | 0 | 1 | 8 | 15 | OFF | OFF | ON | ON | OFF | OFF | OFF | ON | 49 |
| 242 | 0 | 0 | 1 | 1 | 0 | 0 | 1 | 0 | 8 | 16 | OFF | OFF | ON | ON | OFF | OFF | ON | OFF | 50 |
| 243 | 0 | 0 | 1 | 1 | 0 | 0 | 1 | 1 | 8 | 17 | OFF | OFF | ON | ON | OFF | OFF | ON | ON | 51 |
| 244 | 0 | 0 | 1 | 1 | 0 | 1 | 0 | 0 | 8 | 18 | OFF | OFF | ON | ON | OFF | ON | OFF | OFF | 52 |
| 245 | 0 | 0 | 1 | 1 | 0 | 1 | 0 | 1 | 9 | 2 | OFF | OFF | ON | ON | OFF | ON | OFF | ON | 53 |

TABLE 7-continued

| | Presence or absence of analyte input (predetermined) Sample No. | | | | | | | | Position on array | | ON/OFF of signal (Result) Nucleic acid array (chip) | | | | | | | | |
|---|---|---|---|---|---|---|---|---|---|---|---|---|---|---|---|---|---|---|---|
| *a | 1 | 2 | 3 | 4 | 5 | 6 | 7 | 8 | *b | *c | 1 | 2 | 3 | 4 | 5 | 6 | 7 | 8 | *d |
| 246 | 0 | 0 | 1 | 1 | 0 | 1 | 1 | 0 | 9 | 3 | OFF | OFF | ON | ON | OFF | ON | ON | OFF | 54 |
| 247 | 0 | 0 | 1 | 1 | 0 | 1 | 1 | 1 | 9 | 4 | OFF | OFF | ON | ON | OFF | ON | ON | ON | 55 |
| 248 | 0 | 0 | 1 | 1 | 1 | 0 | 0 | 0 | 9 | 5 | OFF | OFF | ON | ON | ON | OFF | OFF | OFF | 56 |
| 249 | 0 | 0 | 1 | 1 | 1 | 0 | 0 | 1 | 9 | 6 | OFF | OFF | ON | ON | ON | OFF | OFF | ON | 57 |
| 250 | 0 | 0 | 1 | 1 | 1 | 0 | 1 | 0 | 9 | 7 | OFF | OFF | ON | ON | ON | OFF | ON | OFF | 58 |
| 251 | 0 | 0 | 1 | 1 | 1 | 0 | 1 | 1 | 9 | 8 | OFF | OFF | ON | ON | ON | OFF | ON | ON | 59 |
| 252 | 0 | 0 | 1 | 1 | 1 | 1 | 0 | 0 | 9 | 9 | OFF | OFF | ON | ON | ON | ON | OFF | OFF | 60 |
| 253 | 0 | 0 | 1 | 1 | 1 | 1 | 0 | 1 | 9 | 10 | OFF | OFF | ON | ON | ON | ON | OFF | ON | 61 |
| 254 | 0 | 0 | 1 | 1 | 1 | 1 | 1 | 0 | 9 | 11 | OFF | OFF | ON | ON | ON | ON | ON | OFF | 62 |
| 255 | 0 | 0 | 1 | 1 | 1 | 1 | 1 | 1 | 9 | 12 | OFF | OFF | ON | ON | ON | ON | ON | ON | 63 |
| 256 | 0 | 1 | 0 | 0 | 0 | 0 | 0 | 0 | 9 | 13 | OFF | ON | OFF | OFF | OFF | OFF | OFF | OFF | 64 |
| 257 | 0 | 1 | 0 | 0 | 0 | 0 | 0 | 1 | 9 | 14 | OFF | ON | OFF | OFF | OFF | OFF | OFF | ON | 65 |
| 258 | 0 | 1 | 0 | 0 | 0 | 0 | 1 | 0 | 9 | 15 | OFF | ON | OFF | OFF | OFF | OFF | ON | OFF | 66 |
| 259 | 0 | 1 | 0 | 0 | 0 | 0 | 1 | 1 | 9 | 16 | OFF | ON | OFF | OFF | OFF | OFF | ON | ON | 67 |
| 260 | 0 | 1 | 0 | 0 | 0 | 1 | 0 | 0 | 9 | 17 | OFF | ON | OFF | OFF | OFF | ON | OFF | OFF | 68 |
| 261 | 0 | 1 | 0 | 0 | 0 | 1 | 0 | 1 | 9 | 18 | OFF | ON | OFF | OFF | OFF | ON | OFF | ON | 69 |
| 262 | 0 | 1 | 0 | 0 | 0 | 1 | 1 | 0 | 4 | 3 | OFF | ON | OFF | OFF | OFF | ON | ON | OFF | 70 |
| 263 | 0 | 1 | 0 | 0 | 0 | 1 | 1 | 1 | 4 | 4 | OFF | ON | OFF | OFF | OFF | ON | ON | ON | 71 |
| 264 | 0 | 1 | 0 | 0 | 1 | 0 | 0 | 0 | 4 | 5 | OFF | ON | OFF | OFF | ON | OFF | OFF | OFF | 72 |
| 265 | 0 | 1 | 0 | 0 | 1 | 0 | 0 | 1 | 4 | 6 | OFF | ON | OFF | OFF | ON | OFF | OFF | ON | 73 |
| 266 | 0 | 1 | 0 | 0 | 1 | 0 | 1 | 0 | 4 | 7 | OFF | ON | OFF | OFF | ON | OFF | ON | OFF | 74 |
| 267 | 0 | 1 | 0 | 0 | 1 | 0 | 1 | 1 | 4 | 8 | OFF | ON | OFF | OFF | ON | OFF | ON | ON | 75 |
| 268 | 0 | 1 | 0 | 0 | 1 | 1 | 0 | 0 | 4 | 9 | OFF | ON | OFF | OFF | ON | ON | OFF | OFF | 76 |
| 269 | 0 | 1 | 0 | 0 | 1 | 1 | 0 | 1 | 4 | 10 | OFF | ON | OFF | OFF | ON | ON | OFF | ON | 77 |
| 270 | 0 | 1 | 0 | 0 | 1 | 1 | 1 | 0 | 4 | 11 | OFF | ON | OFF | OFF | ON | ON | ON | OFF | 78 |
| 271 | 0 | 1 | 0 | 0 | 1 | 1 | 1 | 1 | 4 | 12 | OFF | ON | OFF | OFF | ON | ON | ON | ON | 79 |
| 272 | 0 | 1 | 0 | 1 | 0 | 0 | 0 | 0 | 4 | 13 | OFF | ON | OFF | ON | OFF | OFF | OFF | OFF | 80 |
| 273 | 0 | 1 | 0 | 1 | 0 | 0 | 0 | 1 | 4 | 14 | OFF | ON | OFF | ON | OFF | OFF | OFF | ON | 81 |
| 274 | 0 | 1 | 0 | 1 | 0 | 0 | 1 | 0 | 4 | 15 | OFF | ON | OFF | ON | OFF | OFF | ON | OFF | 82 |
| 275 | 0 | 1 | 0 | 1 | 0 | 0 | 1 | 1 | 4 | 16 | OFF | ON | OFF | ON | OFF | OFF | ON | ON | 83 |
| 276 | 0 | 1 | 0 | 1 | 0 | 1 | 0 | 0 | 4 | 17 | OFF | ON | OFF | ON | OFF | ON | OFF | OFF | 84 |
| 277 | 0 | 1 | 0 | 1 | 0 | 1 | 0 | 1 | 4 | 18 | OFF | ON | OFF | ON | OFF | ON | OFF | ON | 85 |
| 278 | 0 | 1 | 0 | 1 | 0 | 1 | 1 | 0 | 5 | 2 | OFF | ON | OFF | ON | OFF | ON | ON | OFF | 86 |
| 279 | 0 | 1 | 0 | 1 | 0 | 1 | 1 | 1 | 5 | 3 | OFF | ON | OFF | ON | OFF | ON | ON | ON | 87 |
| 280 | 0 | 1 | 0 | 1 | 1 | 0 | 0 | 0 | 5 | 4 | OFF | ON | OFF | ON | ON | OFF | OFF | OFF | 88 |
| 281 | 0 | 1 | 0 | 1 | 1 | 0 | 0 | 1 | 5 | 5 | OFF | ON | OFF | ON | ON | OFF | OFF | ON | 89 |
| 282 | 0 | 1 | 0 | 1 | 1 | 0 | 1 | 0 | 5 | 6 | OFF | ON | OFF | ON | ON | OFF | ON | OFF | 90 |
| 283 | 0 | 1 | 0 | 1 | 1 | 0 | 1 | 1 | 5 | 7 | OFF | ON | OFF | ON | ON | OFF | ON | ON | 91 |
| 284 | 0 | 1 | 0 | 1 | 1 | 1 | 0 | 0 | 5 | 8 | OFF | ON | OFF | ON | ON | ON | OFF | OFF | 92 |
| 285 | 0 | 1 | 0 | 1 | 1 | 1 | 0 | 1 | 5 | 12 | OFF | ON | OFF | ON | ON | ON | OFF | ON | 93 |
| 286 | 0 | 1 | 0 | 1 | 1 | 1 | 1 | 0 | 5 | 13 | OFF | ON | OFF | ON | ON | ON | ON | OFF | 94 |
| 287 | 0 | 1 | 0 | 1 | 1 | 1 | 1 | 1 | 5 | 14 | OFF | ON | OFF | ON | ON | ON | ON | ON | 95 |
| 288 | 0 | 1 | 1 | 0 | 0 | 0 | 0 | 0 | 1 | 2 | OFF | ON | ON | OFF | OFF | OFF | OFF | OFF | 96 |
| 289 | 0 | 1 | 1 | 0 | 0 | 0 | 0 | 1 | 1 | 3 | OFF | ON | ON | OFF | OFF | OFF | OFF | ON | 97 |
| 290 | 0 | 1 | 1 | 0 | 0 | 0 | 1 | 0 | 1 | 4 | OFF | ON | ON | OFF | OFF | OFF | ON | OFF | 98 |
| 291 | 0 | 1 | 1 | 0 | 0 | 0 | 1 | 1 | 1 | 5 | OFF | ON | ON | OFF | OFF | OFF | ON | ON | 99 |
| 292 | 0 | 1 | 1 | 0 | 0 | 1 | 0 | 0 | 1 | 6 | OFF | ON | ON | OFF | OFF | ON | OFF | OFF | 100 |
| 293 | 0 | 1 | 1 | 0 | 0 | 1 | 0 | 1 | 1 | 7 | OFF | ON | ON | OFF | OFF | ON | OFF | ON | 101 |
| 294 | 0 | 1 | 1 | 0 | 0 | 1 | 1 | 0 | 1 | 8 | OFF | ON | ON | OFF | OFF | ON | ON | OFF | 102 |
| 295 | 0 | 1 | 1 | 0 | 0 | 1 | 1 | 1 | 1 | 12 | OFF | ON | ON | OFF | OFF | ON | ON | ON | 103 |
| 296 | 0 | 1 | 1 | 0 | 1 | 0 | 0 | 0 | 1 | 13 | OFF | ON | ON | OFF | ON | OFF | OFF | OFF | 104 |
| 297 | 0 | 1 | 1 | 0 | 1 | 0 | 0 | 1 | 1 | 14 | OFF | ON | ON | OFF | ON | OFF | OFF | ON | 105 |
| 298 | 0 | 1 | 1 | 0 | 1 | 0 | 1 | 0 | 1 | 15 | OFF | ON | ON | OFF | ON | OFF | ON | OFF | 106 |
| 299 | 0 | 1 | 1 | 0 | 1 | 0 | 1 | 1 | 1 | 16 | OFF | ON | ON | OFF | ON | OFF | ON | ON | 107 |
| 300 | 0 | 1 | 1 | 0 | 1 | 1 | 0 | 0 | 1 | 17 | OFF | ON | ON | OFF | ON | ON | OFF | OFF | 108 |
| 301 | 0 | 1 | 1 | 0 | 1 | 1 | 0 | 1 | 1 | 18 | OFF | ON | ON | OFF | ON | ON | OFF | ON | 109 |
| 302 | 0 | 1 | 1 | 0 | 1 | 1 | 1 | 0 | 2 | 2 | OFF | ON | ON | OFF | ON | ON | ON | OFF | 110 |
| 303 | 0 | 1 | 1 | 0 | 1 | 1 | 1 | 1 | 2 | 3 | OFF | ON | ON | OFF | ON | ON | ON | ON | 111 |
| 304 | 0 | 1 | 1 | 1 | 0 | 0 | 0 | 0 | 2 | 4 | OFF | ON | ON | ON | OFF | OFF | OFF | OFF | 112 |
| 305 | 0 | 1 | 1 | 1 | 0 | 0 | 0 | 1 | 2 | 5 | OFF | ON | ON | ON | OFF | OFF | OFF | ON | 113 |
| 306 | 0 | 1 | 1 | 1 | 0 | 0 | 1 | 0 | 2 | 6 | OFF | ON | ON | ON | OFF | OFF | ON | OFF | 114 |
| 307 | 0 | 1 | 1 | 1 | 0 | 0 | 1 | 1 | 2 | 7 | OFF | ON | ON | ON | OFF | OFF | ON | ON | 115 |
| 308 | 0 | 1 | 1 | 1 | 0 | 1 | 0 | 0 | 2 | 8 | OFF | ON | ON | ON | OFF | ON | OFF | OFF | 116 |
| 309 | 0 | 1 | 1 | 1 | 0 | 1 | 0 | 1 | 2 | 9 | OFF | ON | ON | ON | OFF | ON | OFF | ON | 117 |
| 310 | 0 | 1 | 1 | 1 | 0 | 1 | 1 | 0 | 2 | 10 | OFF | ON | ON | ON | OFF | ON | ON | OFF | 118 |
| 311 | 0 | 1 | 1 | 1 | 0 | 1 | 1 | 1 | 2 | 11 | OFF | ON | ON | ON | OFF | ON | ON | ON | 119 |
| 312 | 0 | 1 | 1 | 1 | 1 | 0 | 0 | 0 | 2 | 12 | OFF | ON | ON | ON | ON | OFF | OFF | OFF | 120 |
| 313 | 0 | 1 | 1 | 1 | 1 | 0 | 0 | 1 | 2 | 13 | OFF | ON | ON | ON | ON | OFF | OFF | ON | 121 |
| 314 | 0 | 1 | 1 | 1 | 1 | 0 | 1 | 0 | 2 | 14 | OFF | ON | ON | ON | ON | OFF | ON | OFF | 122 |
| 315 | 0 | 1 | 1 | 1 | 1 | 0 | 1 | 1 | 2 | 15 | OFF | ON | ON | ON | ON | OFF | ON | ON | 123 |
| 316 | 0 | 1 | 1 | 1 | 1 | 1 | 0 | 0 | 2 | 16 | OFF | ON | ON | ON | ON | ON | OFF | OFF | 124 |
| 317 | 0 | 1 | 1 | 1 | 1 | 1 | 0 | 1 | 2 | 17 | OFF | ON | ON | ON | ON | ON | OFF | ON | 125 |
| 318 | 0 | 1 | 1 | 1 | 1 | 1 | 1 | 0 | 2 | 18 | OFF | ON | ON | ON | ON | ON | ON | OFF | 126 |
| 319 | 0 | 1 | 1 | 1 | 1 | 1 | 1 | 1 | 3 | 2 | OFF | ON | ON | ON | ON | ON | ON | ON | 127 |

TABLE 7-continued

| | Presence or absence of analyte input (predetermined) Sample No. | | | | | | | | Position on array | | ON/OFF of signal (Result) Nucleic acid array (chip) | | | | | | | | |
|---|---|---|---|---|---|---|---|---|---|---|---|---|---|---|---|---|---|---|---|
| *a | 1 | 2 | 3 | 4 | 5 | 6 | 7 | 8 | *b | *c | 1 | 2 | 3 | 4 | 5 | 6 | 7 | 8 | *d |
| 320 | 1 | 0 | 0 | 0 | 0 | 0 | 0 | 0 | 3 | 3 | ON | OFF | OFF | OFF | OFF | OFF | OFF | OFF | 128 |
| 321 | 1 | 0 | 0 | 0 | 0 | 0 | 0 | 1 | 3 | 4 | ON | OFF | OFF | OFF | OFF | OFF | OFF | ON | 129 |
| 322 | 1 | 0 | 0 | 0 | 0 | 0 | 1 | 0 | 3 | 5 | ON | OFF | OFF | OFF | OFF | OFF | ON | OFF | 130 |
| 323 | 1 | 0 | 0 | 0 | 0 | 0 | 1 | 1 | 3 | 6 | ON | OFF | OFF | OFF | OFF | OFF | ON | ON | 131 |
| 324 | 1 | 0 | 0 | 0 | 0 | 1 | 0 | 0 | 3 | 7 | ON | OFF | OFF | OFF | OFF | ON | OFF | OFF | 132 |
| 325 | 1 | 0 | 0 | 0 | 0 | 1 | 0 | 1 | 3 | 8 | ON | OFF | OFF | OFF | OFF | ON | OFF | ON | 133 |
| 326 | 1 | 0 | 0 | 0 | 0 | 1 | 1 | 0 | 3 | 9 | ON | OFF | OFF | OFF | OFF | ON | ON | OFF | 134 |
| 327 | 1 | 0 | 0 | 0 | 0 | 1 | 1 | 1 | 3 | 10 | ON | OFF | OFF | OFF | OFF | ON | ON | ON | 135 |
| 328 | 1 | 0 | 0 | 0 | 1 | 0 | 0 | 0 | 3 | 11 | ON | OFF | OFF | OFF | ON | OFF | OFF | OFF | 136 |
| 329 | 1 | 0 | 0 | 0 | 1 | 0 | 0 | 1 | 3 | 12 | ON | OFF | OFF | OFF | ON | OFF | OFF | ON | 137 |
| 330 | 1 | 0 | 0 | 0 | 1 | 0 | 1 | 0 | 3 | 13 | ON | OFF | OFF | OFF | ON | OFF | ON | OFF | 138 |
| 331 | 1 | 0 | 0 | 0 | 1 | 0 | 1 | 1 | 3 | 14 | ON | OFF | OFF | OFF | ON | OFF | ON | ON | 139 |
| 332 | 1 | 0 | 0 | 0 | 1 | 1 | 0 | 0 | 3 | 15 | ON | OFF | OFF | OFF | ON | ON | OFF | OFF | 140 |
| 333 | 1 | 0 | 0 | 0 | 1 | 1 | 0 | 1 | 3 | 16 | ON | OFF | OFF | OFF | ON | ON | OFF | ON | 141 |
| 334 | 1 | 0 | 0 | 0 | 1 | 1 | 1 | 0 | 3 | 17 | ON | OFF | OFF | OFF | ON | ON | ON | OFF | 142 |
| 335 | 1 | 0 | 0 | 0 | 1 | 1 | 1 | 1 | 3 | 18 | ON | OFF | OFF | OFF | ON | ON | ON | ON | 143 |
| 336 | 1 | 0 | 0 | 1 | 0 | 0 | 0 | 0 | 4 | 2 | ON | OFF | OFF | ON | OFF | OFF | OFF | OFF | 144 |
| 337 | 1 | 0 | 0 | 1 | 0 | 0 | 0 | 1 | 10 | 2 | ON | OFF | OFF | ON | OFF | OFF | OFF | ON | 145 |
| 338 | 1 | 0 | 0 | 1 | 0 | 0 | 1 | 0 | 10 | 3 | ON | OFF | OFF | ON | OFF | OFF | ON | OFF | 146 |
| 339 | 1 | 0 | 0 | 1 | 0 | 0 | 1 | 1 | 10 | 4 | ON | OFF | OFF | ON | OFF | OFF | ON | ON | 147 |
| 340 | 1 | 0 | 0 | 1 | 0 | 1 | 0 | 0 | 10 | 5 | ON | OFF | OFF | ON | OFF | ON | OFF | OFF | 148 |
| 341 | 1 | 0 | 0 | 1 | 0 | 1 | 0 | 1 | 10 | 6 | ON | OFF | OFF | ON | OFF | ON | OFF | ON | 149 |
| 342 | 1 | 0 | 0 | 1 | 0 | 1 | 1 | 0 | 10 | 7 | ON | OFF | OFF | ON | OFF | ON | ON | OFF | 150 |
| 343 | 1 | 0 | 0 | 1 | 0 | 1 | 1 | 1 | 10 | 8 | ON | OFF | OFF | ON | OFF | ON | ON | ON | 151 |
| 344 | 1 | 0 | 0 | 1 | 1 | 0 | 0 | 0 | 10 | 9 | ON | OFF | OFF | ON | ON | OFF | OFF | OFF | 152 |
| 345 | 1 | 0 | 0 | 1 | 1 | 0 | 0 | 1 | 10 | 10 | ON | OFF | OFF | ON | ON | OFF | OFF | ON | 153 |
| 346 | 1 | 0 | 0 | 1 | 1 | 0 | 1 | 0 | 10 | 11 | ON | OFF | OFF | ON | ON | OFF | ON | OFF | 154 |
| 347 | 1 | 0 | 0 | 1 | 1 | 0 | 1 | 1 | 10 | 12 | ON | OFF | OFF | ON | ON | OFF | ON | ON | 155 |
| 348 | 1 | 0 | 0 | 1 | 1 | 1 | 0 | 0 | 10 | 13 | ON | OFF | OFF | ON | ON | ON | OFF | OFF | 156 |
| 349 | 1 | 0 | 0 | 1 | 1 | 1 | 0 | 1 | 10 | 14 | ON | OFF | OFF | ON | ON | ON | OFF | ON | 157 |
| 350 | 1 | 0 | 0 | 1 | 1 | 1 | 1 | 0 | 10 | 15 | ON | OFF | OFF | ON | ON | ON | ON | OFF | 158 |
| 351 | 1 | 0 | 0 | 1 | 1 | 1 | 1 | 1 | 10 | 16 | ON | OFF | OFF | ON | ON | ON | ON | ON | 159 |
| 352 | 1 | 0 | 1 | 0 | 0 | 0 | 0 | 0 | 10 | 17 | ON | OFF | ON | OFF | OFF | OFF | OFF | OFF | 160 |
| 353 | 1 | 0 | 1 | 0 | 0 | 0 | 0 | 1 | 10 | 18 | ON | OFF | ON | OFF | OFF | OFF | OFF | ON | 161 |
| 354 | 1 | 0 | 1 | 0 | 0 | 0 | 1 | 0 | 11 | 2 | ON | OFF | ON | OFF | OFF | OFF | ON | OFF | 162 |
| 355 | 1 | 0 | 1 | 0 | 0 | 0 | 1 | 1 | 11 | 3 | ON | OFF | ON | OFF | OFF | OFF | ON | ON | 163 |
| 356 | 1 | 0 | 1 | 0 | 0 | 1 | 0 | 0 | 11 | 4 | ON | OFF | ON | OFF | OFF | ON | OFF | OFF | 164 |
| 357 | 1 | 0 | 1 | 0 | 0 | 1 | 0 | 1 | 11 | 5 | ON | OFF | ON | OFF | OFF | ON | OFF | ON | 165 |
| 358 | 1 | 0 | 1 | 0 | 0 | 1 | 1 | 0 | 11 | 6 | ON | OFF | ON | OFF | OFF | ON | ON | OFF | 166 |
| 359 | 1 | 0 | 1 | 0 | 0 | 1 | 1 | 1 | 11 | 7 | ON | OFF | ON | OFF | OFF | ON | ON | ON | 167 |
| 360 | 1 | 0 | 1 | 0 | 1 | 0 | 0 | 0 | 11 | 8 | ON | OFF | ON | OFF | ON | OFF | OFF | OFF | 168 |
| 361 | 1 | 0 | 1 | 0 | 1 | 0 | 0 | 1 | 11 | 9 | ON | OFF | ON | OFF | ON | OFF | OFF | ON | 169 |
| 362 | 1 | 0 | 1 | 0 | 1 | 0 | 1 | 0 | 11 | 10 | ON | OFF | ON | OFF | ON | OFF | ON | OFF | 170 |
| 363 | 1 | 0 | 1 | 0 | 1 | 0 | 1 | 1 | 11 | 11 | ON | OFF | ON | OFF | ON | OFF | ON | ON | 171 |
| 364 | 1 | 0 | 1 | 0 | 1 | 1 | 0 | 0 | 11 | 12 | ON | OFF | ON | OFF | ON | ON | OFF | OFF | 172 |
| 365 | 1 | 0 | 1 | 0 | 1 | 1 | 0 | 1 | 11 | 13 | ON | OFF | ON | OFF | ON | ON | OFF | ON | 173 |
| 366 | 1 | 0 | 1 | 0 | 1 | 1 | 1 | 0 | 11 | 14 | ON | OFF | ON | OFF | ON | ON | ON | OFF | 174 |
| 367 | 1 | 0 | 1 | 0 | 1 | 1 | 1 | 1 | 11 | 15 | ON | OFF | ON | OFF | ON | ON | ON | ON | 175 |
| 368 | 1 | 0 | 1 | 1 | 0 | 0 | 0 | 0 | 11 | 16 | ON | OFF | ON | ON | OFF | OFF | OFF | OFF | 176 |
| 369 | 1 | 0 | 1 | 1 | 0 | 0 | 0 | 1 | 11 | 17 | ON | OFF | ON | ON | OFF | OFF | OFF | ON | 177 |
| 370 | 1 | 0 | 1 | 1 | 0 | 0 | 1 | 0 | 11 | 18 | ON | OFF | ON | ON | OFF | OFF | ON | OFF | 178 |
| 371 | 1 | 0 | 1 | 1 | 0 | 0 | 1 | 1 | 12 | 2 | ON | OFF | ON | ON | OFF | OFF | ON | ON | 179 |
| 372 | 1 | 0 | 1 | 1 | 0 | 1 | 0 | 0 | 12 | 3 | ON | OFF | ON | ON | OFF | ON | OFF | OFF | 180 |
| 373 | 1 | 0 | 1 | 1 | 0 | 1 | 0 | 1 | 12 | 4 | ON | OFF | ON | ON | OFF | ON | OFF | ON | 181 |
| 374 | 1 | 0 | 1 | 1 | 0 | 1 | 1 | 0 | 12 | 5 | ON | OFF | ON | ON | OFF | ON | ON | OFF | 182 |
| 375 | 1 | 0 | 1 | 1 | 0 | 1 | 1 | 1 | 12 | 6 | ON | OFF | ON | ON | OFF | ON | ON | ON | 183 |
| 376 | 1 | 0 | 1 | 1 | 1 | 0 | 0 | 0 | 12 | 7 | ON | OFF | ON | ON | ON | OFF | OFF | OFF | 184 |
| 377 | 1 | 0 | 1 | 1 | 1 | 0 | 0 | 1 | 12 | 8 | ON | OFF | ON | ON | ON | OFF | OFF | ON | 185 |
| 378 | 1 | 0 | 1 | 1 | 1 | 0 | 1 | 0 | 12 | 12 | ON | OFF | ON | ON | ON | OFF | ON | OFF | 186 |
| 379 | 1 | 0 | 1 | 1 | 1 | 0 | 1 | 1 | 12 | 13 | ON | OFF | ON | ON | ON | OFF | ON | ON | 187 |
| 380 | 1 | 0 | 1 | 1 | 1 | 1 | 0 | 0 | 12 | 14 | ON | OFF | ON | ON | ON | ON | OFF | OFF | 188 |
| 381 | 1 | 0 | 1 | 1 | 1 | 1 | 0 | 1 | 12 | 15 | ON | OFF | ON | ON | ON | ON | OFF | ON | 189 |
| 382 | 1 | 0 | 1 | 1 | 1 | 1 | 1 | 0 | 12 | 16 | ON | OFF | ON | ON | ON | ON | ON | OFF | 190 |
| 383 | 1 | 0 | 1 | 1 | 1 | 1 | 1 | 1 | 12 | 17 | ON | OFF | ON | ON | ON | ON | ON | ON | 191 |
| 384 | 1 | 1 | 0 | 0 | 0 | 0 | 0 | 0 | 12 | 18 | ON | ON | OFF | OFF | OFF | OFF | OFF | OFF | 192 |

*a: SEQ ID NO:,
*b: Column,
*c: Row,
*d: Corresponding SEQ ID NO:

Patterns of signals for all the nucleic acid probes immobilized on the array are different from each other. Further, patterns of signals expected from the complementary nucleic acid molecules included in Samples 1-8 corresponded to the actual patterns of signals. Accordingly, it was confirmed that these nucleic acid probes are present on predetermined positions. It became clear that immobilization positions of nucleic acid probes can be confirmed by using this technique.

Sequence Listing Free Text

SEQ ID NOs: 1-385: synthetic DNA

INDUSTRIAL APPLICABILITY

According to the present invention, a method for confirming the types and positions of respective nucleic acid probes immobilized on a nucleic acid array by means of hybridization between the nucleic acid probes and nucleic acids comprising a complementary sequence thereof is provided.

To confirm whether or not individual probes on a nucleic acid array are arrayed on predetermined positions is the most important examination item in terms of the quality control of DNA microarrays. According to the present invention, the positions on which the probes are arrayed can be accurately and easily examined.

What is claimed is:

1. A method for confirming immobilization conditions of nucleic acid probes immobilized on a nucleic acid array, comprising the steps of:
(a) defining the number of zones to which the nucleic acid probes immobilized on the nucleic acid array belong and one or more given pieces of identification information;
(b) calculating X using the following formula:

$$X=\{\log_{(N+1)}M\}+1$$

(wherein N represents the number of the pieces of identification information, and M represents the number of the zones to which the nucleic acid probes immobilized on the nucleic acid array belong),
defining a number of the integer portion of X as the number of nucleic acid arrays required for confirming the immobilization conditions, $X_a$, and allocating non-overlapping numerical values
(Y), which are expressed by notation system of base N+1, and which have the same digit number as $X_a$, to the respective nucleic acid probes belonging to the zones;
(c) preparing complementary nucleic acid molecules comprising nucleotide sequences complementary to all or a part of nucleotide sequences of the nucleic acid probes, preparing groups of nucleic acid samples corresponding to the number of nucleic acid arrays ($X_a$) by mixing the complementary nucleic acid molecules based on the number of every digit of each of the allocated numerical values (Y), and preparing nucleic acid arrays (the number: $X_a$);
(d) contacting each of the nucleic acid arrays (the number: $X_a$) prepared in the step (c) with the corresponding group of the nucleic acid samples to detect signals derived from hybrids between the nucleic acid probes immobilized on the nucleic acid arrays and the complementary nucleic acid molecules;
(e) matching patterns of expression of the signals detected to patterns of the numerical values (Y) allocated; and
(f) confirming the immobilization conditions when the patterns of expression match the patterns of the numeric values (Y).

2. The method according to claim 1, wherein the immobilization conditions of the nucleic acid probes are related to types and/or positions of the nucleic acid probes.

3. The method according to claim 1, wherein the identification information is at least one selected from the group consisting of: a presence or an absence of the signal; a strength of the signal; and a type of labeling.

4. The method according to claim 1, wherein the patterns of expression of the signals detected are quantified by notation system of base N+1 based on the identification information.

5. A method for examining a quality of nucleic acid arrays, wherein the quality of the nucleic acid arrays is examined based on results obtained according to the method according to claim 1.

* * * * *